(12) United States Patent
Nae et al.

(10) Patent No.: US 11,612,385 B2
(45) Date of Patent: Mar. 28, 2023

(54) SYSTEMS AND METHODS FOR DELIVERING IMPLANTABLE DEVICES ACROSS AN ATRIAL SEPTUM

(71) Applicant: V-Wave Ltd., Caesarea (IL)

(72) Inventors: Nir Nae, Binyamina (IL); Lior Rosen, Or Akiva (IL); Ye'ela Scop, Tel Aviv (IL); Neal Eigler, Malibu, CA (US); Erez Rozenfeld, Shoham (IL)

(73) Assignee: V-Wave Ltd., Caesarea (IL)

( * ) Notice: Subject to any disclaimer, the term of this patent is extended or adjusted under 35 U.S.C. 154(b) by 1029 days.

(21) Appl. No.: 16/374,698

(22) Filed: Apr. 3, 2019

(65) Prior Publication Data

US 2020/0315599 A1 Oct. 8, 2020

(51) Int. Cl.
*A61B 17/00* (2006.01)
*A61M 25/00* (2006.01)

(52) U.S. Cl.
CPC .......... *A61B 17/0057* (2013.01); *A61B 2017/00243* (2013.01); *A61B 2017/00623* (2013.01); *A61F 2220/0008* (2013.01); *A61M 25/00* (2013.01)

(58) Field of Classification Search
CPC ...... A61B 2017/00575; A61B 17/0057; A61B 17/11; A61B 17/00234; A61B 17/1285;
(Continued)

(56) References Cited

U.S. PATENT DOCUMENTS 3,852,334 A 12/1974 Dusza et al.
3,874,388 A 4/1975 King et al.
(Continued)

FOREIGN PATENT DOCUMENTS

AU 2003291117 B2 4/2009
CA 2378920 A1 2/2001
(Continued)

OTHER PUBLICATIONS

Ando et al., "Left ventricular decompression through a patent foramen ovale in a patient with hypertropic cardiomyopathy: A case report," Cardiovascular Ultrasound 2: 1-7 (2004).
(Continued)

*Primary Examiner* — Erich G Herbermann
*Assistant Examiner* — Linnae E. Raymond
(74) *Attorney, Agent, or Firm* — Eversheds Sutherland (US) LLP; Christopher C. Bolten; Albert K. Heng

(57) ABSTRACT

Systems and methods for delivering a device for regulating blood pressure between a patient's left atrium and right atrium are provided. The delivery apparatus may include a first catheter, a hub having one or more engagers disposed thereon configured to releasably engage with a first expandable end of the shunt in a contracted delivery state within a lumen of a sheath, and a second catheter extending through a center lumen of the first catheter and the hub, wherein the first catheter, the hub, and the second catheter are independently moveable relative to the sheath. The inventive devices may reduce left atrial pressure and left ventricular end diastolic pressure, and may increase cardiac output, increase ejection fraction, relieve pulmonary congestion, and lower pulmonary artery pressure, among other benefits. The inventive devices may be used, for example, to treat subjects having heart failure, pulmonary congestion, or myocardial infarction, among other pathologies.

20 Claims, 59 Drawing Sheets

(58) Field of Classification Search
CPC ...... A61B 5/076; A61F 2/2436; A61F 2/2418; A61F 2/07; A61F 2/2493; A61F 2/90; A61F 2/06; A61F 2/24; A61F 2/82; A61F 2/95; A61F 2/966; A61F 2/243; A61F 2/064; A61F 2/01; A61F 2/2466; A61F 2/2487; A61M 25/00; A61M 25/01
See application file for complete search history.

(56) References Cited

U.S. PATENT DOCUMENTS

| | | |
|---|---|---|
| 3,952,334 A | 4/1976 | Bokros et al. |
| 4,484,955 A | 11/1984 | Hochstein |
| 4,601,309 A | 7/1986 | Chang |
| 4,617,932 A | 10/1986 | Kornberg |
| 4,662,355 A | 5/1987 | Pieronne et al. |
| 4,665,906 A | 5/1987 | Jervis |
| 4,705,507 A | 11/1987 | Boyles |
| 4,836,204 A | 6/1989 | Landymore et al. |
| 4,979,955 A | 12/1990 | Smith |
| 4,988,339 A | 1/1991 | Vadher |
| 4,995,857 A | 2/1991 | Arnold |
| 5,035,702 A | 7/1991 | Taheri |
| 5,035,706 A | 7/1991 | Giantureo et al. |
| 5,037,427 A | 8/1991 | Harada et al. |
| 5,089,005 A | 2/1992 | Harada |
| 5,186,431 A | 2/1993 | Tamari |
| 5,197,978 A | 3/1993 | Hess |
| 5,234,447 A | 8/1993 | Kaster et al. |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,378,239 A | 1/1995 | Termin et al. |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,545,210 A | 8/1996 | Hess et al. |
| 5,556,386 A | 9/1996 | Todd |
| 5,578,008 A | 11/1996 | Hara |
| 5,584,803 A | 12/1996 | Stevens et al. |
| 5,597,377 A | 1/1997 | Aldea |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,741,324 A | 4/1998 | Glastra |
| 5,749,880 A | 5/1998 | Banas et al. |
| 5,779,716 A | 7/1998 | Cano et al. |
| 5,795,307 A | 8/1998 | Krueger |
| 5,810,836 A | 9/1998 | Hussein et al. |
| 5,824,062 A | 10/1998 | Patke et al. |
| 5,824,071 A | 10/1998 | Nelson et al. |
| 5,846,261 A | 12/1998 | Kotula et al. |
| 5,910,144 A | 6/1999 | Hayashi |
| 5,916,193 A | 6/1999 | Stevens et al. |
| 5,941,850 A | 8/1999 | Shah et al. |
| 5,957,949 A | 9/1999 | Leonhardt et al. |
| 5,990,379 A | 11/1999 | Gregory |
| 6,027,518 A | 2/2000 | Gaber |
| 6,039,755 A | 3/2000 | Edwin et al. |
| 6,039,759 A | 3/2000 | Carpentier et al. |
| 6,086,610 A | 7/2000 | Duerig et al. |
| 6,111,520 A | 8/2000 | Allen et al. |
| 6,117,159 A | 9/2000 | Huebsch et al. |
| 6,120,534 A | 9/2000 | Ruiz |
| 6,124,523 A | 9/2000 | Banas et al. |
| 6,126,686 A | 10/2000 | Badylak et al. |
| 6,165,188 A | 12/2000 | Saadat et al. |
| 6,210,318 B1 | 4/2001 | Lederman |
| 6,214,039 B1 | 4/2001 | Banas et al. |
| 6,217,541 B1 | 4/2001 | Yu |
| 6,221,096 B1 | 4/2001 | Aiba et al. |
| 6,231,587 B1 | 5/2001 | Makower |
| 6,242,762 B1 | 6/2001 | Brown et al. |
| 6,245,099 B1 | 6/2001 | Edwin et al. |
| 6,254,564 B1 | 7/2001 | Wilk et al. |
| 6,260,552 B1 | 7/2001 | Mortier et al. |
| 6,264,684 B1 | 7/2001 | Banas et al. |
| 6,270,515 B1 | 8/2001 | Linden et al. |
| 6,270,526 B1 | 8/2001 | Cox |
| 6,277,078 B1 | 8/2001 | Porat et al. |
| 6,278,379 B1 | 8/2001 | Allen et al. |
| 6,302,892 B1 | 10/2001 | Wilk |
| 6,306,141 B1 | 10/2001 | Jervis |
| 6,328,699 B1 | 12/2001 | Eigler et al. |
| 6,344,022 B1 | 2/2002 | Jarvik |
| 6,358,277 B1 | 3/2002 | Duran |
| 6,391,036 B1 | 5/2002 | Berg et al. |
| 6,398,803 B1 | 6/2002 | Layne et al. |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,475,136 B1 | 11/2002 | Forsell |
| 6,478,776 B1 | 11/2002 | Rosenman et al. |
| 6,485,507 B1 | 11/2002 | Walak et al. |
| 6,488,702 B1 | 12/2002 | Besselink |
| 6,491,705 B2 | 12/2002 | Gifford et al. |
| 6,527,698 B1 | 3/2003 | Kung et al. |
| 6,544,208 B2 | 4/2003 | Ethier et al. |
| 6,547,814 B2 | 4/2003 | Edwin et al. |
| 6,562,066 B1 | 5/2003 | Martin |
| 6,572,652 B2 | 6/2003 | Shaknovich |
| 6,579,314 B1 | 6/2003 | Lombardi et al. |
| 6,589,198 B1 | 7/2003 | Soltanpour et al. |
| 6,616,675 B1 | 9/2003 | Evard et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,652,578 B2 | 11/2003 | Bailey et al. |
| 6,685,664 B2 | 2/2004 | Levin et al. |
| 6,712,836 B1 | 3/2004 | Berg et al. |
| 6,740,115 B2 | 5/2004 | Lombardi et al. |
| 6,758,858 B2 | 7/2004 | McCrea et al. |
| 6,764,507 B2 | 7/2004 | Shanley et al. |
| 6,770,087 B2 | 8/2004 | Layne et al. |
| 6,797,217 B2 | 9/2004 | McCrea et al. |
| 6,890,350 B1 | 5/2005 | Walak |
| 6,923,829 B2 | 8/2005 | Boyle et al. |
| 6,970,742 B2 | 11/2005 | Mann et al. |
| 7,001,409 B2 | 2/2006 | Amplatz |
| 7,004,966 B2 | 2/2006 | Edwin et al. |
| 7,025,777 B2 | 4/2006 | Moore |
| 7,060,150 B2 | 6/2006 | Banas et al. |
| 7,083,640 B2 | 8/2006 | Lombardi et al. |
| 7,115,095 B2 | 10/2006 | Eigler et al. |
| 7,118,600 B2 | 10/2006 | Dua et al. |
| 7,137,953 B2 | 11/2006 | Eigler et al. |
| 7,147,604 B1 | 12/2006 | Allen et al. |
| 7,149,587 B2 | 12/2006 | Wardle et al. |
| 7,169,160 B1 | 1/2007 | Middleman et al. |
| 7,169,172 B2 | 1/2007 | Levine et al. |
| 7,195,594 B2 | 3/2007 | Eigler et al. |
| 7,208,010 B2 | 4/2007 | Shanley et al. |
| 7,226,558 B2 | 6/2007 | Nieman et al. |
| 7,245,117 B1 | 7/2007 | Joy et al. |
| 7,294,115 B1 | 11/2007 | Wilk |
| 7,306,756 B2 | 12/2007 | Edwin et al. |
| 7,402,899 B1 | 7/2008 | Whiting et al. |
| 7,439,723 B2 | 10/2008 | Allen et al. |
| 7,468,071 B2 | 12/2008 | Edwin et al. |
| 7,483,743 B2 | 1/2009 | Mann et al. |
| 7,498,799 B2 | 3/2009 | Allen et al. |
| 7,509,169 B2 | 3/2009 | Eigler et al. |
| 7,550,978 B2 | 6/2009 | Joy et al. |
| 7,578,899 B2 | 8/2009 | Edwin et al. |
| 7,590,449 B2 | 9/2009 | Mann et al. |
| 7,615,010 B1 | 11/2009 | Najafi et al. |
| 7,621,879 B2 | 11/2009 | Eigler et al. |

(56) References Cited

U.S. PATENT DOCUMENTS

| | | |
|---|---|---|
| 7,679,355 B2 | 3/2010 | Allen et al. |
| 7,717,854 B2 | 5/2010 | Mann et al. |
| 7,794,473 B2 | 9/2010 | Tessmer et al. |
| 7,839,153 B2 | 11/2010 | Joy et al. |
| 7,842,083 B2 | 11/2010 | Shanley et al. |
| 7,854,172 B2 | 12/2010 | O'Brien et al. |
| 7,862,513 B2 | 1/2011 | Eigler et al. |
| 7,914,639 B2 | 3/2011 | Layne et al. |
| 7,939,000 B2 | 5/2011 | Edwin et al. |
| 7,988,724 B2 | 8/2011 | Salahieh et al. |
| 7,993,383 B2 | 8/2011 | Hartley et al. |
| 8,012,194 B2 | 9/2011 | Edwin et al. |
| 8,016,877 B2 | 9/2011 | Seguin et al. |
| 8,021,420 B2 | 9/2011 | Dolan |
| 8,025,625 B2 | 9/2011 | Allen |
| 8,025,668 B2 | 9/2011 | McCartney |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,137,605 B2 | 3/2012 | McCrea et al. |
| 8,142,363 B1 | 3/2012 | Eigler et al. |
| 8,147,545 B2 | 4/2012 | Avior |
| 8,157,852 B2 | 4/2012 | Bloom et al. |
| 8,157,860 B2 | 4/2012 | McNamara et al. |
| 8,157,940 B2 | 4/2012 | Edwin et al. |
| 8,158,041 B2 | 4/2012 | Colone |
| 8,187,321 B2 | 5/2012 | Shanley et al. |
| 8,202,313 B2 | 6/2012 | Shanley et al. |
| 8,206,435 B2 | 6/2012 | Shanley et al. |
| 8,235,916 B2 | 8/2012 | Whiting et al. |
| 8,235,933 B2 | 8/2012 | Keren et al. |
| 8,246,677 B2 | 8/2012 | Ryan |
| 8,287,589 B2 | 10/2012 | Otto et al. |
| 8,298,150 B2 | 10/2012 | Mann et al. |
| 8,298,244 B2 | 10/2012 | Garcia et al. |
| 8,303,511 B2 | 11/2012 | Eigler et al. |
| 8,313,524 B2 | 11/2012 | Edwin et al. |
| 8,328,751 B2 | 12/2012 | Keren et al. |
| 8,337,650 B2 | 12/2012 | Edwin et al. |
| 8,348,996 B2 | 1/2013 | Tuval et al. |
| 8,357,193 B2 | 1/2013 | Phan et al. |
| 8,398,708 B2 | 3/2013 | Meiri et al. |
| 8,460,366 B2 | 6/2013 | Rowe |
| 8,468,667 B2 | 6/2013 | Straubinger et al. |
| 8,480,594 B2 | 7/2013 | Eigler et al. |
| 8,579,966 B2 | 11/2013 | Seguin et al. |
| 8,597,225 B2 | 12/2013 | Kapadia |
| 8,617,337 B2 | 12/2013 | Layne et al. |
| 8,617,441 B2 | 12/2013 | Edwin et al. |
| 8,652,284 B2 | 2/2014 | Bogert et al. |
| 8,665,086 B2 | 3/2014 | Miller et al. |
| 8,696,611 B2 | 4/2014 | Nitzan et al. |
| 8,790,241 B2 | 7/2014 | Edwin et al. |
| 8,882,697 B2 | 11/2014 | Celermajer et al. |
| 8,882,798 B2 | 11/2014 | Schwab et al. |
| 8,911,489 B2 | 12/2014 | Ben-Muvhar |
| 9,005,155 B2 | 4/2015 | Sugimoto |
| 9,034,034 B2 | 5/2015 | Nitzan et al. |
| 9,055,917 B2 | 6/2015 | Mann et al. |
| 9,060,696 B2 | 6/2015 | Eigler et al. |
| 9,067,050 B2 | 6/2015 | Gallagher et al. |
| 9,205,236 B2 | 12/2015 | McNamara et al. |
| 9,220,429 B2 | 12/2015 | Nabutovsky et al. |
| 9,358,371 B2 | 6/2016 | McNamara et al. |
| 9,393,115 B2 | 7/2016 | Tabor et al. |
| 9,456,812 B2 | 10/2016 | Finch et al. |
| 9,622,895 B2 | 4/2017 | Cohen et al. |
| 9,629,715 B2 | 4/2017 | Nitzan et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,757,107 B2 | 9/2017 | McNamara et al. |
| 9,789,294 B2 | 10/2017 | Taft et al. |
| 9,918,677 B2 | 3/2018 | Eigler et al. |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,047,421 B2 | 8/2018 | Khan et al. |
| 10,076,403 B1 | 9/2018 | Eigler et al. |
| 10,105,103 B2 | 10/2018 | Goldshtein et al. |
| 10,111,741 B2 | 10/2018 | Michalak |
| 10,207,087 B2 | 2/2019 | Keren et al. |
| 10,207,807 B2 | 2/2019 | Moran et al. |
| 10,251,740 B2 | 4/2019 | Eigler et al. |
| 10,251,750 B2 | 4/2019 | Alexander et al. |
| 10,265,169 B2 * | 4/2019 | Desrosiers ............ A61F 2/2418 |
| 10,299,687 B2 | 5/2019 | Nabutovsky et al. |
| 10,357,320 B2 | 7/2019 | Beira |
| 10,357,357 B2 | 7/2019 | Levi et al. |
| 10,368,981 B2 | 8/2019 | Nitzan et al. |
| 10,463,490 B2 | 11/2019 | Rottenberg et al. |
| 10,478,594 B2 | 11/2019 | Yacoby et al. |
| 10,548,725 B2 | 2/2020 | Alkhatib et al. |
| 10,561,423 B2 | 2/2020 | Sharma |
| 10,583,002 B2 * | 3/2020 | Lane .................... A61F 2/2412 |
| 10,639,459 B2 | 5/2020 | Nitzan et al. |
| 10,828,151 B2 | 11/2020 | Nitzan et al. |
| 10,835,394 B2 | 11/2020 | Nae et al. |
| 10,898,698 B1 | 1/2021 | Eigler et al. |
| 10,912,645 B2 | 2/2021 | Rottenberg et al. |
| 10,925,706 B2 | 2/2021 | Eigler et al. |
| 10,940,296 B2 | 3/2021 | Keren |
| 11,234,702 B1 | 2/2022 | Eigler et al. |
| 11,253,353 B2 | 2/2022 | Levi et al. |
| 11,291,807 B2 | 4/2022 | Eigler et al. |
| 11,304,831 B2 | 4/2022 | Nae et al. |
| 2001/0021872 A1 | 9/2001 | Bailey et al. |
| 2002/0120277 A1 | 8/2002 | Hauschild et al. |
| 2002/0165479 A1 | 11/2002 | Wilk |
| 2002/0165606 A1 | 11/2002 | Wolf et al. |
| 2002/0169371 A1 | 11/2002 | Gilderdale |
| 2002/0169377 A1 | 11/2002 | Khairkhahan et al. |
| 2002/0173742 A1 | 11/2002 | Keren et al. |
| 2002/0183628 A1 | 12/2002 | Reich et al. |
| 2003/0028213 A1 | 2/2003 | Thill et al. |
| 2003/0045902 A1 | 3/2003 | Weadock |
| 2003/0100920 A1 | 5/2003 | Akin et al. |
| 2003/0125798 A1 | 7/2003 | Martin |
| 2003/0136417 A1 | 7/2003 | Fonseca et al. |
| 2003/0139819 A1 | 7/2003 | Beer et al. |
| 2003/0176914 A1 | 9/2003 | Rabkin et al. |
| 2003/0209835 A1 | 11/2003 | Chun et al. |
| 2003/0216679 A1 | 11/2003 | Wolf et al. |
| 2003/0216803 A1 | 11/2003 | Ledergerber |
| 2004/0010219 A1 | 1/2004 | McCusker et al. |
| 2004/0016514 A1 | 1/2004 | Nien |
| 2004/0073242 A1 | 4/2004 | Chanduszko |
| 2004/0077988 A1 | 4/2004 | Tweden et al. |
| 2004/0088045 A1 | 5/2004 | Cox |
| 2004/0093075 A1 | 5/2004 | Kuehne |
| 2004/0102797 A1 | 5/2004 | Golden et al. |
| 2004/0116999 A1 | 6/2004 | Ledergerber |
| 2004/0138743 A1 | 7/2004 | Myers et al. |
| 2004/0147869 A1 | 7/2004 | Wolf et al. |
| 2004/0147871 A1 | 7/2004 | Burnett |
| 2004/0147886 A1 | 7/2004 | Bonni |
| 2004/0147969 A1 | 7/2004 | Mann et al. |
| 2004/0162514 A1 | 8/2004 | Alferness et al. |
| 2004/0193261 A1 | 9/2004 | Berreklouw |
| 2004/0210190 A1 | 10/2004 | Kohler et al. |
| 2004/0210307 A1 | 10/2004 | Khairkhahan |
| 2004/0225352 A1 | 11/2004 | Osborne et al. |
| 2005/0003327 A1 | 1/2005 | Elian et al. |
| 2005/0033327 A1 | 2/2005 | Gainor et al. |
| 2005/0033351 A1 | 2/2005 | Newton |
| 2005/0065589 A1 | 3/2005 | Schneider et al. |
| 2005/0125032 A1 | 6/2005 | Whisenant et al. |
| 2005/0137682 A1 | 6/2005 | Justino |
| 2005/0148925 A1 | 7/2005 | Rottenberg et al. |
| 2005/0165344 A1 | 7/2005 | Dobak, III |
| 2005/0182486 A1 | 8/2005 | Gabbay |
| 2005/0267524 A1 | 12/2005 | Chanduszko |
| 2005/0283231 A1 | 12/2005 | Haug et al. |

(56) References Cited

U.S. PATENT DOCUMENTS

| | | |
|---|---|---|
| 2005/0288596 A1 | 12/2005 | Eigler et al. |
| 2005/0288706 A1 | 12/2005 | Widomski et al. |
| 2005/0288786 A1 | 12/2005 | Chanduszko |
| 2006/0009800 A1 | 1/2006 | Christianson et al. |
| 2006/0025857 A1 | 2/2006 | Bergheim et al. |
| 2006/0111660 A1 | 5/2006 | Wolf et al. |
| 2006/0116710 A1 | 6/2006 | Corcoran et al. |
| 2006/0122522 A1 | 6/2006 | Chavan et al. |
| 2006/0122647 A1 | 6/2006 | Callaghan et al. |
| 2006/0167541 A1 | 7/2006 | Lattouf |
| 2006/0184231 A1 | 8/2006 | Rucker |
| 2006/0212110 A1 | 9/2006 | Osborne et al. |
| 2006/0241745 A1 | 10/2006 | Solem |
| 2006/0256611 A1 | 11/2006 | Bednorz et al. |
| 2006/0282157 A1 | 12/2006 | Hill et al. |
| 2007/0010852 A1 | 1/2007 | Blaeser et al. |
| 2007/0021739 A1 | 1/2007 | Weber |
| 2007/0043435 A1 | 2/2007 | Seguin et al. |
| 2007/0129756 A1 | 6/2007 | Abbott et al. |
| 2007/0191863 A1 | 8/2007 | De Juan, Jr. et al. |
| 2007/0213813 A1 | 9/2007 | Von Segesser et al. |
| 2007/0276413 A1 | 11/2007 | Nobles |
| 2007/0276414 A1 | 11/2007 | Nobles |
| 2007/0282157 A1 | 12/2007 | Rottenberg et al. |
| 2007/0299384 A1 | 12/2007 | Faul et al. |
| 2008/0034836 A1 | 2/2008 | Eigler et al. |
| 2008/0086205 A1 | 4/2008 | Gordy et al. |
| 2008/0125861 A1 | 5/2008 | Webler et al. |
| 2008/0177300 A1 | 7/2008 | Mas et al. |
| 2008/0262602 A1 | 10/2008 | Wilk et al. |
| 2008/0319525 A1 | 12/2008 | Tieu et al. |
| 2009/0030499 A1 | 1/2009 | Bebb et al. |
| 2009/0054976 A1 | 2/2009 | Tuval et al. |
| 2009/0125104 A1 | 5/2009 | Hoffman |
| 2009/0149947 A1 | 6/2009 | Frohwitter |
| 2009/0198315 A1 | 8/2009 | Boudjemline |
| 2009/0276040 A1 | 11/2009 | Rowe et al. |
| 2009/0319037 A1 | 12/2009 | Rowe et al. |
| 2010/0004740 A1 | 1/2010 | Seguin et al. |
| 2010/0022940 A1 | 1/2010 | Thompson |
| 2010/0057192 A1 | 3/2010 | Celermajer |
| 2010/0069836 A1 | 3/2010 | Satake |
| 2010/0070022 A1 | 3/2010 | Kuehling |
| 2010/0081867 A1 | 4/2010 | Fishler et al. |
| 2010/0100167 A1 | 4/2010 | Bortlein et al. |
| 2010/0121434 A1 | 5/2010 | Paul et al. |
| 2010/0179590 A1 | 7/2010 | Fortson et al. |
| 2010/0191326 A1 | 7/2010 | Alkhatib |
| 2010/0249909 A1 | 9/2010 | McNamara et al. |
| 2010/0249910 A1 | 9/2010 | McNamara et al. |
| 2010/0249915 A1 | 9/2010 | Zhang |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2010/0324652 A1* | 12/2010 | Aurilia ............... B29C 65/02 623/1.18 |
| 2011/0022057 A1 | 1/2011 | Eigler et al. |
| 2011/0022157 A1 | 1/2011 | Essinger et al. |
| 2011/0054515 A1 | 3/2011 | Bridgeman et al. |
| 2011/0071623 A1 | 3/2011 | Finch et al. |
| 2011/0071624 A1 | 3/2011 | Finch et al. |
| 2011/0093059 A1 | 4/2011 | Fischell et al. |
| 2011/0152923 A1 | 6/2011 | Fox |
| 2011/0190874 A1 | 8/2011 | Celermajer et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0257723 A1 | 10/2011 | McNamara |
| 2011/0264203 A1 | 10/2011 | Dwork et al. |
| 2011/0276086 A1 | 11/2011 | Al-Qbandi et al. |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0319806 A1 | 12/2011 | Wardle |
| 2012/0022507 A1 | 1/2012 | Najafi et al. |
| 2012/0022633 A1 | 1/2012 | Olson et al. |
| 2012/0035590 A1 | 2/2012 | Whiting et al. |
| 2012/0041422 A1 | 2/2012 | Whiting et al. |
| 2012/0046528 A1 | 2/2012 | Eigler et al. |
| 2012/0046739 A1 | 2/2012 | Von Oepen et al. |
| 2012/0053686 A1 | 3/2012 | McNamara et al. |
| 2012/0071918 A1 | 3/2012 | Amin et al. |
| 2012/0130301 A1 | 5/2012 | McNamara et al. |
| 2012/0165928 A1 | 6/2012 | Nitzan et al. |
| 2012/0179172 A1 | 7/2012 | Paul et al. |
| 2012/0190991 A1 | 7/2012 | Bornzin et al. |
| 2012/0265296 A1 | 10/2012 | McNamara et al. |
| 2012/0271398 A1 | 10/2012 | Essinger et al. |
| 2012/0289882 A1 | 11/2012 | McNamara et al. |
| 2012/0290062 A1 | 11/2012 | McNamara et al. |
| 2013/0030521 A1 | 1/2013 | Nitzan et al. |
| 2013/0046373 A1 | 2/2013 | Cartledge et al. |
| 2013/0138145 A1 | 5/2013 | Von Oepen |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0197423 A1 | 8/2013 | Keren et al. |
| 2013/0197547 A1 | 8/2013 | Fukuoka et al. |
| 2013/0197629 A1 | 8/2013 | Gainor et al. |
| 2013/0204175 A1 | 8/2013 | Sugimoto |
| 2013/0231737 A1 | 9/2013 | McNamara et al. |
| 2013/0261531 A1 | 10/2013 | Gallagher et al. |
| 2013/0281988 A1 | 10/2013 | Magnin et al. |
| 2013/0304192 A1 | 11/2013 | Chanduszko |
| 2014/0012181 A1 | 1/2014 | Sugimoto et al. |
| 2014/0012303 A1 | 1/2014 | Heipl |
| 2014/0012368 A1 | 1/2014 | Sugimoto et al. |
| 2014/0012369 A1 | 1/2014 | Murry, III et al. |
| 2014/0067037 A1 | 3/2014 | Fargahi |
| 2014/0094904 A1 | 4/2014 | Salahieh et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0194971 A1 | 7/2014 | McNamara |
| 2014/0213959 A1 | 7/2014 | Nitzan et al. |
| 2014/0222144 A1 | 8/2014 | Eberhardt et al. |
| 2014/0249621 A1 | 9/2014 | Eidenschink |
| 2014/0257167 A1 | 9/2014 | Celermajer |
| 2014/0275916 A1 | 9/2014 | Nabutovsky et al. |
| 2014/0277045 A1 | 9/2014 | Fazio et al. |
| 2014/0277054 A1 | 9/2014 | McNamara et al. |
| 2014/0303710 A1 | 10/2014 | Zhang et al. |
| 2014/0350565 A1* | 11/2014 | Yacoby ............... A61M 27/002 606/108 |
| 2014/0350658 A1 | 11/2014 | Benary et al. |
| 2014/0350661 A1 | 11/2014 | Schaeffer |
| 2014/0350669 A1 | 11/2014 | Gillespie et al. |
| 2014/0357946 A1 | 12/2014 | Golden et al. |
| 2015/0005810 A1 | 1/2015 | Center et al. |
| 2015/0034217 A1 | 2/2015 | Vad |
| 2015/0039084 A1 | 2/2015 | Levi et al. |
| 2015/0066140 A1 | 3/2015 | Quadri et al. |
| 2015/0073539 A1 | 3/2015 | Geiger et al. |
| 2015/0112383 A1 | 4/2015 | Sherman et al. |
| 2015/0119796 A1 | 4/2015 | Finch |
| 2015/0127093 A1 | 5/2015 | Hosmer et al. |
| 2015/0142049 A1 | 5/2015 | Delgado et al. |
| 2015/0148731 A1 | 5/2015 | McNamara et al. |
| 2015/0148896 A1 | 5/2015 | Karapetian et al. |
| 2015/0157455 A1 | 6/2015 | Hoang et al. |
| 2015/0173897 A1 | 6/2015 | Raanani et al. |
| 2015/0182334 A1 | 7/2015 | Bourang et al. |
| 2015/0190229 A1 | 7/2015 | Seguin |
| 2015/0196383 A1 | 7/2015 | Johnson |
| 2015/0201998 A1 | 7/2015 | Roy et al. |
| 2015/0209143 A1 | 7/2015 | Duffy et al. |
| 2015/0230924 A1 | 8/2015 | Miller et al. |
| 2015/0238314 A1 | 8/2015 | Bortlein et al. |
| 2015/0245908 A1 | 9/2015 | Nitzan et al. |
| 2015/0272731 A1 | 10/2015 | Racchini et al. |
| 2015/0282790 A1 | 10/2015 | Quinn et al. |

(56) References Cited

U.S. PATENT DOCUMENTS

| | | |
|---|---|---|
| 2015/0282931 A1 | 10/2015 | Brunnett et al. |
| 2015/0313599 A1 | 11/2015 | Johnson et al. |
| 2015/0359556 A1 | 12/2015 | Vardi |
| 2016/0007924 A1 | 1/2016 | Eigler et al. |
| 2016/0022423 A1 | 1/2016 | McNamara et al. |
| 2016/0022970 A1 | 1/2016 | Forcucci et al. |
| 2016/0073907 A1 | 3/2016 | Nabutovsky et al. |
| 2016/0120550 A1 | 5/2016 | McNamara et al. |
| 2016/0129260 A1 | 5/2016 | Mann et al. |
| 2016/0157862 A1 | 6/2016 | Hernandez et al. |
| 2016/0166381 A1 | 6/2016 | Sugimoto et al. |
| 2016/0184561 A9 | 6/2016 | McNamara et al. |
| 2016/0206423 A1 | 7/2016 | O'Connor et al. |
| 2016/0213467 A1 | 7/2016 | Backus et al. |
| 2016/0220360 A1 | 8/2016 | Lin et al. |
| 2016/0220365 A1 | 8/2016 | Backus et al. |
| 2016/0262878 A1 | 9/2016 | Backus et al. |
| 2016/0262879 A1 | 9/2016 | Meiri et al. |
| 2016/0287386 A1 | 10/2016 | Alon et al. |
| 2016/0296325 A1 | 10/2016 | Edelman et al. |
| 2016/0361167 A1 | 12/2016 | Tuval et al. |
| 2016/0361184 A1 | 12/2016 | Tabor et al. |
| 2017/0035435 A1 | 2/2017 | Amin et al. |
| 2017/0056171 A1* | 3/2017 | Cooper ............ A61M 25/0051 |
| 2017/0113026 A1 | 4/2017 | Finch |
| 2017/0128705 A1 | 5/2017 | Forcucci et al. |
| 2017/0135685 A9 | 5/2017 | McNamara et al. |
| 2017/0165532 A1 | 6/2017 | Khan et al. |
| 2017/0216025 A1 | 8/2017 | Nitzan et al. |
| 2017/0224323 A1 | 8/2017 | Rowe et al. |
| 2017/0224444 A1 | 8/2017 | Viecilli et al. |
| 2017/0231766 A1 | 8/2017 | Hariton et al. |
| 2017/0273790 A1 | 9/2017 | Vettukattil et al. |
| 2017/0281339 A1 | 10/2017 | Levi et al. |
| 2017/0312486 A1 | 11/2017 | Nitzan et al. |
| 2017/0319823 A1 | 11/2017 | Yacoby et al. |
| 2017/0325956 A1 | 11/2017 | Rottenberg et al. |
| 2017/0348100 A1* | 12/2017 | Lane .................... A61F 2/2409 |
| 2018/0099128 A9 | 4/2018 | McNamara et al. |
| 2018/0104053 A1 | 4/2018 | Alkhatib et al. |
| 2018/0125630 A1 | 5/2018 | Hynes et al. |
| 2018/0130988 A1 | 5/2018 | Nishikawa et al. |
| 2018/0243071 A1 | 8/2018 | Eigler et al. |
| 2018/0256865 A1 | 9/2018 | Finch et al. |
| 2018/0263766 A1 | 9/2018 | Nitzan et al. |
| 2018/0280667 A1 | 10/2018 | Keren |
| 2018/0344994 A1 | 12/2018 | Karavany et al. |
| 2019/0000327 A1 | 1/2019 | Doan et al. |
| 2019/0008628 A1 | 1/2019 | Eigler et al. |
| 2019/0015103 A1 | 1/2019 | Sharma |
| 2019/0015188 A1 | 1/2019 | Eigler et al. |
| 2019/0021861 A1 | 1/2019 | Finch |
| 2019/0239754 A1 | 8/2019 | Nabutovsky et al. |
| 2019/0254814 A1 | 8/2019 | Nitzan et al. |
| 2019/0262118 A1 | 8/2019 | Eigler et al. |
| 2019/0328513 A1 | 10/2019 | Levi et al. |
| 2019/0336163 A1 | 11/2019 | McNamara et al. |
| 2020/0060825 A1 | 2/2020 | Rottenberg et al. |
| 2020/0078558 A1 | 3/2020 | Yacoby et al. |
| 2020/0085600 A1 | 3/2020 | Schwartz et al. |
| 2020/0197178 A1 | 6/2020 | Vecchio |
| 2020/0261705 A1 | 8/2020 | Nitzan et al. |
| 2020/0315599 A1 | 10/2020 | Nae et al. |
| 2020/0368505 A1 | 11/2020 | Nae et al. |
| 2021/0052378 A1 | 2/2021 | Nitzan et al. |

FOREIGN PATENT DOCUMENTS

| | | | |
|---|---|---|---|
| EP | 1987777 A2 * | 11/2008 | ......... A61B 17/0057 |
| EP | 2238933 A1 | 10/2010 | |
| EP | 2305321 A1 | 4/2011 | |
| EP | 1965842 B1 | 11/2011 | |
| EP | 3400907 A1 | 11/2018 | |
| FR | 2827153 A1 | 1/2003 | |
| WO | WO-9531945 A1 | 11/1995 | |
| WO | WO-9727898 A1 | 8/1997 | |
| WO | WO-99/60941 A1 | 12/1999 | |
| WO | WO-00/44311 A2 | 8/2000 | |
| WO | WO-0050100 A1 | 8/2000 | |
| WO | WO-0110314 A2 | 2/2001 | |
| WO | WO-0226281 A1 | 4/2002 | |
| WO | WO-02/071974 A2 | 9/2002 | |
| WO | WO-02087473 A1 | 11/2002 | |
| WO | WO-03/053495 A2 | 7/2003 | |
| WO | WO-2005/027752 A1 | 3/2005 | |
| WO | WO-2005/074367 A1 | 8/2005 | |
| WO | WO-2006/127765 A1 | 11/2006 | |
| WO | WO-2007/083288 A2 | 7/2007 | |
| WO | WO-2008/055301 A1 | 5/2008 | |
| WO | WO-2009/029261 A1 | 3/2009 | |
| WO | WO-2010/128501 A1 | 11/2010 | |
| WO | WO-2010129089 A2 | 11/2010 | |
| WO | WO-2010139771 A2 * | 12/2010 | ......... A61B 17/0057 |
| WO | WO-2011062858 A1 | 5/2011 | |
| WO | WO-2013/096965 A1 | 6/2013 | |
| WO | WO-2016/178171 A1 | 11/2016 | |
| WO | WO-2017118920 A1 | 7/2017 | |
| WO | WO-2018158747 A1 | 9/2018 | |
| WO | WO-2019015617 A1 | 1/2019 | |
| WO | WO-2019085841 A1 | 5/2019 | |
| WO | WO-2019109013 A1 | 6/2019 | |
| WO | WO-2019142152 A1 | 7/2019 | |
| WO | WO-2019179447 A1 | 9/2019 | |
| WO | WO-2019218072 A1 | 11/2019 | |
| WO | WO-2020206062 A1 | 10/2020 | |
| WO | WO-2020257530 A1 | 12/2020 | |
| WO | WO-2021050589 A1 | 3/2021 | |
| WO | WO-2021113670 A1 | 6/2021 | |
| WO | WO-2021212011 A2 | 10/2021 | |
| WO | WO-2022046921 A1 | 3/2022 | |
| WO | WO-2022076601 A1 | 4/2022 | |

OTHER PUBLICATIONS

Atrium Advanta V12, Balloon Expandable Covered Stent, Improving Patient Outcomes with an Endovascular Approach, Brochure-8 pages, Getinge (2017).

Braunwald, Heart Disease, Chapter 6, p. 186.

Bridges, et al., The Society of Thoracic Surgeons Practice Guideline Series: Transmyocardial Laser Revascularization, Ann Thorac Surg., 77:1494-1502 (2004).

Bristow et al., Improvement in cardiac myocite function by biological effects of medical therapy: a new concept in the treatment of heart failure, European Heart Journal 16 (Suppl.F): 20-31 (1995).

Case et al., "Relief of High Left-Atrial Pressure in Left-Ventricular Failure," Lancet, pp. 841-842 (Oct. 14, 1964).

Coats et al., "Controlled trial of physical training in chronic heart failure: Exercise performance, hemodynamics, ventilation and autonomic function," Circulation 85:2119-2131 (1992).

Partial International Search dated Aug. 17, 2017 in Int'l PCT Patent Appl. Serial No. PCT/IB2017/053188.

Davies et al., "Reduced contraction and altered frequency response of isolated ventricular myocytes from patients with heart failure," Circulation 92: 2540-2549 (1995).

Ennezat et al., An unusual case of low-flow, low-gradient severe aortic stenosis: Left-to-right shunt due to atrial septal defect, Cardiology 113(2): 146-148 (2009).

Ewert et al., "Acute left heart failure after interventional occlusion of an atrial septal defect," Z Kardiol. 90(5): 362-366 (May 2001).

Ewert et al., Masked Left Ventricular Restriction in Elderly Patients With Atrial Septal Defects: A Contraindication for Closure?, Catheterization and Cardiovascular Interventions 52: 177-180 (2001).

Extended EP Search Report dated Sep. 19, 2016 in EP Patent Application Serial No. 16170281.6.

Extended European Search Report dated Jan. 8, 2015 in EP Patent Appl No. 10772089.8.

Geiran et al., "Changes in cardiac dynamics by opening an interventricular shunt in dogs," J. Surg. Res. 48(1): 6-12 (Jan. 1990).

Gelernter-Yaniv et al., "Transcatheter closure of left-to-right interatrial shunts to resolve hypoxemia," Conginit. Heart Dis. 31(1) 47-53 (Jan. 2008).

(56) References Cited

OTHER PUBLICATIONS

Gewillig et al., "Creation with a stent of an unrestrictive lasting atrial communication," Cardio. Young 12(4): 404-407 (2002).
International Search Report & Written Opinion dated May 29, 2018 in Int'l PCT Patent Appl. Serial No. PCTIB2018/051355.
International Search Report for PCT/IL2005/000131,3 pages (dated Apr. 7, 2008).
International Search Report for PCT/IL2010/000354 dated Aug. 25, 2010 (1 pg).
Int'l Search Report & Written Opinion dated Feb. 16, 2015 in Int'l PCT Patent Appl. Serial No. PCT/IB2014/001771.
Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).
Kramer et al., "Controlled study of captopril in chronic heart failure: A rest and exercise hemodynamic study," Circulation 67(4): 807-816 (1983).
Lai et al., Bidirectional Shunt Through a Residual Atrial Septal Defect After Percutaneous Transvenous Mitral Commissurotomy, Cardiology 83(3): 205-207 (1993).
Lemmer et al., "Surgical implications of atrial septal defect complicating aortic balloon valvuloplasty," Ann Thorac. Surg. 48(2): 295-297 (Aug. 1989).
Merriam-Webster "Definition of 'Chamber'," O-line Dictionary 2004, Abstract.
Park, et al., Blade Atrial Septostomy: Collaborative Study, Circulation, 66(2):258-266 (1982).
Roven et al., "Effect of Compromising Right Ventricular Function in Left Ventricular Failure by Means of Interatrial and Other Shunts," American Journal Cardiology, 24:209-219 (1969).
Salehian et al., Improvements in Cardiac Form and Function After Transcatheter Closure of Secundum Atrial Septal Defects, Journal of the American College of Cardiology, 45(4):499-504 (2005).
Schmitto et al., Chronic heart failure induced by multiple sequential coronary microembolization in sheep, The International Journal of Artificial Organs, 31(4):348-353 (2008).
Schubert et al., Left Ventricular Conditioning in the Elderly Patient to Prevent Congestive Heart Failure After Transcatheter Closure of the Atrial Septal Defect, Catheterization and Cardiovascular Interventions,64(3): 333-337 (2005).
Stormer et al., Comparative Study of n vitro Flow Characteristics Between a Human Aortic Valve and a Designed Aortic Valve and Six Corresponding Types of Prosthetic Heart Valves, European Surgical Research 8(2): 117-131 (1976).
Stumper et al., "Modified technique of stent fenestration of the atrial septum," Heart 89: 1227-1230 (2003).
Trainor et al., Comparative Pathology of an Implantable Left Atrial Pressure Sensor, ASAIO Journal, Clinical Cardiovascular/Cardiopulmonary Bypass, 59(5):486-92 (2013).
Zhou et al., Unidirectional Valve Patch for Repair of Cardiac Septal Defects With Pulmonary Hypertension, Annals of Thoracic Surgeons, 60:1245-1249 (1995).
Abraham et al., "Hemodynamic Monitoring in Advanced Heart Failure: Results from the LAPTOP-HF Trial," J Card Failure, 22:940 (2016) (Abstract Only).
Abraham et al., "Sustained efficacy of pulmonary artery pressure to guide adjustment of chronic heart failure therapy: complete follow-up results from the CHAMPION randomised trial," The Lancet, http://dx.doi.org/10.1016/S0140-6736(15)00723-0 (2015).
Abraham et al., "Wireless pulmonary artery haemodynamic monitoring in chronic heart failure: a randomised controlled trial," The Lancet, DOI:10.1016/S0140-6736(11)60101-3 (2011).
Abreu et al., "Doppler ultrasonography of the femoropopliteal segment in patients with venous ulcer," J Vasc Bras., 11(4):277-285 (2012).
Adamson et al., "Ongoing Right Ventricular Hemodynamics in Heart Failure Clinical Value of Measurements Derived From an Implantable Monitoring System," J Am Coll Cardiol., 41(4):565-571 (2003).

Adamson et al., "Wireless Pulmonary Artery Pressure Monitoring Guides Management to Reduce Decompensation in Heart Failure With Preserved Ejection Fraction," Circ Heart Fail., 7:935-944 (2014).
Ambrosy et al. "The Global Health and Economic Burden of Hospitalizations for Heart Failure," J Am Coll Cardiol., 63:1123-1133 (2014).
Aminde et al., "Current diagnostic and treatment strategies for Lutembacher syndrome: the pivotal role of echocardiography," Cardiovasc Diagn Ther., 5(2):122-132 (2015).
Anderas E. "Advanced MEMS Pressure Sensors Operating in Fluids," Digital Comprehensive Summaries of Uppsala Dissertation from the Faculty of Science and Technology 933. Uppsala ISBN 978-91-554-8369-2 (2012).
Anderas et al., "Tilted c-axis Thin-Film Bulk Wave Resonant Pressure Sensors with Improved Sensitivity," IEEE Sensors J., 12(8):2653-2654 (2012).
Article 34 Amendments dated May 28, 2013 in Int'l PCT Patent Appl. Serial No. PCT/IB2012/001859.
Article 34 Amendments dated Nov. 27, 2012 in Int'l PCT Patent Appl. Serial No. PCT/IL2011/000958.
Ataya et al., "A Review of Targeted Pulmonary Arterial Hypertension-Specific Pharmacotherapy," J. Clin. Med., 5(12):114(2016).
Bannan et al., "Characteristics of Adult Patients with Atrial Septal Defects Presenting with Paradoxical Embolism.," Catheterization and Cardiovascular Interventions, 74:1066-1069 (2009).
Baumgartner et al., "ESC Guidelines for the management of grown-up congenital heart disease (new version 2010)—The Task Force on the Management of Grown-up Congenital Heart Disease of the European Society of Cardiology (ESC)," Eur Heart J., 31:2915-2957 (2010).
Beemath et al., "Pulmonary Embolism as a Cause of Death in Adults Who Died With Heart Failure," Am J Cardiol., 98:1073-1075 (2006).
Benza et al., "Monitoring Pulmonary Arterial Hypertension Using an Implantable Hemodynamic Sensor," CHEST, 156(6):1176-1186 (2019).
Boehm, et al., "Balloon Atrial Septostomy: History and Technique," Images Paeditr. Cardiol., 8(1):8-14(2006).
Bruch et al., "Fenestrated Occluders for Treatment of ASD in Elderly Patients with Pulmonary Hypertension and/or Right Heart Failure," J Interven Cardiol., 21(1):44-49 (2008).
Burkhoff et al., "Assessment of systolic and diastolic ventricular properties via pressure-volume analysis: a guide for clinical, translational, and basic researchers," Am J Physiol Heart Circ Physiol., 289:H501-H512 (2005).
Butler et al. "Recognizing Worsening Chronic Heart Failure as an Entity and an End Point in Clinical Trials," JAMA., 312(8):789-790 (2014).
Chakko et al., "Clinical, radiographic, and hemodynamic correlations in chronic congestive heart failure: conflicting results may lead to inappropriate care," Am J Medicine, 90:353-359 (1991) (Abstract Only).
Chang et al., "State-of-the-art and recent developments in micro/nanoscale pressure sensors for smart wearable devices and health monitoring systems," Nanotechnology and Precision Engineering, 3:43-52 (2020).
Chen et al., "Continuous wireless pressure monitoring and mapping with ultra-small passive sensors for health monitoring and critical care," Nature Communications, 5(1):1-10 (2014).
Chen et al., "National and Regional Trends in Heart Failure Hospitalization and Mortality Rates for Medicare Beneficiaries, 1998-2008," JAMA, 306(15):1669-1678 (2011).
Chiche et al., "Prevalence of patent foramen ovale and stroke in pulmonary embolism patients," Eur Heart J., 34:P1142 (2013) (Abstract Only).
Chin et al., "The right ventricle in pulmonary hypertension," Coron Artery Dis., 16(1):13-18 (2005) (Abstract Only).
Chun et al., "Lifetime Analysis of Hospitalizations and Survival of Patients Newly Admitted With Heart Failure," Circ Heart Fail., 5:414-421 (2012).

(56) References Cited

OTHER PUBLICATIONS

Ciarka et al., "Atrial Septostomy Decreases Sympathetic Overactivity in Pulmonary Arterial Hypertension," Chest, 131(6):P1831-1837 (2007) (Abstract Only).
Cleland et al., "The EuroHeart Failure survey programme—a survey on the quality of care among patients with heart failure in Europe—Part 1: patient characteristics and diagnosis," Eur Heart J., 24:442-463 (2003).
Clowes et al., "Mechanisms of Arterial Graft Healing—Rapid Transmural Capillary Ingrowth Provides a Source of Intimal Endothelium and Smooth Muscle in Porous PTFE Prostheses," Am J Pathol., 123:220-230 (1986).
Davies et al., "Abnormal left heart function after operation for atrial septal defect," British Heart Journal, 32:747-753 (1970).
Del Trigo et al., "Unidirectional Left-to-Right Interatrial Shunting for Treatment of Patients with Heart Failure with Reduced Ejection Fraction: a Safety and Proof-of-Principle Cohort Study," Lancet, 387:1290-1297 (2016).
Della Lucia et al., "Design, fabrication and characterization of SAW pressure sensors for offshore oil and gas exploration," Sensors and Actuators A: Physical, 222:322-328 (2015).
Drazner et al., "Prognostic Importance of Elevated Jugular Venous Pressure and a Third Heart Sound in Patients with Heart Failure," N Engl J Med., 345(8):574-81 (2001).
Drazner et al., "Relationship between Right and Left-Sided Filling Pressures in 1000 Patients with Advanced Heart Failure," Heart Lung Transplant, 18:1126-1132 (1999).
Drexel, et al., "The Effects of Cold Work and Heat Treatment on the Properties of Nitinol Wire, Proceedings of the International Conference on Shape Memory and Superelastic Technologies, SMST 2006," Pacific Grove, California, USA (pp. 447-454) May 7-11, 2006.
Eigler et al., "Cardiac Unloading with an Implantable Interatrial Shunt in Heart Failure: Serial Observations in an Ovine Model of Ischemic Cardiomyopathy," Structural Heart, 1:40-48 (2017).
Eigler, et al., Implantation and Recovery of Temporary Metallic Stents in Canine Coronary Arteries, JACC, 22(4):1207-1213 (1993).
Eshaghian et al., "Relation of Loop Diuretic Dose to Mortality in Advanced Heart Failure," Am J Cardiol., 97:1759-1764 (2006).
Extended European Search Report dated Mar. 29, 2019 in EP Patent Appl. Serial No. EP16789391.
Feldman et al., "Transcatheter Interatrial Shunt Device for the Treatment of Heart Failure with Preserved Ejection Fraction (Reduce LAP-HF I [Reduce Elevated Left Atrial Pressure in Patients With Heart Failure]), A Phase 2, Randomized, Sham-Controlled Trial," Circulation, 137:364-375 (2018).
Ferrari et al., "Impact of pulmonary arterial hypertension (PAH) on the lives of patients and carers: results from an international survey," Eur Respir J., 42:26312 (2013) (Abstract Only).
Fonarow et al., "Characteristics, Treatments, and Outcomes of Patients With Preserved Systolic Function Hospitalized for Heart Failure," J Am Coll Cardiol., 50(8):768-777 (2007).
Fonarow et al., "Risk Stratification for in-Hospital Mortality in Acutely Decompensated Heart Failure: Classification and Regression Tree Analysis," JAMA, 293(5):572-580 (2005).
Fonarow, G., "The Treatment Targets in Acute Decompensated Heart Failure," Rev Cardiovasc Med., 2:(2):S7-S12 (2001).
Galie et al., "2015 ESC/ERS Guidelines for the diagnosis and treatment of pulmonary hypertension—The Joint Task Force for the Diagnosis and Treatment of Pulmonary Hypertension of the European Society of Cardiology (ESC) and the European Respiratory Society (ERS)," European Heart Journal, 37:67-119 (2016).
Galie et al., "Pulmonary arterial hypertension: from the kingdom of the near-dead to multiple clinical trial meta-analyses," Eur Heart J., 31:2080-2086 (2010).
Galipeau et al., "Surface acoustic wave microsensors and applications," Smart Materials and Structures, 6(6):658-667 (1997) (Abstract Only).
Geva et al., "Atrial septal defects," Lancet, 383:1921-32 (2014).

Gheorghiade et al., "Acute Heart Failure Syndromes, Current State and Framework for Future Research," Circulation, 112:3958-3968 (2005).
Gheorghiade et al., "Effects of Tolvaptan, a Vasopressin Antagonist, in Patients Hospitalized With Worsening Heart Failure a Randomized Controlled Trial," JAMA., 291:1963-1971 (2004).
Go et al. "Heart Disease and Stroke Statistics—2014 Update—A Report From the American Heart Association," Circulation, 128:1-267 (2014).
Guillevin et al., "Understanding the impact of pulmonary arterial hypertension on patients' and carers' lives," Eur Respir Rev., 22:535-542 (2013).
Guyton et al., "Effect of Elevated Left Atrial Pressure and Decreased Plasma Protein Concentration on the Development of Pulmonary Edema," Circulation Research, 7:643-657 (1959).
Hasenfub, et al., A Transcatheter Intracardiac Shunt Device for Heart Failure with Preserved Ejection Fraction (Reduce LAP-HF): A Multicentre, Open-Label, Single-Arm, Phase 1 Trial, www.thelancet.com, 387:1298-1304 (2016).
Hoeper et al., "Definitions and Diagnosis of Pulmonary Hypertension," J Am Coll Cardiol., 62(5):D42-D50 (2013).
Hogg et al., "Heart Failure With Preserved Left Ventricular Systolic Function. Epidemiology, Clinical Characteristics, and Prognosis," J Am Coll Cardiol., 43(3):317-327 (2004).
Howell et al., "Congestive heart failure and outpatient risk of venous thromboembolism: A retrospective, case-control study," Journal of Clinical Epidemiology, 54:810-816 (2001).
Huang et al., "Remodeling of the chronic severely failing ischemic sheep heart after coronary microembolization: functional, energetic, structural, and cellular responses," Am J Physiol Heart Circ Physiol., 286:H2141-H2150 (2004).
Humbert et al., "Pulmonary Arterial Hypertension in France—Results from a National Registry," Am J Respir Crit Care Med., 173:1023-1030 (2006).
International Search Report & Written Opinion dated May 29, 2018 in Int'l PCT Patent Appl. Serial No. PCI/IB2018/051355.
International Search Report & Written Opinion dated Feb. 6, 2013 in Int'l PCT Patent Appl. No. PCT/IB2012/001859, 12 pages.
International Search Report & Written Opinion dated Feb. 7, 2020 in Int'l PCT Patent Appl. Serial No. PCT/IB2019/060257.
International Search Report & Written Opinion dated May 13, 2019 in Int'l PCT Patent Appl. No. PCT/IB2019/050452.
International Search Report & Written Opinion dated Jul. 14, 2020 in Int'l PCT Patent Appl. Serial No. PCT/IB2020/053832.
International Search Report & Written Opinion dated Jul. 20, 2020 in Int'l PCT Patent Appl. Serial No. PCT/IB2020/054699.
International Search Report & Written Opinion dated Aug. 12, 2020 in Int'l PCT Patent Appl. Serial No. PCT/IB2020/053118.
International Search Report & Written Opinion dated Aug. 28, 2012 in Int'l PCT Patent Appl. No. PCT/IL2011/000958.
International Search Report & Written Opinion dated Sep. 21, 2020 in Int'l PCT Patent Appl. Serial No. PCT/IB2020/054306.
International Search Report & Written Opinion dated Oct. 26, 2007 in Int'l PCT Patent Appl. Serial No. PCT/IB07/50234.
Jessup et al. "2009Focused Update: ACC/AHA Guidelines for the Diagnosisand Management of Heart Failure in Adults: A Report of the American College ofCardiology Foundation/American Heart Association Task Force on PracticeGuidelines: Developed in Collaboration With the International Society for Heartand Lung Transplantation," J. Am. Coll. Cardiol., 53:1343-1382 (2009).
Jiang, G., "Design challenges of implantable pressure monitoring system," Frontiers in Neuroscience, 4(29):1-4 (2010).
Kane et al., "Integration of clinical and hemodynamic parameters in the prediction of long-term survival in patients with pulmonary arterial hypertension," Chest, 139(6):1285-1293 (2011) (Abstract Only).
Kaye et al., "Effects of an Interatrial Shunt on Rest and Exercise Hemodynamics: Results of a Computer Simulation in Heart Failure," Journal of Cardiac Failure, 20(3): 212-221 (2014).
Kaye et al., "One-Year Outcomes After Transcatheter Insertion of an Interatrial Shunt Device for the Management of Heart Failure With Preserved Ejection Fraction," Circulation: Heart Failure, 9(12):e003662 (2016).

(56) References Cited

OTHER PUBLICATIONS

Keogh et al., "Interventional and Surgical Modalitiesof Treatment in Pulmonary Hypertension," J Am Coll Cardiol., 54:S67-77 (2009).
Kretschmar et al., "Shunt Reduction With a Fenestrated Amplatzer Device," Catheterization and Cardiovascular Interventions, 76:564-571 (2010).
Kropelnicki et al., "CMOS-compatible ruggedized high-temperature Lamb wave pressure sensor," J. Micromech. Microeng., 23:085018 pp. 1-9 (2013).
Krumholz et al., "Patterns of Hospital Performance in Acute Myocardial Infarction and Heart Failure 30-Day Mortality and Readmission," Circ Cardiovasc Qual Outcomes, 2:407-413 (2009).
Kulkarni et al., "Lutembacher's syndrome," J Cardiovasc Did Res., 3(2):179-181 (2012).
Kurzyna et al., "Atrial Septostomy in Treatment of End-Stage Right Heart Failure in Patients With Pulmonary Hypertension," Chest, 131:977-983 (2007).
Lammers et al., "Efficacy and Long-Term Patency of Fenerstrated Amplatzer Devices in Children," Catheter Cardiovasc Interv., 70:578-584 (2007).
Lindenfeld et al. "Executive Summary: HFSA 2010 Comprehensive Heart Failure Practice Guideline," J. Cardiac Failure, 16(6):475-539 (2010).
Luo, Yi,*Selective and Regulated RF Heating of Stent Toward Endohyperthermia Treatment of In-Stent Restenosis*, A Thesis Submitted in Partial Fulfillment of the Requirements for the Degree of Master of Applied Science in the Faculty of Graduate and Postdoctoral Studies (Electrical and Computer Engineering), The University of British Columbia, Vancouver, Dec. 2014.
MacDonald et al., "Emboli Enter Penetrating Arteries of Monkey Brain in Relation to Their Size," Stroke, 26:1247-1251 (1995).
Maluli et al., "Atrial Septostomy: A Contemporary Review," Clin. Cardiol., 38(6):395-400 (2015).
Maurer et al., "Rationale and Design of the Left Atrial Pressure Monitoring to Optimize Heart Failure Therapy Study (LAPTOP-HF)," Journal of Cardiac Failure., 21(6): 479-488 (2015).
McClean et al., "Noninvasive Calibration of Cardiac Pressure Transducers in Patients With Heart Failure: An Aid to Implantable Hemodynamic Monitoring and Therapeutic Guidance," J Cardiac Failure, 12(7):568-576 (2006).
McLaughlin et al., "Management of Pulmonary Arterial Hypertension," J Am Coll Cardiol., 65(18):1976-1997 (2015).
McLaughlin et al., "Survival in Primary Pulmonary Hypertension—The Impact of Epoprostenol Therapy.," Circulation, 106:1477-1482 (2002).
Mu et al., "Dual mode acoustic wave sensor for precise pressure reading," Applied Physics Letters, 105:113507-1—113507-5 (2014).
Nagaragu et al., "A 400μW Differential FBAR Sensor Interface IC with digital readout," IEEE., pp. 218-221 (2015).
Noordegraaf et al., "The role of the right ventricle in pulmonary arterial hypertension," Eur Respir Rev., 20(122):243-253 (2011).
O'Byrne et al., "The effect of atrial septostomy on the concentration of brain-type natriuretic peptide in patients with idiopathic pulmonary arterial hypertension," Cardiology in the Young, 17(5):557-559 (2007) (Abstract Only).
Oktay et al., "The Emerging Epidemic of Heart Failure with Preserved Ejection Fraction," Curr Heart Fail Rep., 10(4):1-17 (2013).
Owan et al., "Trends in Prevalence and Outcome of Heart Failure with Preserved Ejection Fraction," N Engl J Med., 355:251-259 (2006).
Paitazoglou et al., "Title: The AFR-Prelieve Trial: A prospective, non-randomized, pilot study to assess the Atrial Flow Regulator (AFR) in Heart Failure Patients with either preserved or reduced ejection fraction," EuroIntervention, 28:2539-50 (2019).
Park Blade Septostomy Catheter Instructions for Use, Cook Medical, 28 pages, Oct. 2015.
Partial Supplemental European Search Report dated Dec. 11, 2018 in EP Patent Appl. Serial No. 16789391.6.
Peters et al., "Self-fabricated fenestrated Amplatzer occluders for transcatheter closure of atrial septal defect in patients with left ventricular restriction: midterm results," Clin Res Cardiol., 95:88-92 (2006).
Ponikowski et al., "2016 ESC Guidelines for the diagnosis and treatment of acute and chronic heart failure. The Task Force for the diagnosis and treatment of acute and chronic heart failure of the European Society of Cardiology (ESC)," Eur Heart J., doi:10.1093/eurheartj/ehw128 (2016).
Potkay, J. A., "Long term, implantable blood pressure monitoring systems," Biomed Microdevices, 10:379-392 (2008).
Pretorious et al., "An Implantable Left Atrial Pressure Sensor Lead Designed for Percutaneous Extraction Using Standard Techniques," PACE, 00:1-8 (2013).
Rajeshkumar et al., "Atrial septostomy with a predefined diameter using a novel occlutech atrial flow regulator improves symptoms and cardiac index in patients with severe pulmonary arterial hypertension," Catheter Cardiovasc Interv., 1-9 (2017).
Rich et al., "Atrial Septostomy as Palliative Therapy for Refractory Primary Pulmonary Hypertension," Am J Cardiol., 51:1560-1561 (1983).
Ritzema et al., "Direct Left Atrial Pressure Monitoring in Ambulatory Heart Failure Patients—Initial Experience With a New Permanent Implantable Device," Circulation, 116:2952-2959 (2007).
Ritzema et al., "Physician-Directed Patient Self-Management of Left Atrial Pressure in Advanced Chronic Heart Failure," Circulation, 121:1086-1095 (2010).
Roberts et al., "Integrated microscopy techniques for comprehensive pathology evaluation of an implantable left atrial pressure sensor," J Histotechnology, 36(1):17-24 (2013).
Rodes-Cabau et al., "Interatrial Shunting for Heart Failure Early and Late Results From the First-in-Human Experience With the V-Wave System," J Am Coll Cardiol Intv., 11:2300-2310.doi:10.1016/j.cin.2018.07.001 (2018).
Rosenquist et al., Atrial Septal Thickness and Area in Normal Heart Specimens and in Those With Ostium Secundum Atrial Septal Defects, J. Clin. Ultrasound, 7:345-348 (1979).
Ross et al., "Interatrial Communication and Left Atrial Hypertension—A Cause of Continuous Murmur," Circulation, 28:853-860 (1963).
Rossignol, et al., Left-to-Right Atrial Shunting: New Hope for Heart Failure, www.thelancet.com, 387:1253-1255 (2016).
Sandoval et al., "Effect of atrial septostomy on the survival of patients with severe pulmonary arterial hypertension," Eur Respir J., 38:1343-1348 (2011).
Sandoval et al., "Graded Balloon Dilation Atrial Septostomy in Severe Primary Pulmonary Hypertension—A Therapeutic Alternative for Patients Nonresponsive to Vasodilator Treatment," JACC, 32(2):297-304 (1998).
Schiff et al., "Decompensated heart failure: symptoms, patterns of onset, and contributing factors," Am J. Med., 114(8):625-630 (2003) (Abstract Only).
Schneider et al., "Fate of a Modified Fenestration of Atrial Septal Occluder Device after Transcatheter Closure of Atrial Septal Defects in Elderly Patients," J Interven Cardiol., 24:485-490 (2011).
Scholl et al., "Surface Acoustic Wave Devices for Sensor Applications," Phys Status Solidi Appl Res., 185(1):47-58 (2001) (Abstract Only).
Setoguchi et al., "Repeated hospitalizations predict mortality in the community population with heart failure," Am Heart J., 154:260-266 (2007).
Shah et al., "Heart Failure With Preserved, Borderline, and Reduced Ejection Fraction—5-Year Outcomes," J Am Coll Cardiol., https://doi.org/10.1016/j.jacc.2017.08.074 (2017).
Shah et al., "One-Year Safety and Clinical Outcomes of a Transcatheter Interatrial Shunt Device for the Treatment of Heart Failure With Preserved Ejection Fraction in the Reduce Elevated Left Atrial Pressure in Patients With Heart Failure (Reduce LAP-HF I) Trial—A Randomized Clinical Trial," JAMA Cardiol. doi:10.1001/jamacardio.2018.2936 (2018).
Sitbon et al., "Selexipag for the Treatment of Pulmonary Arterial Hypertension.," N Engl J Med., 373(26):2522-2533 (2015).

(56) References Cited

OTHER PUBLICATIONS

Sitbon et al., "Epoprostenol and pulmonary arterial hypertension: 20 years of clinical experience," Eur Respir Rev., 26:160055:1-14 (2017).
Steimle et al., "Sustained Hemodynamic Efficacy of Therapy Tailored to Reduce Filling Pressures in Survivors With Advanced Heart Failure," Circulation, 96:1165-1172 (1997).
Stevenson et al., "The Limited Reliability of Physical Signs for Estimating Hemodynamics in Chronic Heart Failure," JAMA, 261(6):884-888 (1989) (Abstract Only).
Su et al., "A film bulk acoustic resonator pressure sensor based on lateral field excitation," International Journal of DistributedSensor Networks, 14(11):1-8 (2018).
Supplementary European Search Report dated Nov. 13, 2009 in EP Patent Appl. Serial No. 05703174.2.
Thenappan et al., "Evolving Epidemiology of Pulmonary Arterial Hypertension," Am J Resp Critical Care Med., 186:707-709 (2012).
Tomai et al., "Acute Left Ventricular Failure After Transcatheter Closure of a Secundum Atrial Septal Defect in a Patient With Coronary Artery Disease: A Critical Reappraisal," Catheterization and Cardiovascular Interventions, 55:97-99 (2002).
Torbicki et al., "Atrial Septostomy," The Right Heart, 305-316 (2014).
Troost et al., "A Modified Technique of Stent Fenestration of the Interatrial Septum Improves Patients With Pulmonary Hypertension," Catheterization and Cardiovascular Interventions, 73:173179 (2009).
Troughton et al., "Direct Left Atrial Pressure Monitoring in Severe Heart Failure: Long-Term Sensor Performance," J. of Cardiovasc. Trans. Res., 4:3-13 (2011).
Vank-Noordegraaf et al., "Right Heart Adaptation to Pulmonary Arterial Hypertension—Physiology and Pathobiology," J Am Coll Cardiol., 62(25):D22-33 (2013).
Verel et al., "Comparison of left atrial pressure and wedge pulmonary capillary pressure—Pressure gradients between left atrium and left ventricle," British Heart J., 32:99-102 (1970).
Viaene et al., "Pulmonary oedema after percutaneous ASD-closure," Acta Cardiol., 65(2):257-260 (2010).
Wang et al., "A Low Temperature Drifting Acoustic Wave Pressure Sensor with an Integrated Vacuum Cavity for Absolute Pressure Sensing," Sensors, 20(1788):1-13 (2020).
Warnes et al., "ACC/AHA 2008 Guidelines for the Management of Adults With Congenital Heart Disease—A Report of the American College of Cardiology/American Heart Association Task Force on Practice Guidelines (Writing Committee to Develop Guidelines on the Management of Adults With Congenital Heart Disease)," JACC, 52(23):e143-e263 (2008).
Webb et al., "Atrial Septal Defects in the Adult Recent Progress and Overview," Circulation, 114:1645-1653 (2006).
Wiedemann, H.R., "Earliest description by Johann Friedrich Meckel, Senior (1750) of what is known today as Lutembacher syndrome (1916)," Am J Med Genet., 53(1):59-64 (1994) (Abstract Only).
Written Opinion of the International Searching Authority dated Apr. 7, 2008 in Int'l PCT Patent Appl. Serial No. PCT/IL05/00131.
Yantchev et al., "Thin Film Lamb Wave Resonators in Frequency Control and Sensing Applications: A Review," Journal of Micromechanics and Microengineering, 23(4):043001 (2013).
Zhang et al., "Acute left ventricular failure after transcatheter closure of a secundum atrial septal defect in a patient with hypertrophic cardiomyopathy," Chin Med J., 124(4):618-621 (2011).
Zhang et al., "Film bulk acoustic resonator-based high-performance pressure sensor integrated with temperature control system," J Micromech Microeng., 27(4):1-10 (2017).
Borlaug, et al., Latent Pulmonary Vascular Disease May Alter the Response to Therapeutic Atrial Shunt Device in Heart Failure, Circulation (Mar. 2022).
Flachskampf, et al., Influence of Orifice Geometry and Flow Rate on Effective Valve Area: An In Vitro Study, Journal of the American College of Cardiology, 15(5):1173-1180 (Apr. 1990).
International Search Report & Written Opinion dated Nov. 7, 2016 in Int'l PCT Patent Appl. Serial No. PCT/IB2016/052561.
International Search Report & Written Opinion dated Feb. 9, 2022 in Int'l PCT Patent Appl. Serial No. PCT/IB2021/060473 (2010).
International Search Report & Written Opinion dated May 17, 2022 in Int'l PCT Patent Appl. Serial No. PCT/IB2022/051177.
International Search Report & Written Opinion dated Jul. 23, 2021 in Int'l PCT Patent Appl. Serial No. PCT/IB2021/053594.
Kaye, et al., One-Year Outcomes After Transcatheter Insertion of an Interatrial Shunt Device for the Management of Heart Failure with Preserved Ejection Fraction, Circulation: Heart Failure, 9(12):e003662 (Dec. 2016).
Shah, et al., Atrial Shunt Device for Heart Failure With Preserved and Mildly Reduced Ejection Fraction (Reduce LAP-HF II): A Randomised, Multicentre, Blinded, Sham-Controlled Trial, The Lancet, 399(10330):1130-1140 (Mar. 2022).

\* cited by examiner

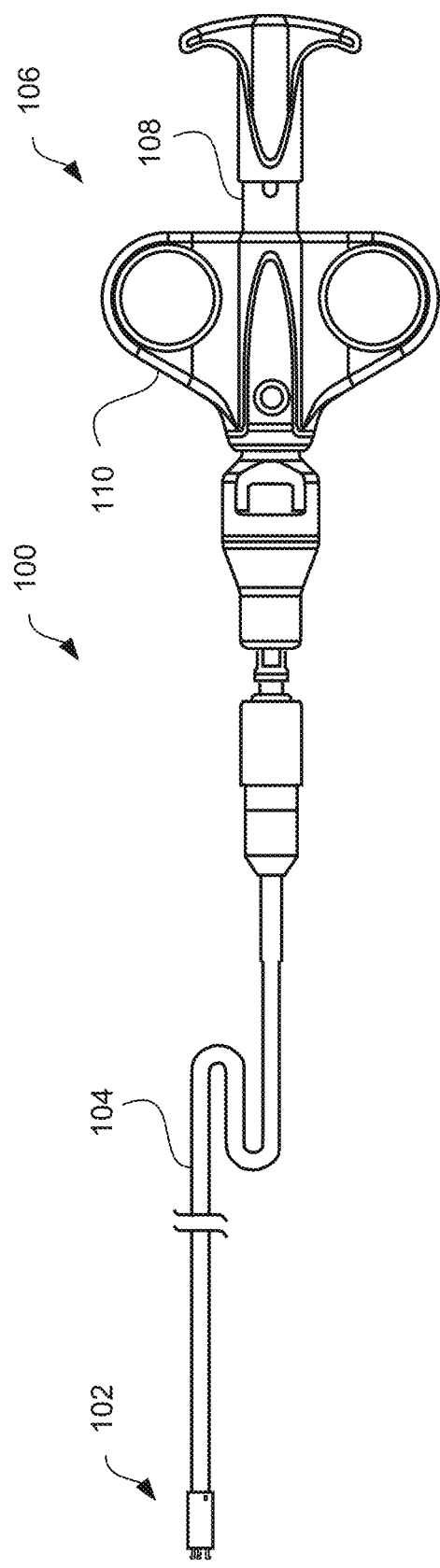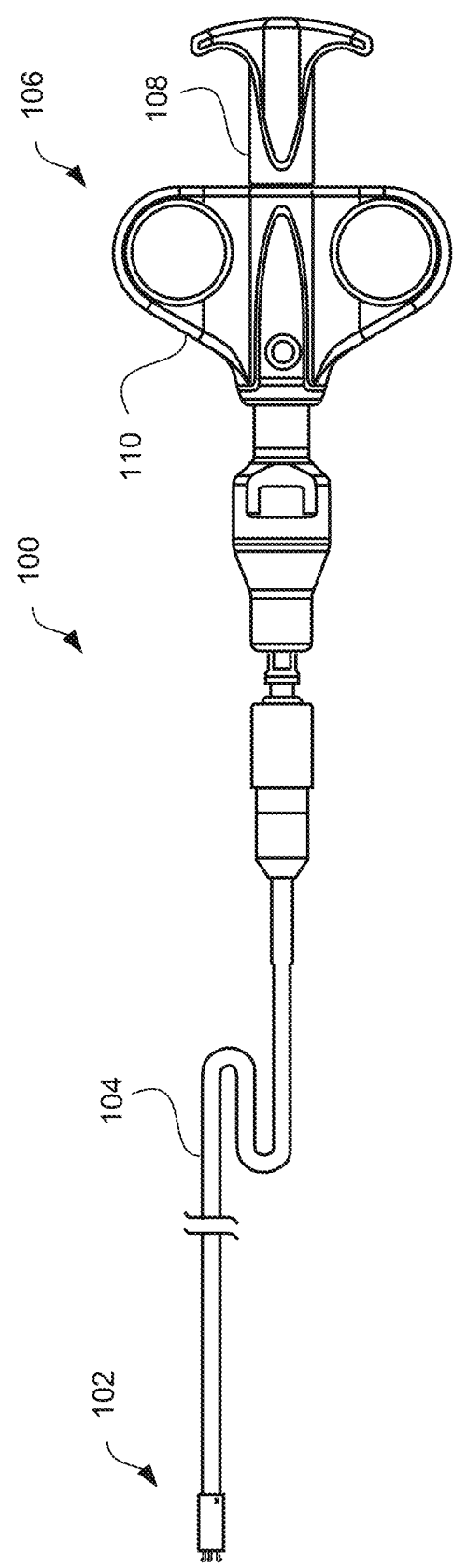
FIG. 1A
FIG. 1B

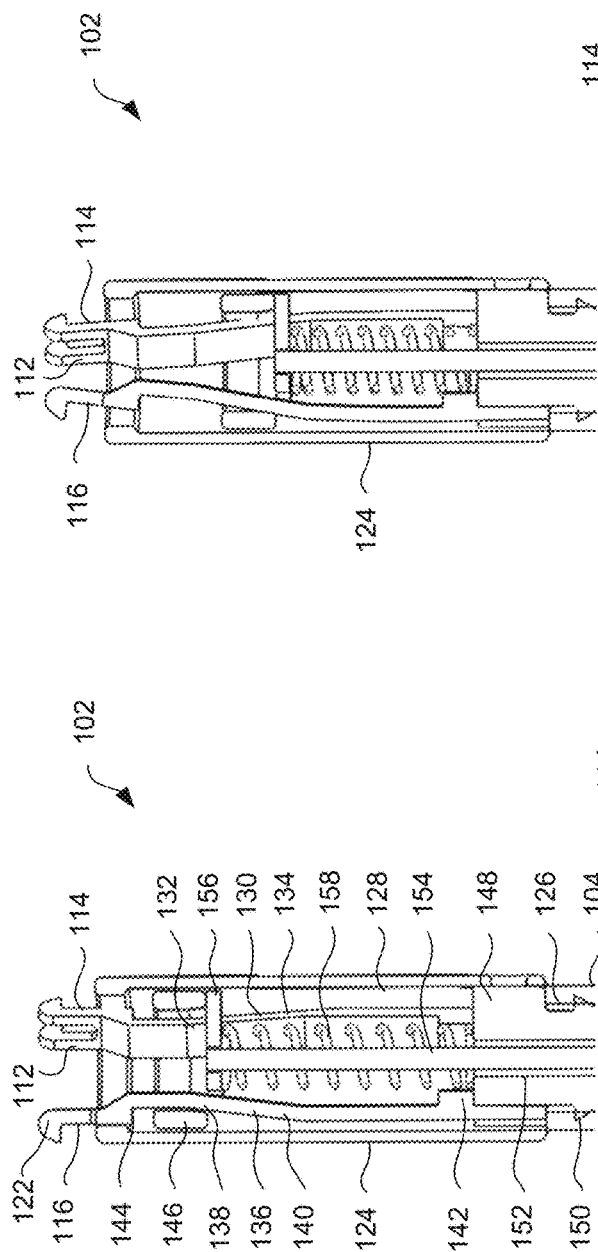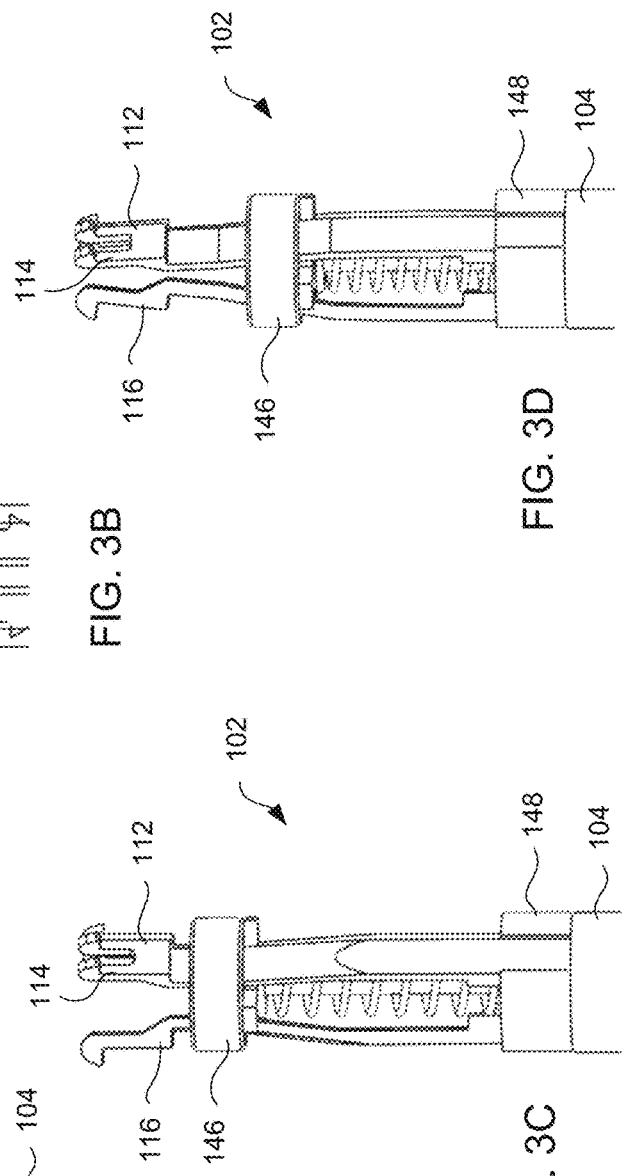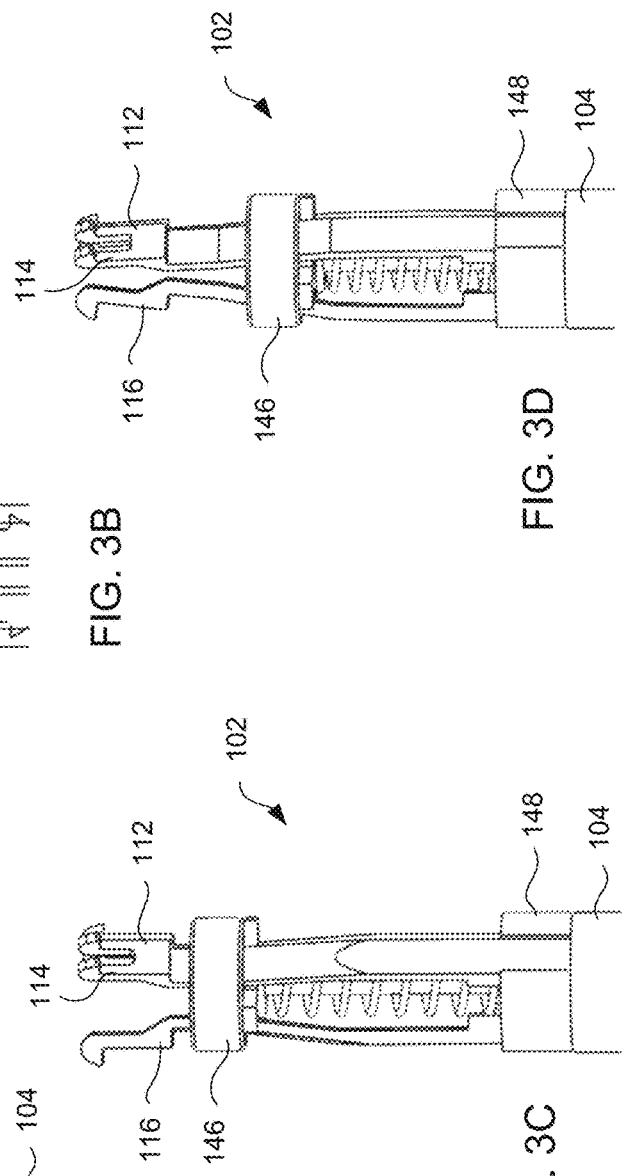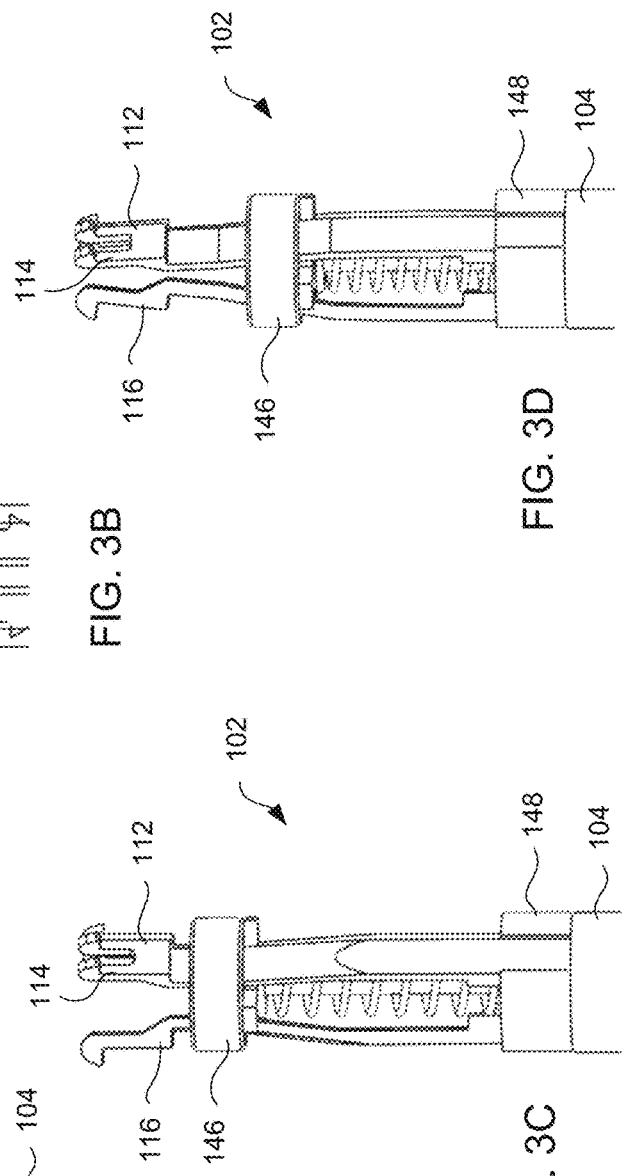

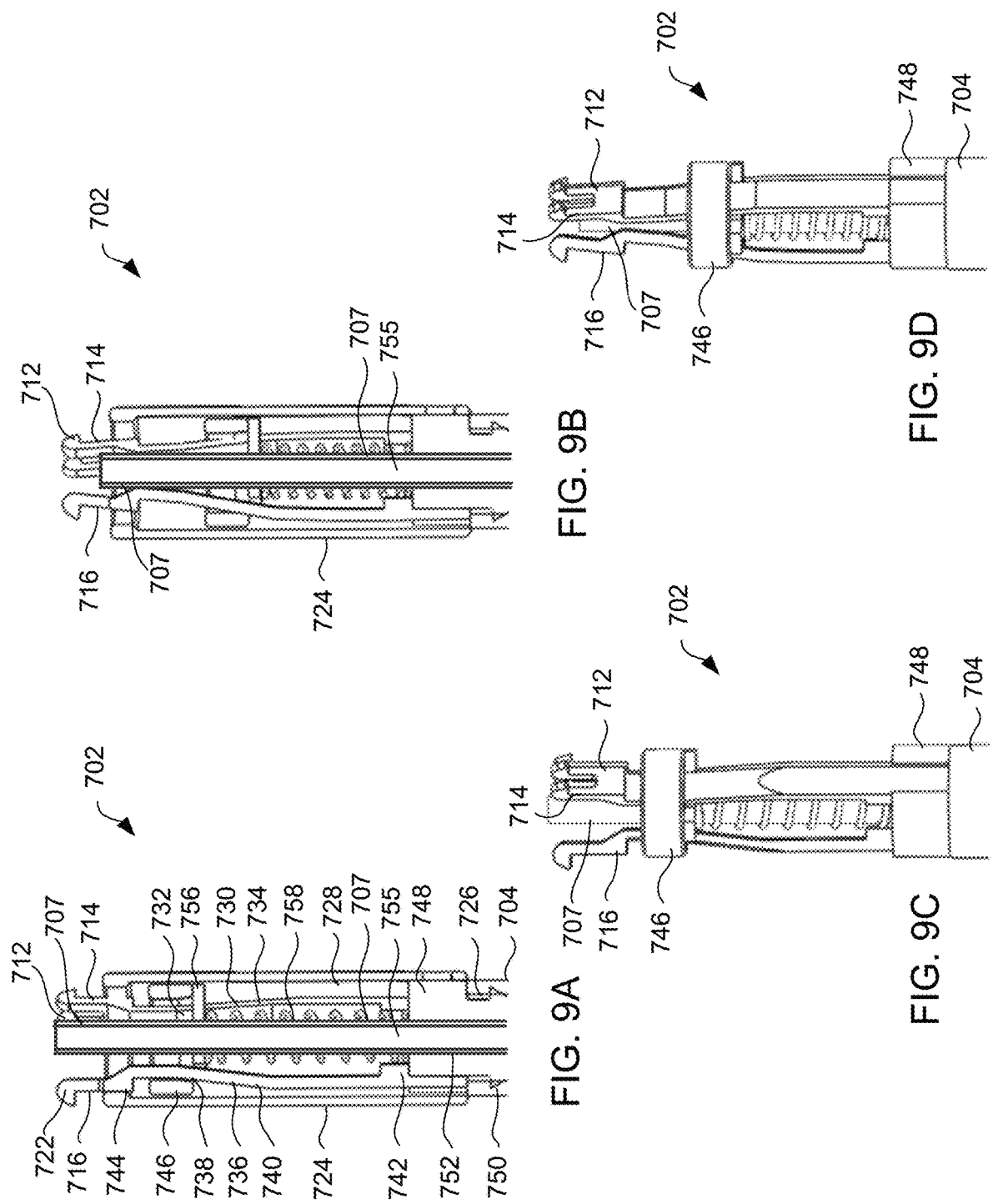

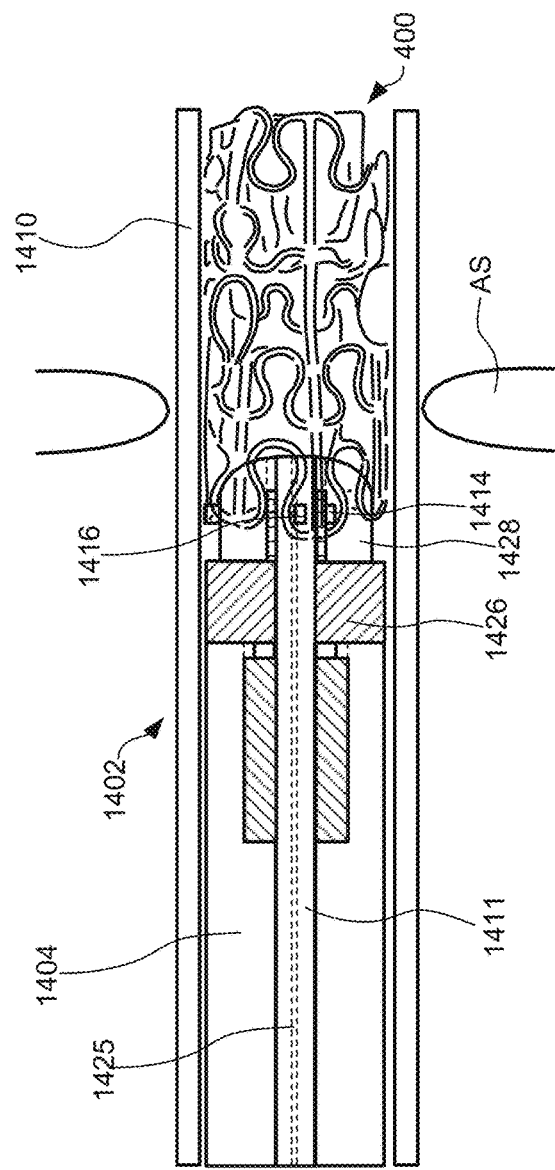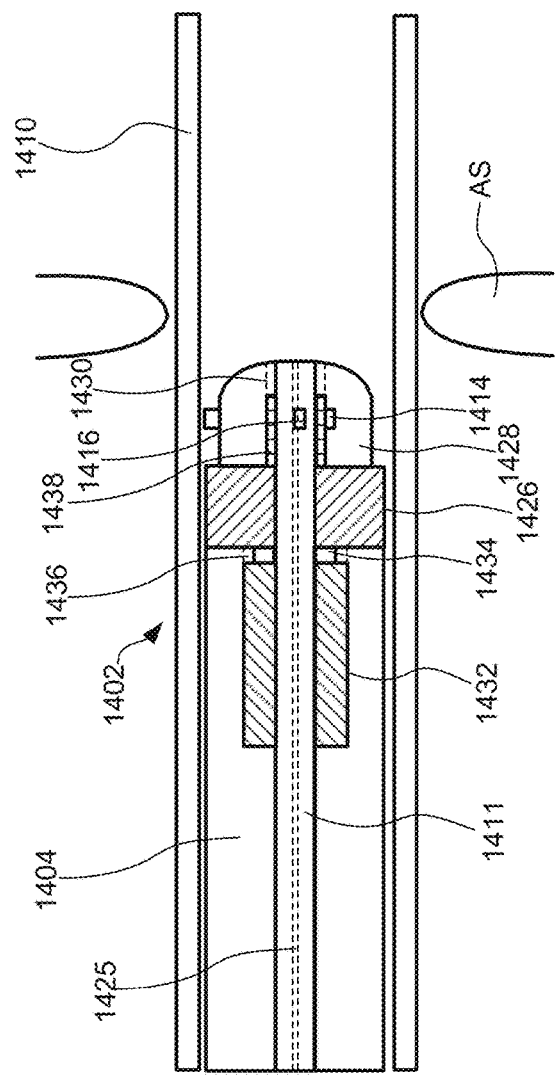

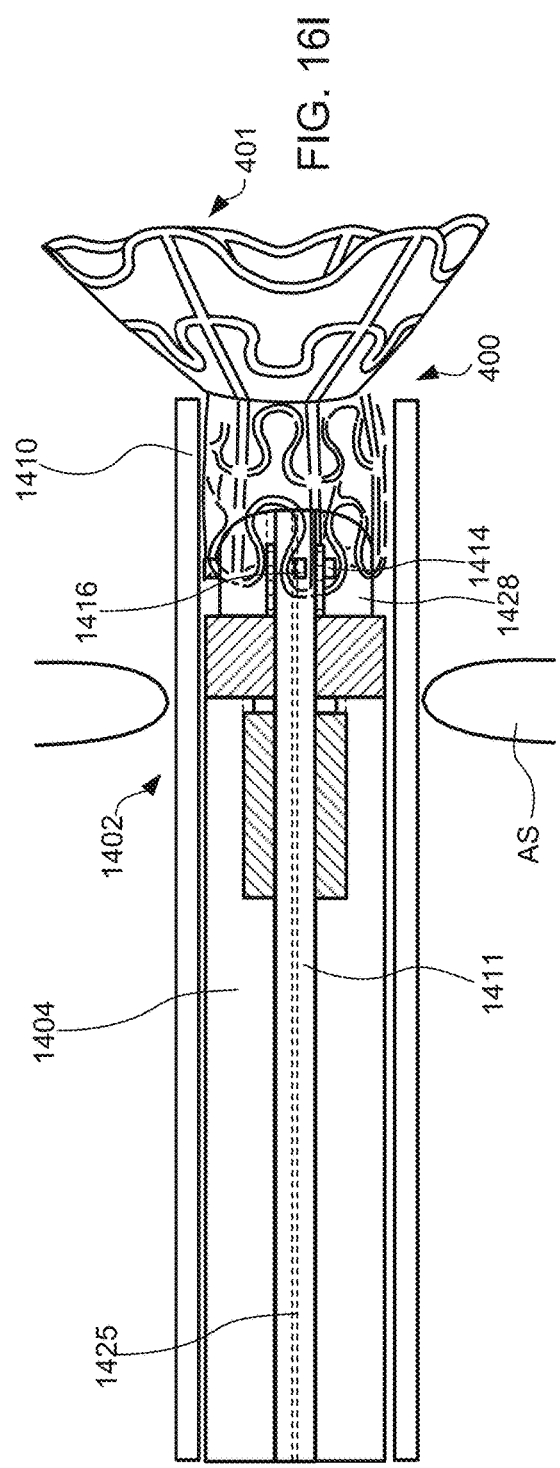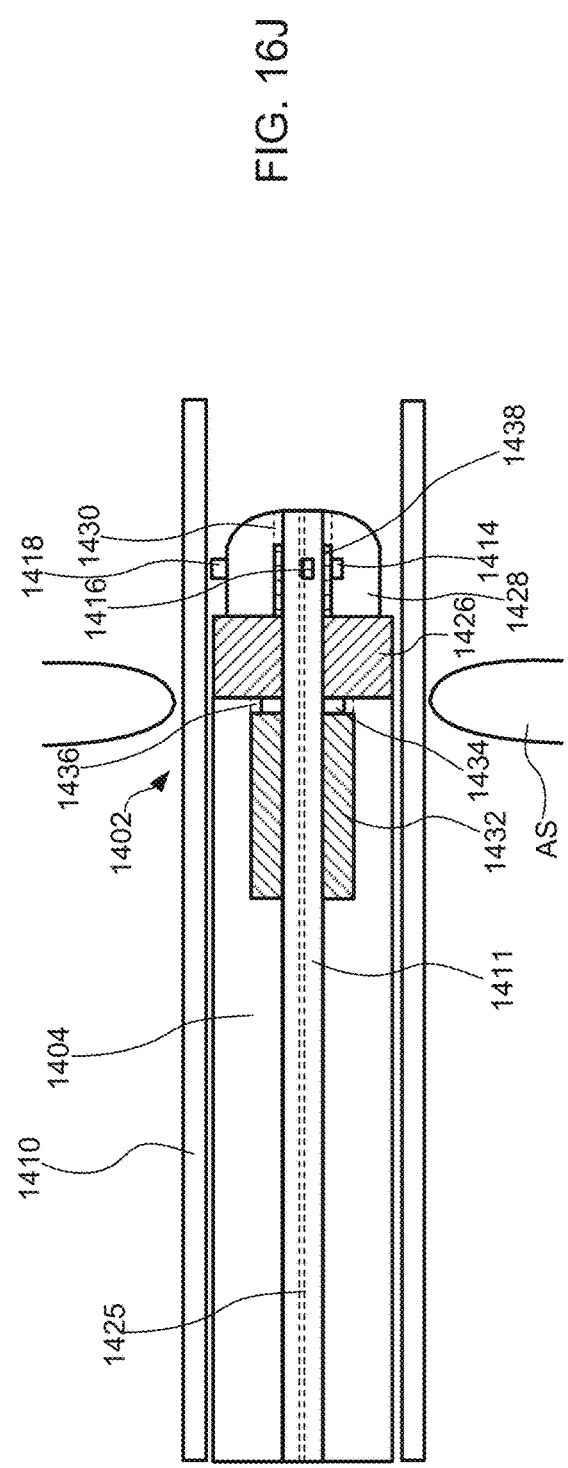

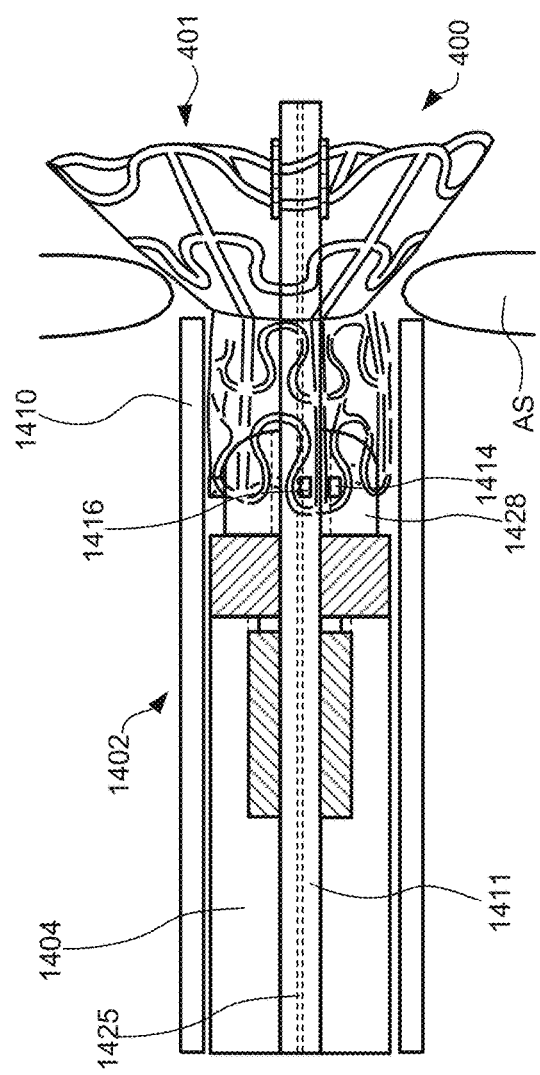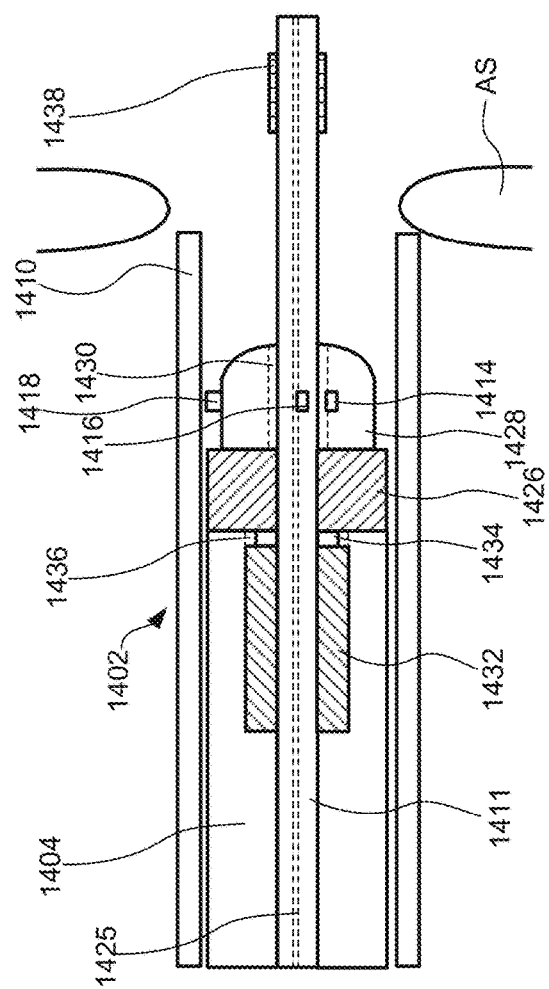

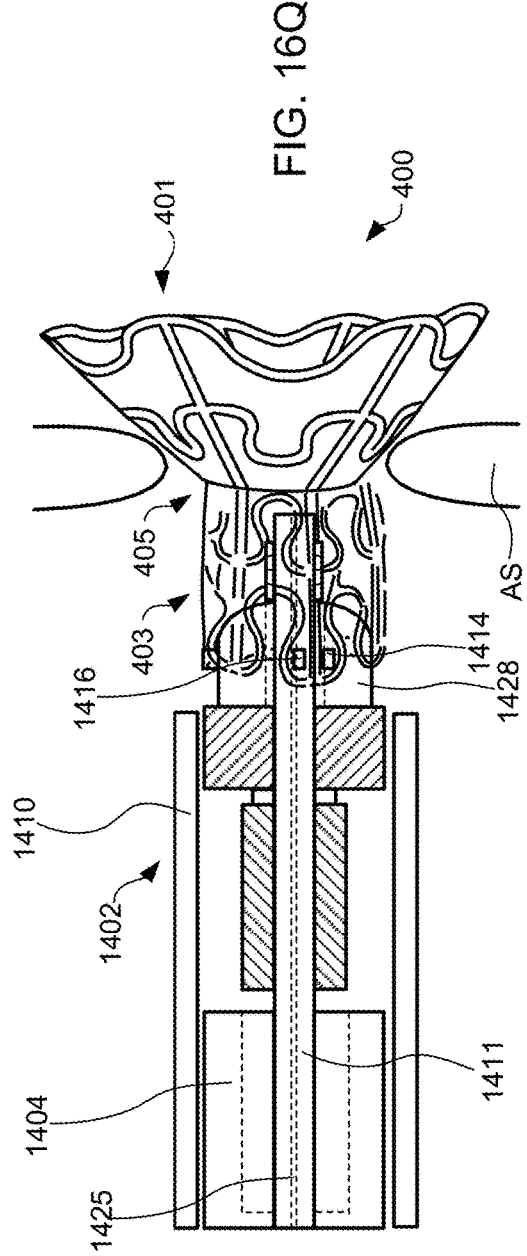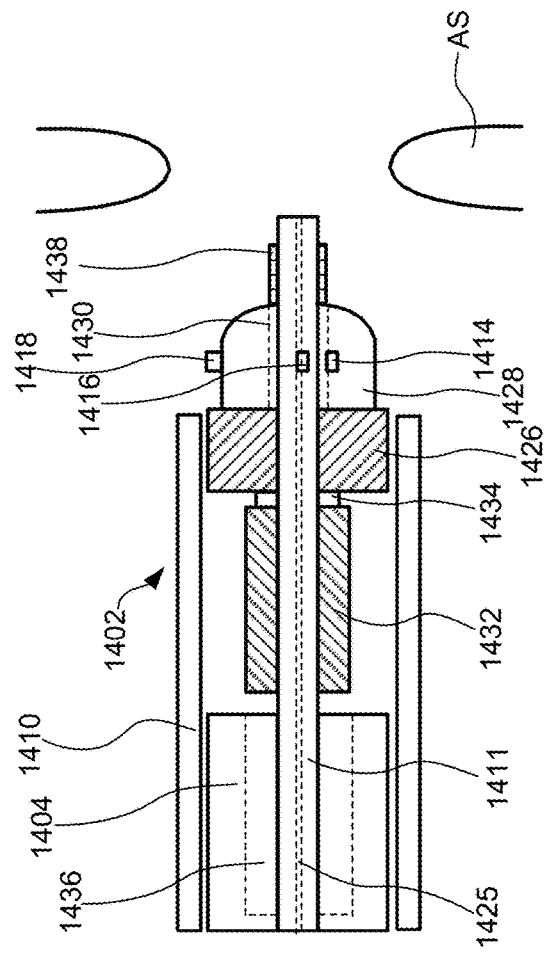

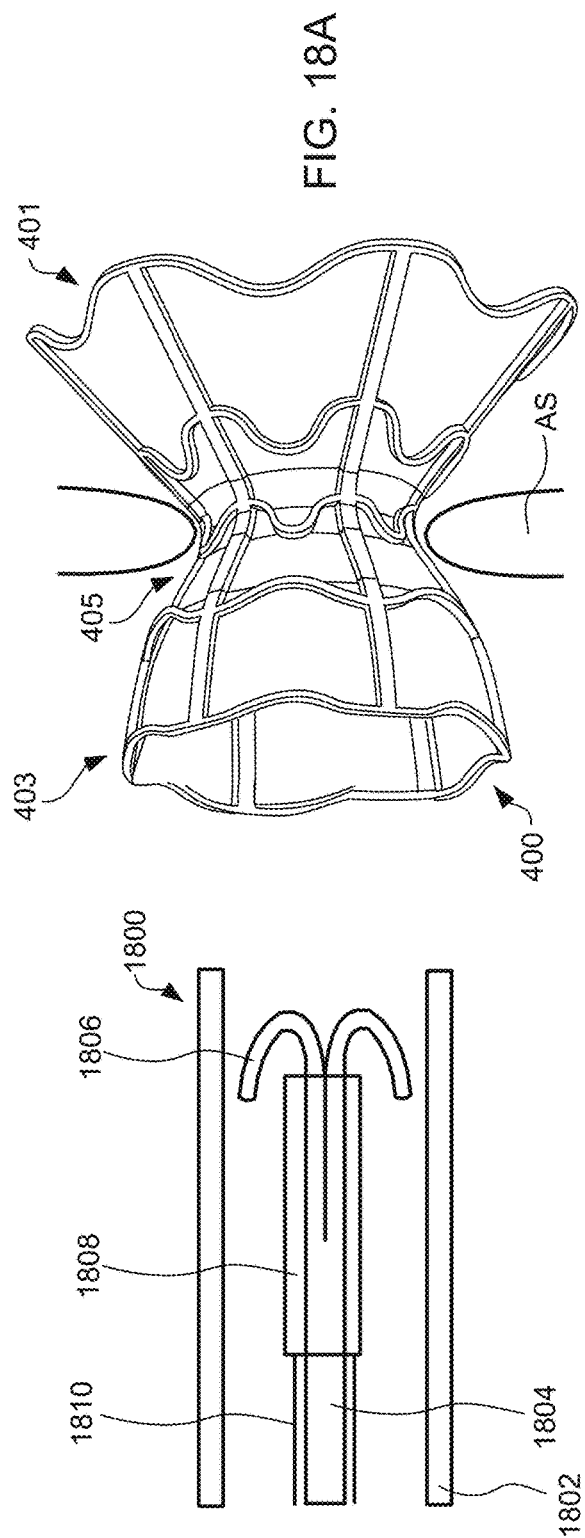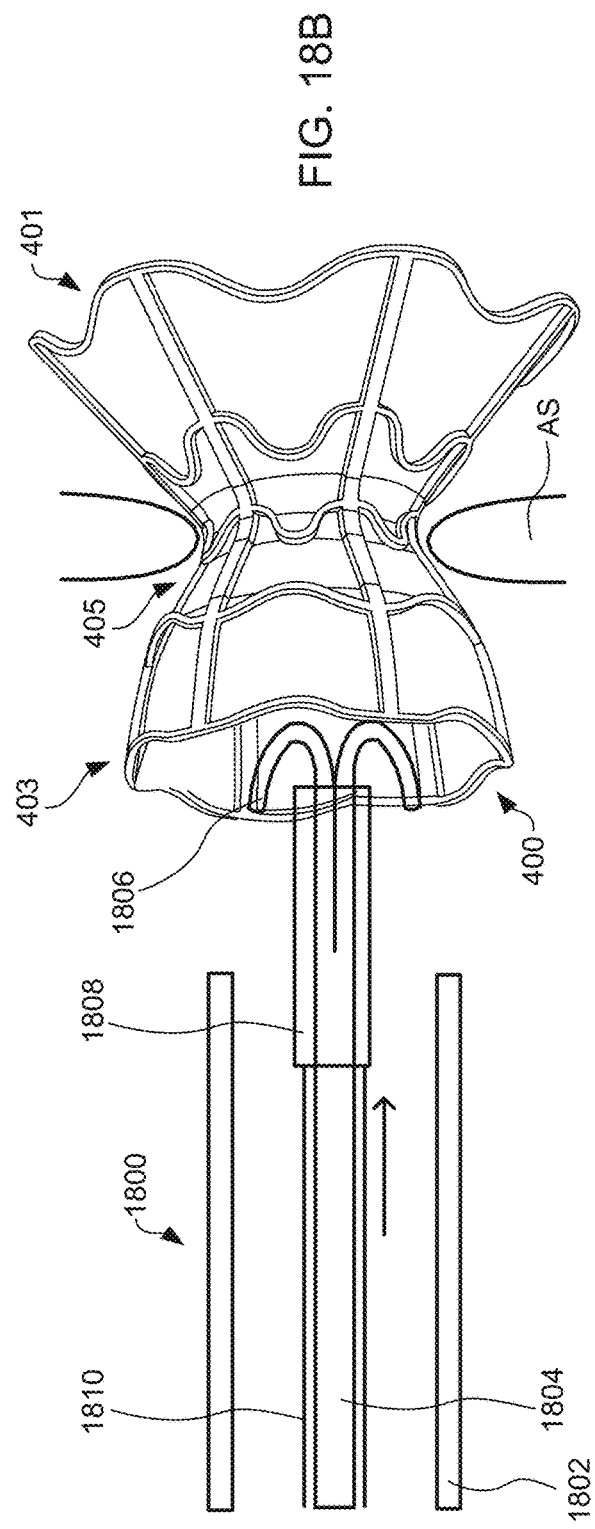

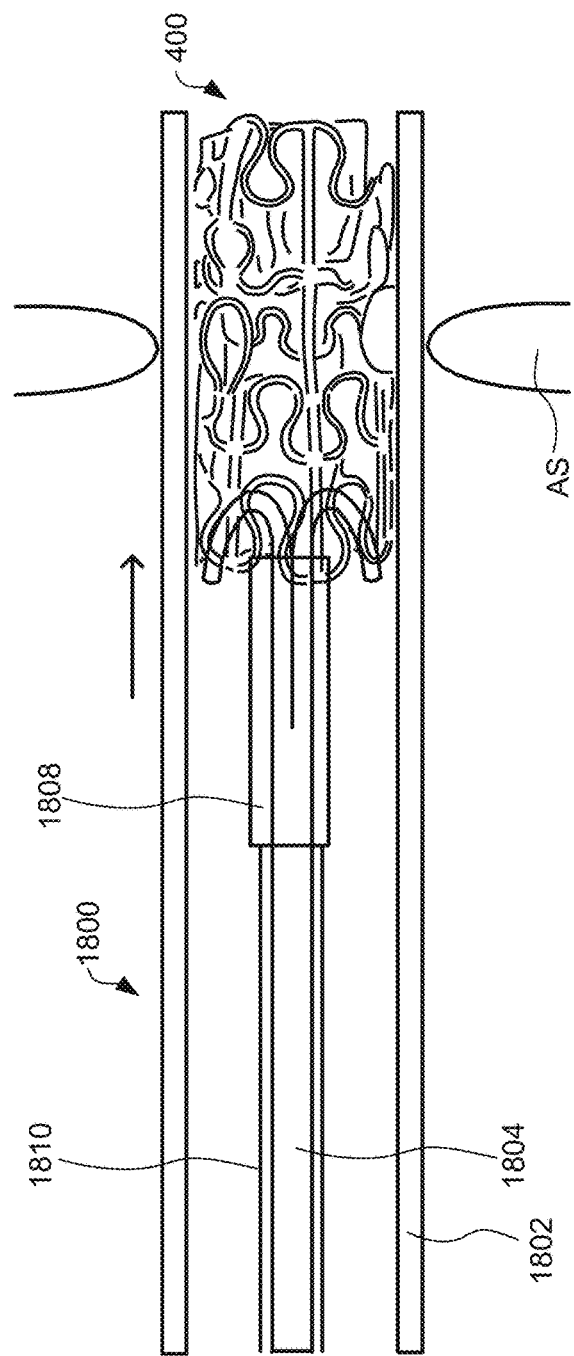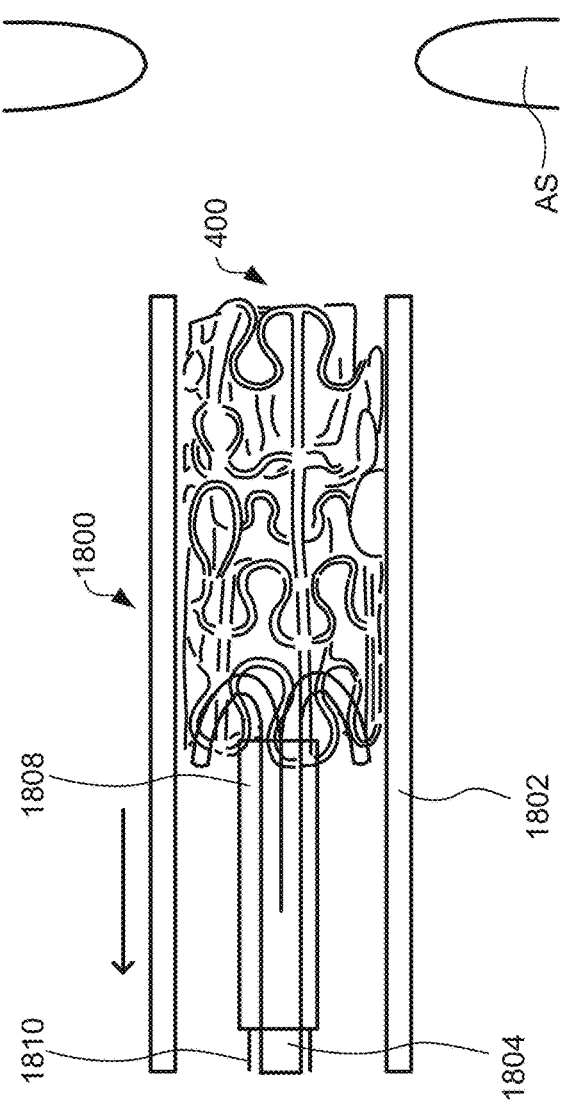

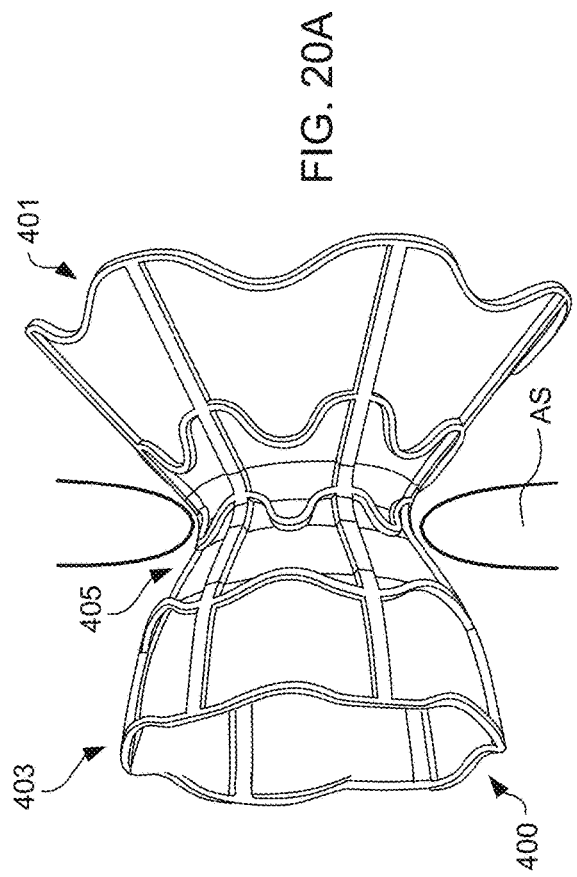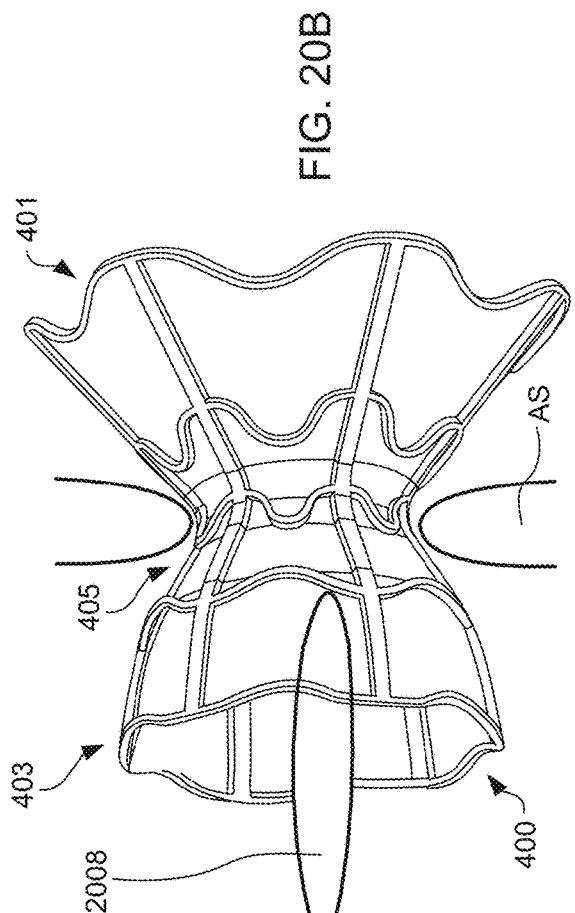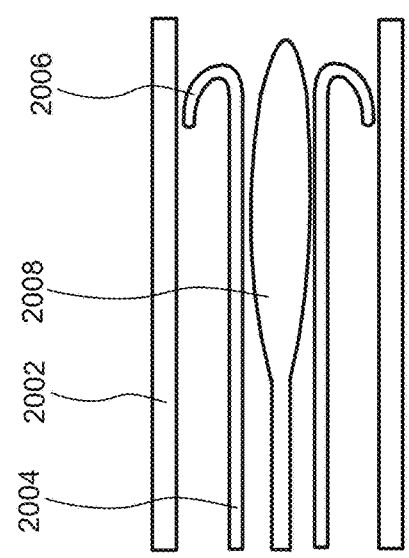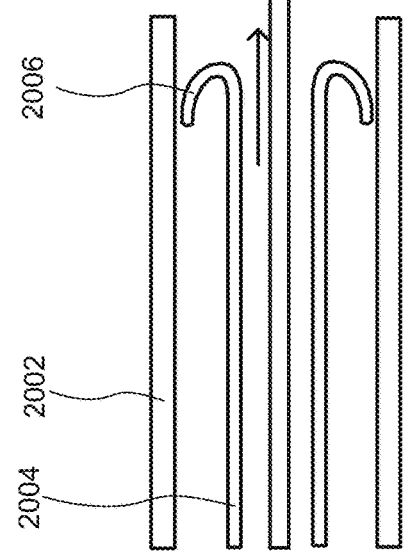
FIG. 20A
FIG. 20B

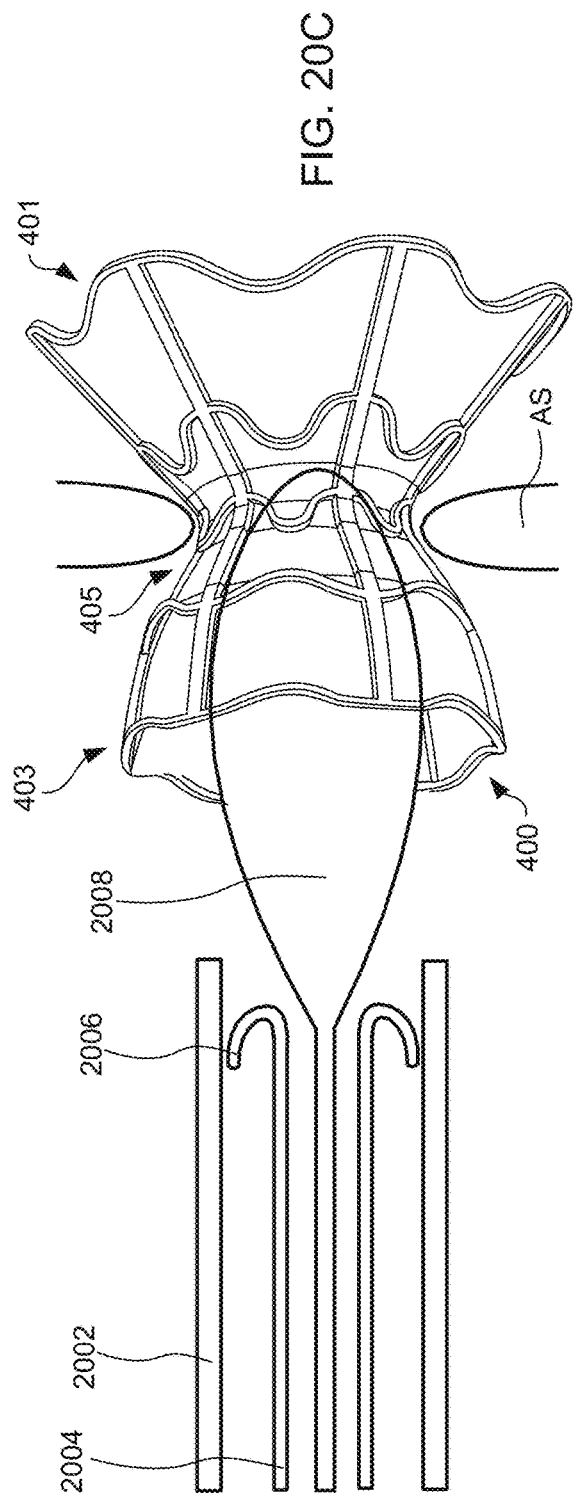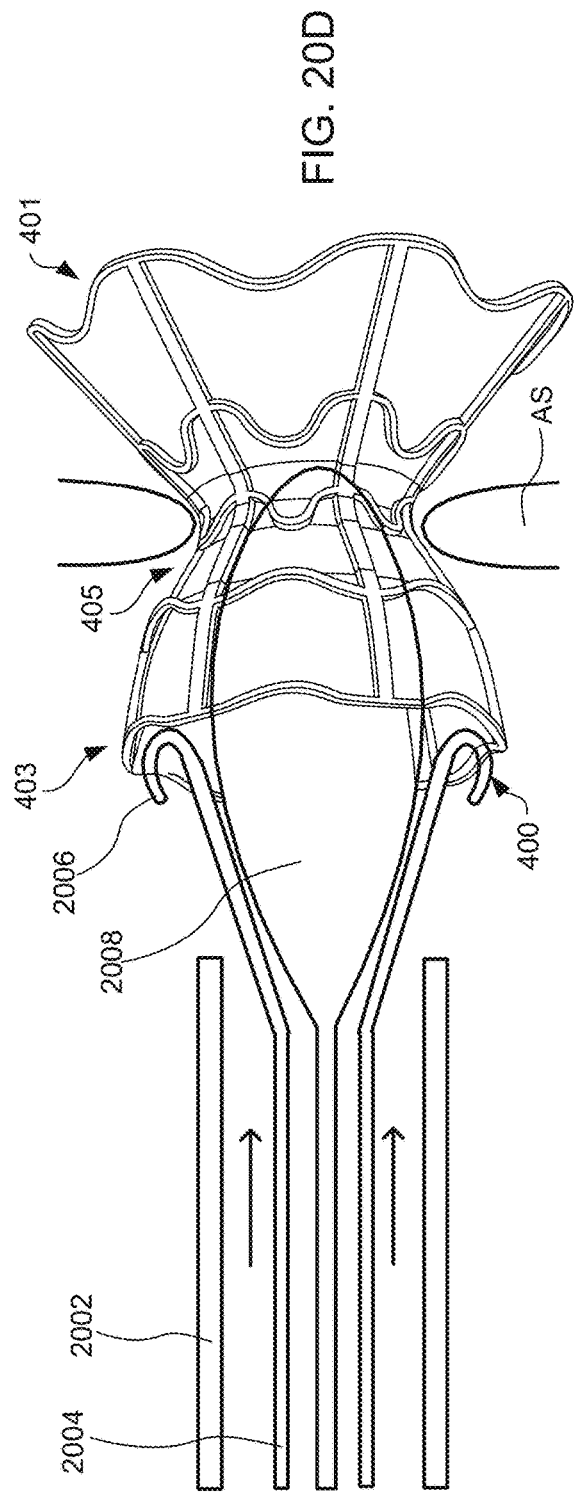

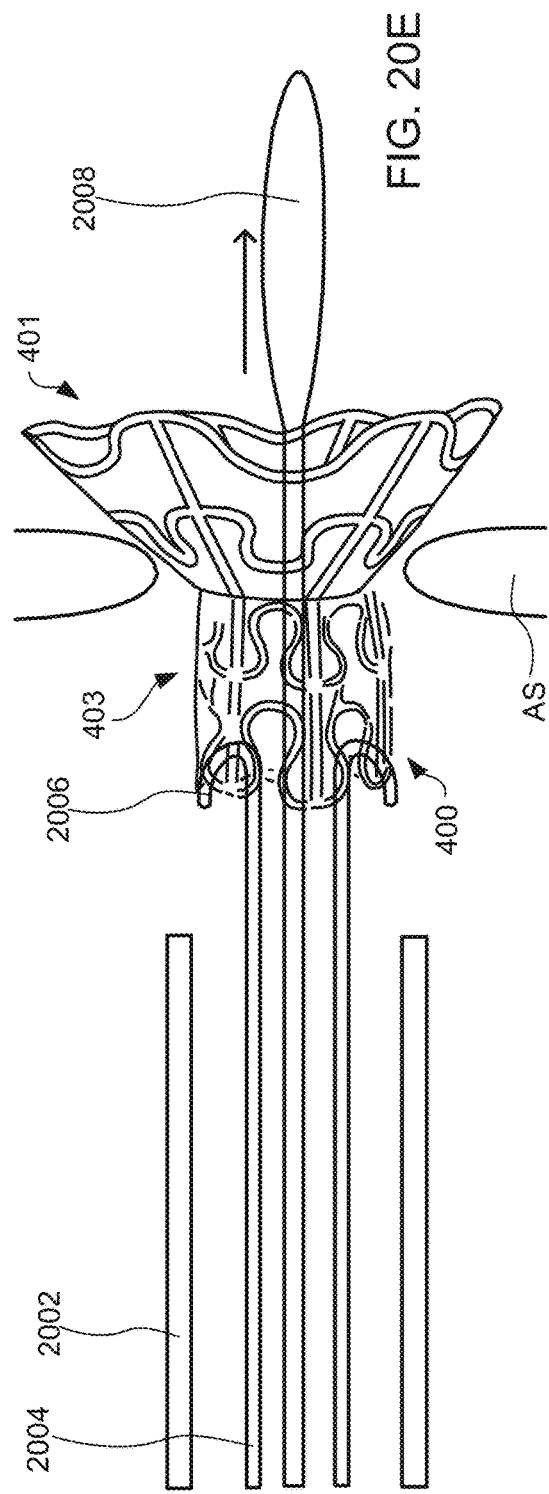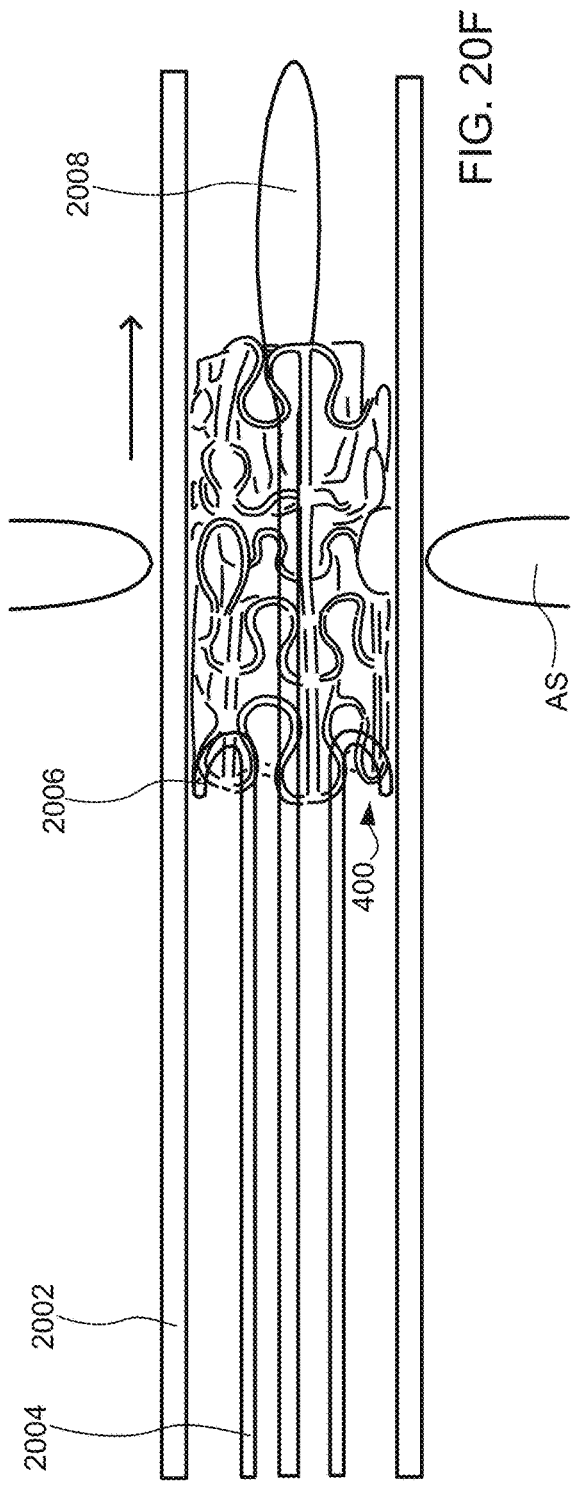

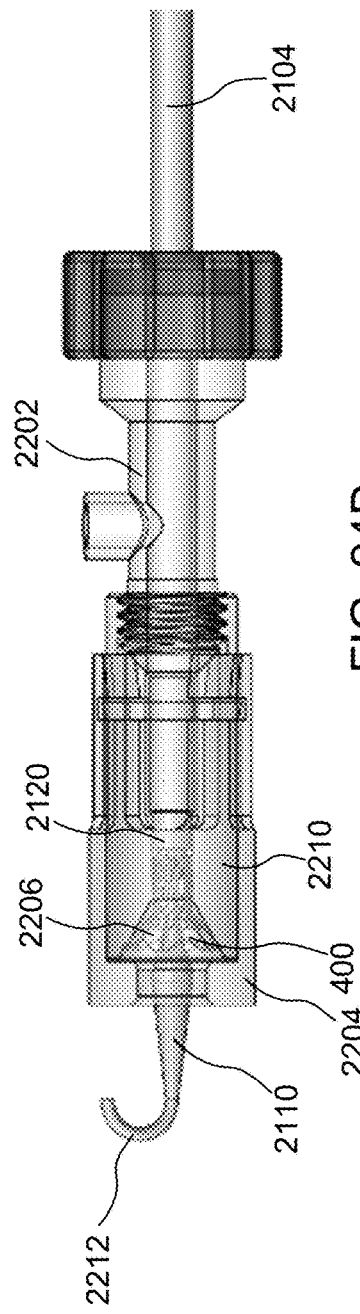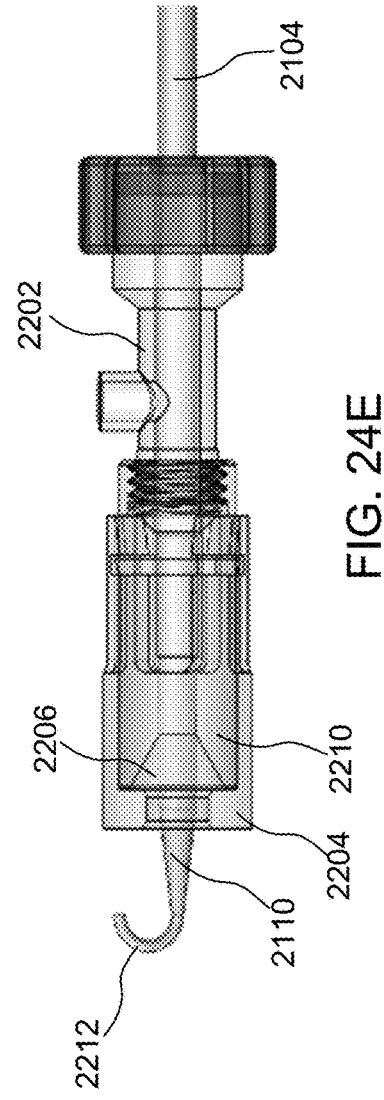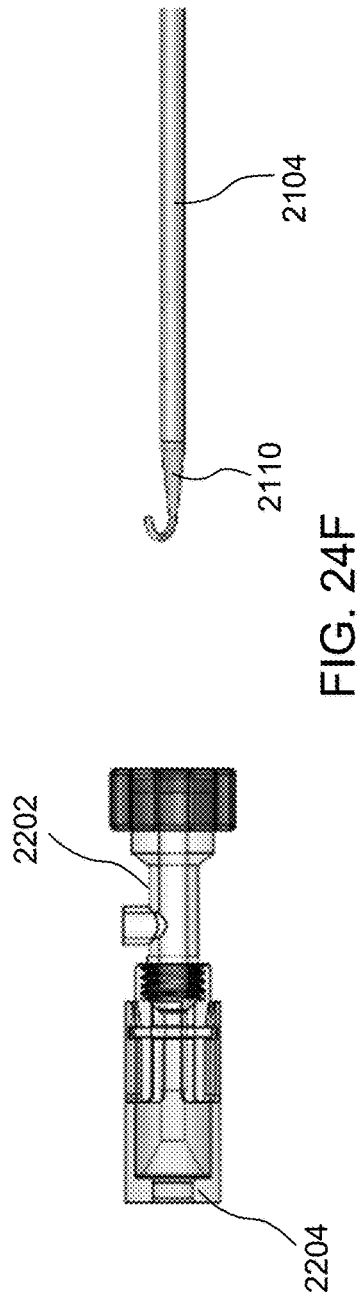

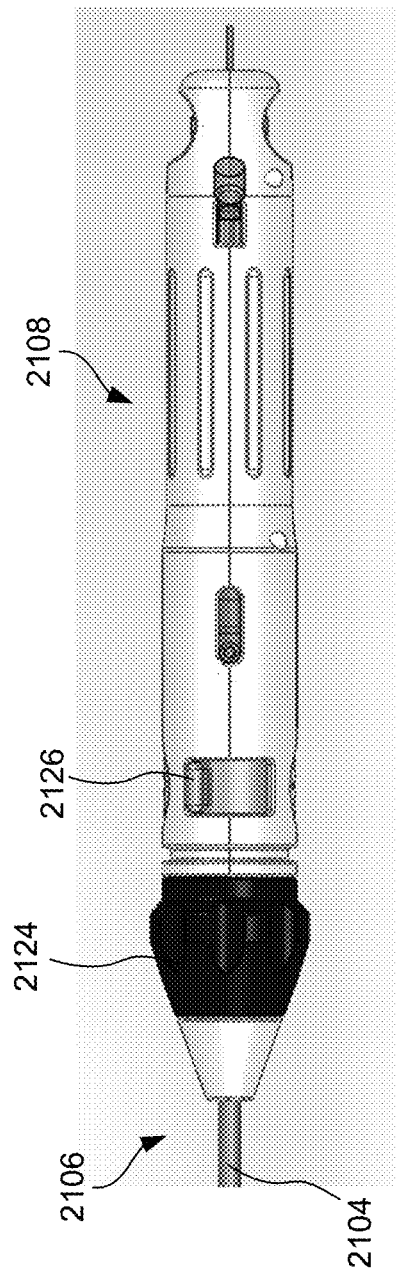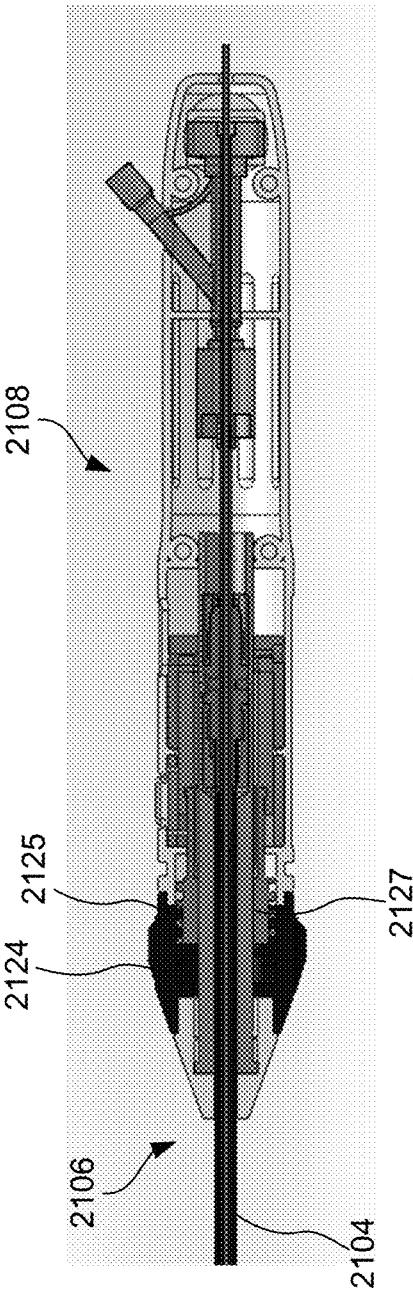

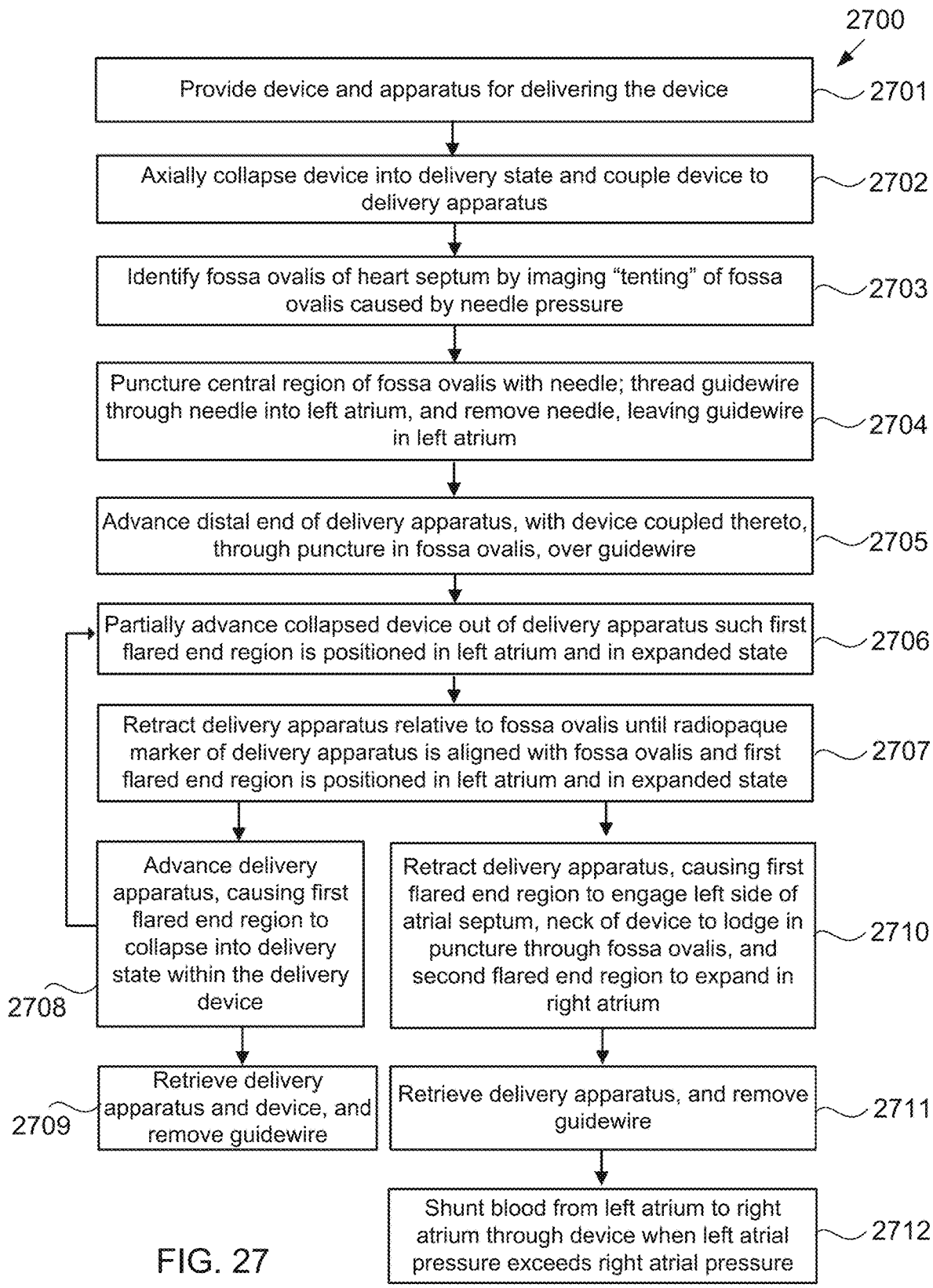

SECTION A-A

SYSTEMS AND METHODS FOR DELIVERING IMPLANTABLE DEVICES ACROSS AN ATRIAL SEPTUM

FIELD OF THE INVENTION

This application generally relates to devices and methods for delivering implantable devices to the atrial septum, particularly in subjects with heart pathologies such as pulmonary arterial hypertension (PAH), congestive heart failure (CHF) or myocardial infarction (MI).

BACKGROUND OF THE INVENTION

Pulmonary arterial hypertension occurs when the pressure within the blood vessels and lungs becomes too high. PAH may be caused by obstruction in the arties in the lung such as the development of scar tissue in the blood vessels of the lungs, but in many cases, the cause is unknown. Under normal conditions, the pressure within the right side of the heart and the blood vessels of the lungs is lower than the rest of the body which maximizes oxygenation of the blood in the lungs. With PAH, the heart must work harder under greater pressure to pump blood through the arteries in the lungs, weakening the heart muscles over time. As a result, the heart may be unable to sufficiently pump blood to the lungs to be oxygenated to keep the body functioning normally.

Heart failure is the physiological state in which cardiac output is insufficient to meet the needs of the body or to do so only at a higher filling pressure. There are many underlying causes of HF, including myocardial infarction, coronary artery disease, valvular disease, hypertension, and myocarditis. Chronic heart failure is associated with neurohormonal activation and alterations in autonomic control. Although these compensatory neurohormonal mechanisms provide valuable support for the heart under normal physiological circumstances, they also play a fundamental role in the development and subsequent progression of HF.

For example, one of the body's main compensatory mechanisms for reduced blood flow in HF is to increase the amount of salt and water retained by the kidneys. Retaining salt and water, instead of excreting it via urine, increases the volume of blood in the bloodstream and helps to maintain blood pressure. However, the larger volumes of blood also cause the heart muscle, particularly the ventricles, to become enlarged. As the heart chambers become enlarged, the wall thickness decreases and the heart's contractions weaken, causing a downward spiral in cardiac function. Another compensatory mechanism is vasoconstriction of the arterial system, which raises the blood pressure to help maintain adequate perfusion, thus increasing the load that the heart must pump against.

In low ejection fraction (EF) heart failure, high pressures in the heart result from the body's attempt to maintain the high pressures needed for adequate peripheral perfusion. However, as the heart weakens as a result of such high pressures, the disorder becomes exacerbated. Pressure in the left atrium may exceed 25 mmHg, at which stage fluids from the blood flowing through the pulmonary circulatory system transudate or flow out of the pulmonary capillaries into the pulmonary interstitial spaces and into the alveoli, causing lung congestion and, if untreated, the syndrome of acute pulmonary edema and death.

Table 1 lists typical ranges of right atrial pressure (RAP), right ventricular pressure (RVP), left atrial pressure (LAP), left ventricular pressure (LVP), cardiac output (CO), and stroke volume (SV) for a normal heart and for a heart suffering from HF. In a normal heart beating at around 70 beats/minute, the stroke volume needed to maintain normal cardiac output is about 60 to 100 milliliters. When the preload, after-load, and contractility of the heart are normal, the pressures required to achieve normal cardiac output are listed in Table 1. In a heart suffering from HF, the hemodynamic parameters change (as shown in Table 1) to maintain peripheral perfusion.

TABLE 1

| Parameter | Normal Range | HF Range |
| --- | --- | --- |
| RAP (mmHg) | 2-6 | 6-20 |
| RVSP (mmHg) | 15-25 | 20-80 |
| LAP (mmHg) | 6-12 | 15-50 |
| LVEDP (mmHg) | 6-12 | 15-50 |
| CO (liters/minute) | 4-8 | 2-6 |
| SV (milliliters/beat) | 60-100 | 30-80 |

HF is generally classified as either systolic heart failure (SHF) or diastolic heart failure (DHF). In SHF, the pumping action of the heart is reduced or weakened. A common clinical measurement is the ejection fraction, which is a function of the blood ejected out of the left ventricle (stroke volume) divided by the maximum volume in the left ventricle at the end of diastole or relaxation phase. A normal ejection fraction is greater than 50%. Systolic heart failure generally causes a decreased ejection fraction of less than 40%. Such patients have heart failure with reduced ejection fraction (HFrEF). A patient with HFrEF may usually have a larger left ventricle because of a phenomenon called "cardiac remodeling" that occurs secondary to the higher ventricular pressures.

In DHF, the heart generally contracts normally, with a normal ejection fraction, but is stiffer, or less compliant, than a healthy heart would be when relaxing and filling with blood. Such patients are said to have heart failure with preserved ejection fraction (HFpEF). This stiffness may impede blood from filling the heart and produce backup into the lungs, which may result in pulmonary venous hypertension and lung edema. HFpEF is more common in patients older than 75 years, especially in women with high blood pressure.

Both variants of HF have been treated using pharmacological approaches, which typically involve the use of vasodilators for reducing the workload of the heart by reducing systemic vascular resistance, as well as diuretics, which inhibit fluid accumulation and edema formation, and reduce cardiac filling pressure. No pharmacological therapies have been shown to improve morbidity or mortality in HFpEF whereas several classes of drugs have made an important impact on the management of patients with HFrEF, including renin-angiotensin antagonists, beta blockers, and mineralocorticoid antagonists. Nonetheless, in general, HF remains a progressive disease and most patients have deteriorating cardiac function and symptoms over time. In the U.S., there are over 1 million hospitalizations annually for acutely worsening HF and mortality is higher than for most forms of cancer.

In more severe cases of HFrEF, assist devices such as mechanical pumps are used to reduce the load on the heart by performing all or part of the pumping function normally done by the heart. Chronic left ventricular assist devices (LVAD), and cardiac transplantation, often are used as measures of last resort. However, such assist devices typically are intended to improve the pumping capacity of the heart, to increase cardiac output to levels compatible with normal life, and to sustain the patient until a donor heart for transplantation becomes available. Such mechanical devices enable propulsion of significant volumes of blood (liters/min), but are limited by a need for a power supply, relatively large pumps, and pose a risk of hemolysis, thrombus formation, and infection. Temporary assist devices, intra-aortic balloons, and pacing devices have also been used.

Various devices have been developed using stents to modify blood pressure and flow within a given vessel, or between chambers of the heart. Implantable interatrial shunt devices have been successfully used in patients with severe symptomatic heart failure. By diverting or shunting blood from the left atrium (LA) to the right atrium (RA), the pressure in the left atrium is lowered or prevented from elevating as high as it would otherwise (left atrial decompression). Such an accomplishment would be expected to prevent, relieve, or limit the symptoms, signs, and syndromes associated of pulmonary congestion. These include severe shortness of breath, pulmonary edema, hypoxia, the need for acute hospitalization, mechanical ventilation, and death.

Percutaneous implantation of interatrial shunts generally requires transseptal catheterization immediately preceding shunt device insertion. The transseptal catheterization system is placed from an entrance site in the femoral vein, across the interatrial septum in the region of fossa ovalis (FO), which is the central and thinnest region of the interatrial septum. The FO in adults is typically 15-20 mm in its major axis dimension and <3 mm in thickness, but in certain circumstances may be up to 10 mm thick. LA chamber access may be achieved using a host of different techniques familiar to those skilled in the art, including but not limited to: needle puncture, stylet puncture, screw needle puncture, and radiofrequency ablation. The passageway between the two atria is dilated to facilitate passage of a shunt device having a desired orifice size. Dilation generally is accomplished by advancing a tapered sheath/dilator catheter system or inflation of an angioplasty type balloon across the FO. This is the same general location where a congenital *secundum* atrial septal defect (ASD) would be located.

In view of the foregoing, it would be desirable to provide devices for delivering implantable devices to the atrial septum of the heart to reduce left atrial pressure.

SUMMARY OF THE INVENTION

The present invention overcomes the drawbacks of previously-known devices by providing apparatus for delivering a device for regulating blood pressure between a patient's left atrium and right atrium. The delivery apparatus includes a sheath having a distal region sized and shaped for percutaneous advancement to the atrial septum, a proximal region, and a sheath lumen extending therethrough, the sheath lumen sized and shaped to receive the shunt in a contracted delivery state. The apparatus also includes a first, outer catheter moveably disposed within the sheath lumen, wherein the first catheter has a first catheter lumen extending therethrough, and a hub moveably disposed within the sheath lumen distal to the first catheter.

The hub has a hub lumen extending therethrough and one or more engagers sized and shaped to releasably engage the shunt in the contracted delivery state within the sheath lumen. The hub may include an engagement portion and a ring portion, wherein the engagement portion of the hub has a diameter smaller than a diameter of the ring portion, and wherein the one or more engagers are disposed circumferentially around the engagement portion of the hub. For example, a first expandable end of the shunt may be positioned between the one or more engagers and the ring portion and between an outer surface of the engagement portion and an inner wall of the sheath in the contracted delivery state within the sheath lumen. The hub further may include a proximal portion, such that the first catheter has a cavity sized and shaped to receive at least a portion of the proximal portion to limit movement of the hub relative to the first catheter.

In addition, the apparatus further includes a second, inner catheter moveably disposed within the first catheter lumen and the hub lumen, and wherein the first catheter and the hub are movable which the second catheter remains in place. The second catheter may include a stop, e.g., a lock ring, disposed at a distal end of the second catheter, such that the hub has a cavity sized and shaped to receive at least a portion of the stop to limit movement of the hub relative to the second catheter. In addition, the second catheter may include a guidewire lumen extending therethrough sized and shaped to receive a guidewire.

The apparatus also includes a handle disposed at the proximal region of the sheath. The first catheter, the hub, and the second catheter are independently movable relative to the sheath responsive to actuation at the handle to facilitate transition of the shunt from the contracted delivery state to an expanded deployed state at the atrial septum. In addition, the handle includes a knob that when actuated facilitates deployment of and/or halfway retrieval of the shunt at the atrial septum by adjusting a length of the delivery apparatus relative to the sheath. For example, the knob may be actuated to gradually adjust the length of the delivery apparatus relative to the sheath to assist in halfway retrieval of the shunt.

The handle may include a first actuator, the first actuator coupled to the sheath such that actuation of the first actuator causes the sheath to move relative to the hub, the first catheter, and the second catheter. The handle also may include a second actuator, the second actuator coupled to the second catheter such that actuation of the second actuator causes the second catheter to move relative to the sheath, the hub, and the first catheter. For example, the second actuator may be coupled to the second catheter via one or more guiderails and a pusher plate. Accordingly, the first actuator may move along the one or more guiderails within a housing of the handle.

The apparatus also includes a locking mechanism for releasably coupling the hub and the first catheter. Thus, the handle further includes a third actuator operatively coupled to the locking mechanism such that actuation of the third actuator causes the locking mechanism to couple or decouple the hub and the first catheter. The handle further may include an actuation ring positioned between the second actuator and the third actuator, wherein the actuation ring has an indented distal edge sized and shaped to engage with a toothed proximal edge of the third actuator, and a grooved proximal edge sized and shaped to engage with an indented distal edge of the second actuator. For example, actuation of the third actuator may orient the actuation ring such that actuation of the second actuator is inhibited.

In accordance with another aspect of the invention, a method for delivering a shunt at an atrial septum of a patient is provided. The method includes selecting a sheath and a delivery apparatus including a first, outer catheter, a hub distal to and releasably coupled to the first catheter, the hub having one or more engagers disposed thereon, the one or more engagers sized and shaped to releasably engage with the shunt in a contracted delivery state within a lumen of the sheath, and a second, inner catheter extending through a center lumen of the first catheter and the hub. The first catheter, the hub, and the second catheter are independently moveable relative to the sheath upon actuation of a handle operatively coupled to the sheath and the delivery apparatus.

The method further includes advancing a distal end of the sheath through the atrial septum into a first atrium, and then advancing the delivery apparatus within the lumen of the sheath, and actuating the handle to move the delivery apparatus distally relative to the sheath such that a first expandable end of the shunt extends distally out the distal end of the sheath and transitions from a contracted state within the lumen of the sheath to an expanded state in the first atrium. The method then includes (1) actuating the handle to move the second catheter distally relative to the sheath, the first catheter, and the hub; (2) moving the delivery apparatus and the sheath proximally until the first expandable end of the shunt rests against the atrial septum from within the first atrium; and (3) actuating the handle to decouple the hub and the first catheter. The method further includes moving the first catheter and the sheath proximally relative to the hub to disengage a second expandable end of the shunt with the one or more engagers of the hub and expose the second expandable end of the shunt from the sheath to transition from the contracted state within the lumen of the sheath to an expanded state in a second atrium. Finally, the method includes removing the sheath and the delivery apparatus from the patient such that a neck region of the shunt is positioned within the atrial septum to permit blood to flow through an opening in the neck region of the shunt and thereby through the atrial septum.

In accordance with one aspect of the invention, the method further includes actuating the handle to adjust a length of the delivery apparatus relative to a length of the sheath prior to disengaging the second expandable end of the shunt with the one or more engagers of the hub to assist in halfway retrieval of the shunt. For example, the handle may be actuated to gradually adjust the length of the delivery apparatus relative to the length of the sheath to facilitate retrieving the shunt in a partially deployed state. In accordance with yet another aspect of the invention, the second catheter includes a guidewire lumen extending therethrough sized and shaped to receive a guidewire, such that the method also includes inserting a guidewire percutaneously through the atrial septum into the first atrium. Thus, advancing the delivery apparatus through the sheath includes advancing the delivery apparatus over the guidewire. As will be understood by a person ordinarily skilled in the art, a dilator may be advanced over the guidewire through the fossa ovalis to enlarge the opening within the atrial septum, and removed prior to advancing the sheath and the delivery apparatus within the lumen of the sheath over the guidewire.

BRIEF DESCRIPTION OF THE DRAWINGS

FIGS. 1A and 1B illustrate an exemplary apparatus for delivering devices in accordance with the present invention, wherein the exemplary apparatus is in the engaged position in FIG. 1A and the disengaged position in FIG. 1B.

FIGS. 3A to 3D illustrate the inner components at the distal end of the exemplary apparatus, wherein FIGS. 3A and 3C show the components in the engaged position and FIGS. 3B and 3D show the components in the disengaged position.

FIGS. 9A to 9D illustrate the inner components at the distal end of the alternative exemplary apparatus of FIGS. 8A and 8B, wherein FIGS. 9A and 9C show the components in the engaged position and FIGS. 9B and 9D show the components in the disengaged position.

FIGS. 18A-18F schematically illustrate steps taken during the method of FIG. 17, according to some embodiments of the present invention.

FIGS. 20A-20G schematically illustrate steps taken during the method of FIG. 19, according to some embodiments of the present invention.

FIGS. 24A-24F illustrates steps taken during the method of FIG. 23, according to some embodiments of the present invention.

FIG. 26A illustrates a proximal end of the apparatus of FIG. 21A for delivering devices in accordance with the present invention, and FIG. 26B illustrates a cross-sectional view of the apparatus of FIG. 26A.

FIG. 27 is a flow chart of steps in an exemplary method of percutaneously implanting and halfway-retrieval of an hourglass-shaped device in a puncture through the fossa ovalis using the alternative exemplary apparatus of FIG. 21A, according to some embodiments of the present invention.

DETAILED DESCRIPTION OF THE INVENTION

Figure 2A:
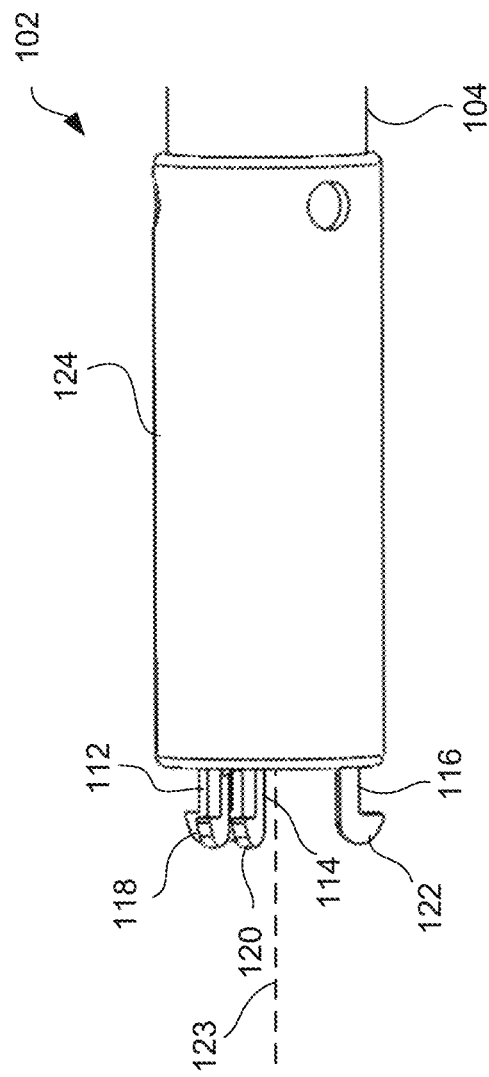
FIGS. 2A and 2B, respectively, illustrate the distal end of the exemplary apparatus in the engaged position shown in FIG. 1A and the disengaged position shown in FIG. 1B.

Embodiments of the present invention are directed to devices for delivering implantable devices to the atrial septum of the heart, and thus may be useful in treating subjects suffering from heart failure or other disorders associated with elevated left atrial pressure. For example, the inventive device may be designed to deliver an hourglass or "diabolo" shaped stent, preferably formed of a shape memory metal as described in U.S. Pat. No. 9,629,715 to Nitzan, assigned to the assignee of the present invention, the entire contents of which are incorporated herein by reference. The delivery device is configured to lodge the stent securely in the atrial septum, preferably the fossa ovalis, to function as an interatrial shunt, allowing blood flow from the left atrium to the right atrium.

Referring to FIGS. 1A and 1B, apparatus 100 is provided for delivering interatrial shunt devices, e.g., devices described in U.S. Pat. No. 9,629,715 to Nitzan and U.S. Pat. No. 9,713,696 to Yacoby, assigned to the assignee of the present invention, the entire contents of each of which are incorporated herein by reference. Apparatus 100 may include distal end 102, catheter 104, and proximal end 106 having handle 108. Distal end 102 comprises components suitable for coupling apparatus 100 to devices of the present invention, as described in detail below. Catheter 104 comprises a biocompatible tube shaft of suitable size, e.g., approximately 14 Fr., and suitable length, e.g., approximately 75-100 cm and preferably 85 cm. Proximal end 106 comprises handle 108 that is configured to be manipulated, e.g., by a human hand, to transition components in distal end 102 from an engaged position shown in FIG. 1A to a disengaged position shown in FIG. 1B. Handle 108 may be manipulated, for example, by moving finger grips 110 proximally from a locked position shown in FIG. 1A to an unlocked position shown in FIG. 1B. In addition, handle 108 may be manipulated by moving finger grips 110 distally from the locked position to the unlocked position so as to transition components in distal end 102 from the disengaged position to the engaged position to load devices of the present invention.

Figure 2B:
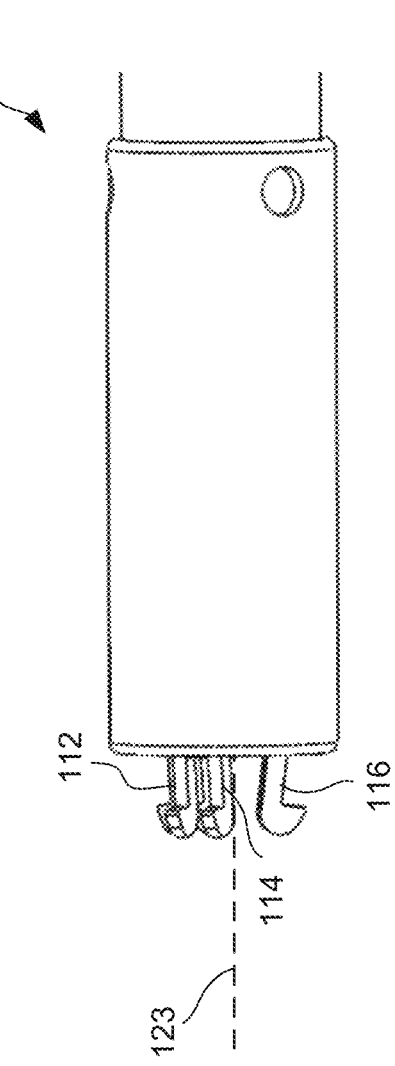

FIGS. 2A and 2B illustrate distal end 102 in the engaged position of FIG. 1A and the disengaged position of FIG. 1B, respectively. At distal end 102, apparatus 100 may include latching legs 112, 114, and 116 having hook portions 118, 120, and 122, respectively. Latching legs 112, 114, and 116 comprise a biocompatible material such as a biocompatible metal or polymer, and are positioned longitudinally and radially so as to firmly secure devices of the present invention for delivery. Hook portions 118, 120, and 122 extend outwardly from the distal end of latching legs 112, 114, and 116, respectively, and are configured to fit securely between struts and rings of the devices of the present invention. Preferably, hook portions 118, 120, and 122 hook outwardly away from center axis 123 of catheter 104 in both the engaged and disengaged positions as shown in FIGS. 1A and 1B. Center axis 123 is centered relative to catheter 104 on both a longitudinal and cross-sectional basis. By facing outwardly from center axis 123, hook portions 118, 120, and 122 may engage the inner surface of the device, e.g., within a lumen of a shunt. In one embodiment, hook portions 118, 120, and 122 hook generally perpendicularly away from center axis 123 from a radial perspective. As will be readily understood by one of ordinary skill in the art, while three latching legs are illustrated, more or fewer latching legs may be used without departing from the scope of the present invention. For example, one, two, four, five, six, or more latching legs may be used. Catheter 104 may include cover tube 124 which may have a larger diameter than the remaining shaft of catheter 104. Cover tube 124 comprises a biocompatible material such as a biocompatible metal or polymer, and may be the same or different material than the remaining shaft of catheter 104. Components at distal end 102, such as latching legs 112, 114, and 116, may be at least partially disposed within cover tube 124. For example, the proximal ends of latching legs 112, 114, and 116 may be coupled to annular member 148 and cover tube 124 by laser welding.

Referring now to FIGS. 3A to 3D, the inner components at distal end 102 of apparatus 100 are illustrated. FIGS. 3A and 3B respectively illustrate distal end 102 in the engaged position of FIGS. 1A and 2A and the disengaged position of FIGS. 1B and 2B. As shown in FIG. 3A, catheter 104 and cover tube 124 comprise lumens 126 and 128, respectively, for housing the inner components. Latching legs 112 and 114 share common ramp portion 130 having inner section 132 and outer section 134 while latching leg 116 has separate ramp portion 136 having inner section 138 and outer section 140. Inner sections 132 and 138 are angled so as to be positioned closer to the central axis of catheter 104 and cover tube 124 relative to the positions of outer sections 134 and 140. Latching legs may also include jogs and protrusions. For example, latching leg 116 illustratively includes protrusion 142 proximal to ramp portion 136, and jog 144 between hook portion 122 and ramp portion 136. Protrusion 142 is configured to contact the distal surface of annular member 148 to maintain suitable positioning of latching leg 116. Jog 144 is shaped to prevent release ring 146 from moving too distally.

Release ring 146 is coupled to latching legs 112, 114, and 116. For example, latching legs 112, 114, and 116 may be partially disposed within release ring 146 as illustrated in FIGS. 3A to 3D. Release ring 146 is moveable within cover tube 124. Release ring 146 may be located in a first position, e.g., an engaged position, where release ring 146 contacts inner sections 132 and 138 of ramp portions 130 and 136 such that latching legs 112, 114, and 116 extend radially outward as shown in FIGS. 3A and 3C. Release ring 146 may be moved to a second position, e.g., a disengaged position, where release ring 146 contacts outer sections 134 and 140 of ramp portions 130 and 136 such that latching legs 112, 114, and 116 move radially inward as shown in FIGS. 3B and 3D. In one embodiment, release ring 146 is configured to move from the second position to the first position to load a device of the present invention and to move from the first position to the second position to release the device.

Annular member 148 may be partially disposed in the proximal end of cover tube 124 and configured to couple cover tube 124 to catheter 104 via a suitable coupling mechanism, e.g., teeth 150, ribs. Annular member 148 includes lumen 152 sized to accept pull-cord 154 therethrough.

Pull-cord 154 is coupled to release ring 146 and actuation of pull-cord 154 moves release ring 146 from the first position shown in FIG. 3A to the second position shown in FIG. 3B, and vice versa. In a preferred embodiment, pull-cord 154 is coupled to handle 108 such that pull-cord 154 is actuated by moving finger grips 110 from a locked position shown in FIG. 1A to an unlocked position shown in FIG. 1B, and vice versa.

Pull-cord 154 may be coupled to release ring 146 via release ring base 156. In this embodiment, release ring base 156 is directly coupled to release ring 146 and pull-cord 154 such that actuation of pull-cord 154 moves release ring base 156 to move release ring 146 from the first position the second position, and vice versa.

Spring 158 may be coupled to the proximal surface of release ring base 156 and the distal surface of annular member 148 such that release ring base 156 and annular member 148 maintain spring 158 therebetween. Spring 158 is configured to bias release ring 146 towards a particular position such as towards the first position as shown in FIG. 3A.

FIGS. 3A and 3C illustrate the components at distal end 102 in an engaged position, where FIG. 3C omits cover tube 124 for clarity. As pull-cord 154 is actuated, e.g., via handle 108, release ring 146 is moved, e.g., via release ring base 156, from the engaged position to the disengaged position shown in FIGS. 3B and 3D, where FIG. 3D omits cover tube 124 for clarity. Release ring 146 slides along ramp portions 130 and 136 from inner sections 132 and 138 to outer sections 134 and 140 such that latching legs 112, 114, and 116 move from being extended radially outward to being positioned radially inward. As release ring 146 moves from the engaged position to the disengaged position, spring 158 is compressed and as release ring 146 moves from the disengaged position to the engaged position, spring 158 is decompressed.

Figure 4B:
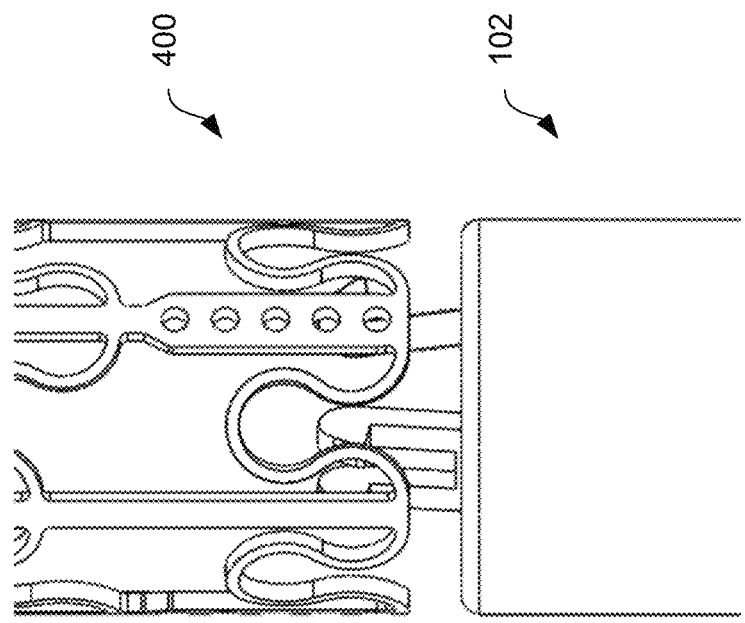
FIG. 4B illustrates the exemplary delivery apparatus disengaged from the exemplary shunt device.
Figure 4A:
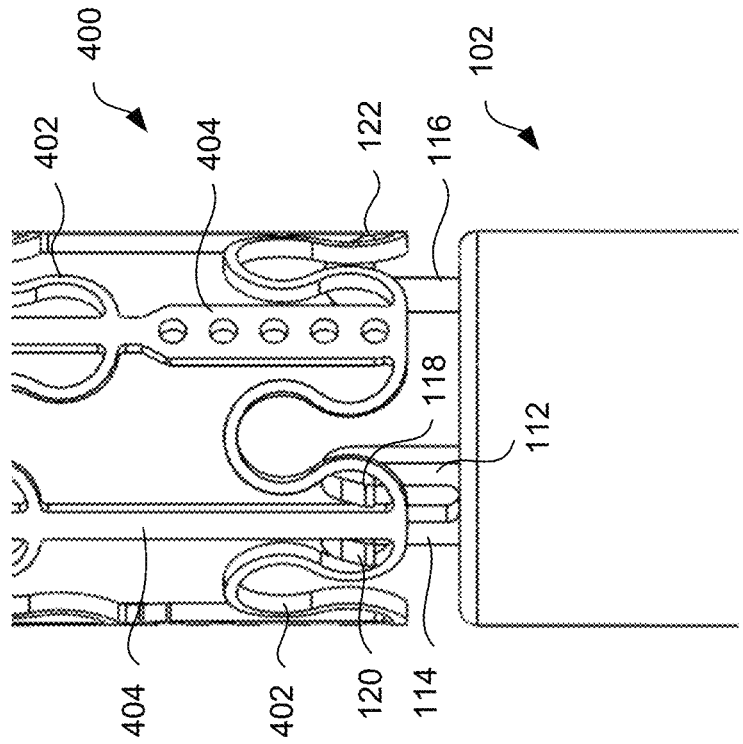
FIG. 4A illustrates the distal end of an exemplary delivery apparatus engaged to an exemplary shunt device, partially shown, in accordance with the present invention

FIG. 4A illustrates the components at distal end 102 of apparatus 100 engaged to an exemplary device of the present invention and FIG. 4B illustrates the components disengaged from the exemplary device. Device 400 includes rings 402 and struts 404 and may be constructed similar to devices described in U.S. Pat. No. 9,629,715 to Nitzan, U.S. Pat. No. 9,713,696 to Yacoby, and U.S. Pat. No. 10,076,403 to Eigler, assigned to the assignee of the present invention, the entire contents of each of which are incorporated herein by reference. As shown in FIG. 4A, latching legs 112, 114, and 116 are sized, shaped, angled, and spaced apart from one another so as to engage device 400 in openings between rings 402 and struts 404 when device 400 is in a contracted, delivery state. Hook portions 118, 120, and 122 are sized, shaped, and angled to fit between rings 402 and struts 404. Hook portions 118, 120, 122 also hook outwardly away from the center axis at the distal end of the delivery apparatus. Accordingly, hook portions 118, 120, 122 may be disposed in the lumen of device 400 in the engaged position of FIG. 4A and engage device 400 from within the inner surface of device 400 such that hook portions 118, 120, 122 extend radially beyond the inner surface of device 400. For example, hook portions 118, 120, 122 may extend radially to the outer surface of device 400 or beyond the outer surface of device 400. As shown in FIG. 4B, latching legs 112, 114, and 116 are configured to move radially inward a sufficient distance to decouple hook portions 118, 120, and 122 from device 400 in the disengaged position, thereby releasing device 400 for implantation.

Figure 5:
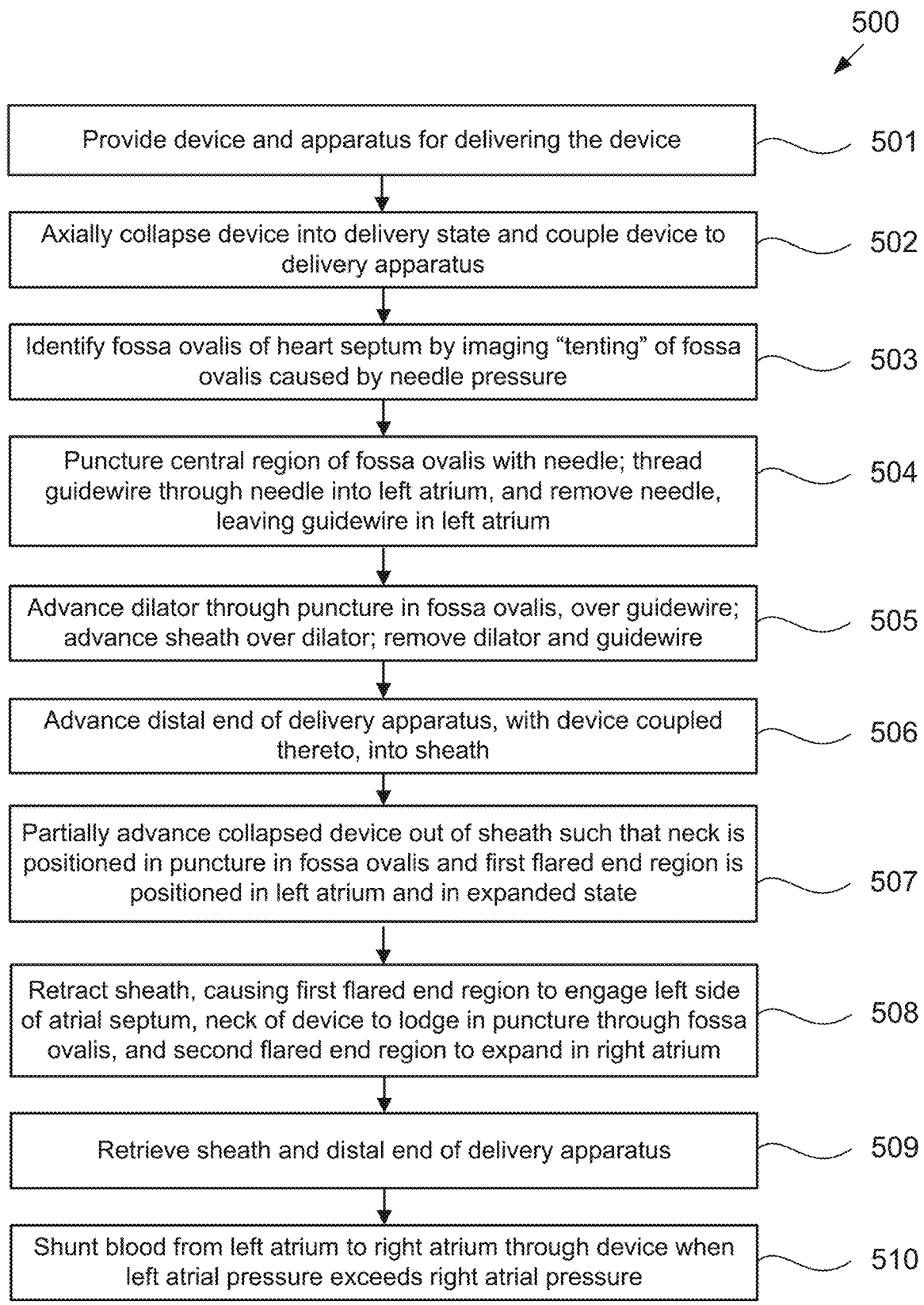
FIG. 5 is a flow chart of steps in a method of percutaneously implanting an hourglass-shaped shunt device in a puncture through the fossa ovalis using the exemplary delivery apparatus, according to some embodiments of the present invention.

FIG. 5 is a flowchart of exemplary method 500 of delivering device 400 illustrated in FIGS. 4A and 4B to reduce left atrial pressure in a subject, for example, a human having CHF, using apparatus 100 illustrated in FIGS. 1A-1B. Some of the steps of method 500 may be further elaborated by referring to FIGS. 6A-6Q.

Referring to FIG. 5, first, a device and apparatus for delivering the device are provided (step 501). The device may be an hourglass-shaped device having a plurality of sinusoidal rings connected by longitudinally extending struts that define first and second flared end regions and a neck disposed therebetween, as well as an optional tissue valve coupled to the second flared end region.

Figure 6A:
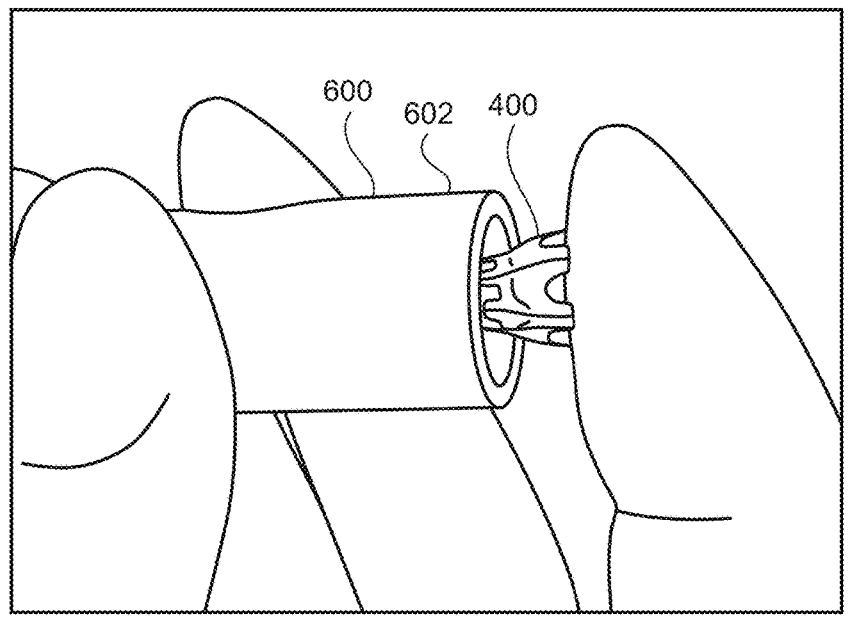
FIGS. 6A-6Q schematically illustrate steps taken during the method of FIG. 5, according to some embodiments of the present invention.
Figure 6B:
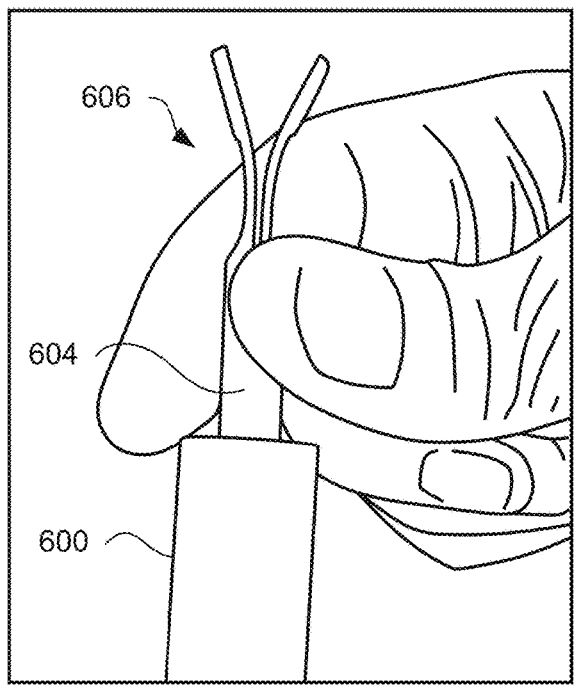
Figure 6C:
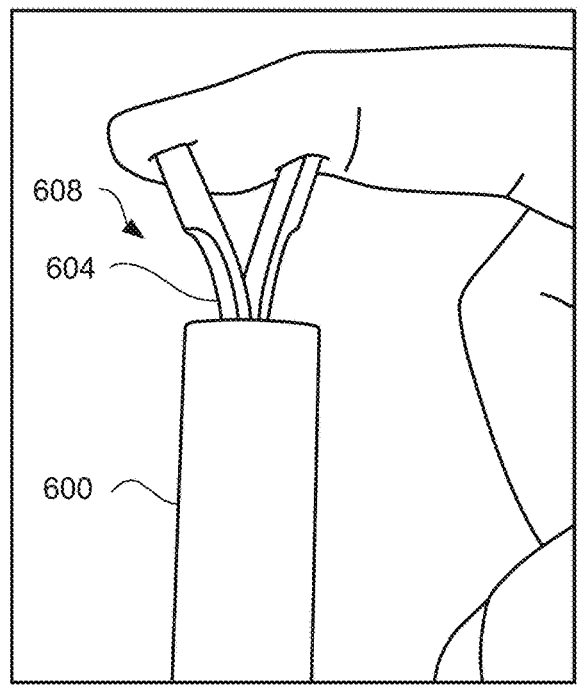

Then, the device is collapsed radially to a contracted, delivery state and coupled to the delivery apparatus (step 502). For example, as illustrated in FIGS. 6A-6C, device 400 may be loaded into tapered loading tube 600 by first placing device 400 within wide diameter end 602 of loading tube 600 as shown in FIG. 6A. Then, using loading tool 604, device 400 is crimped down within loading tube 600. Loading tool 604 includes thin leg end 606 having two thin legs and wide leg end 608 having two wide legs. Device 400 may be pushed into loading tube 600 first by thin leg end 606 as illustrated in FIG. 6B and then pushed further into loading tube 600 by wide leg end 608 as illustrated in FIG. 6C. As will be understood by a person ordinarily skilled in the art, thin leg end 606 may have more than two thin legs, e.g., three, four, or more thin legs, and accordingly, wide leg end 608 may have more than two wide legs, e.g., three, four, or more wide legs.

Figure 6D:
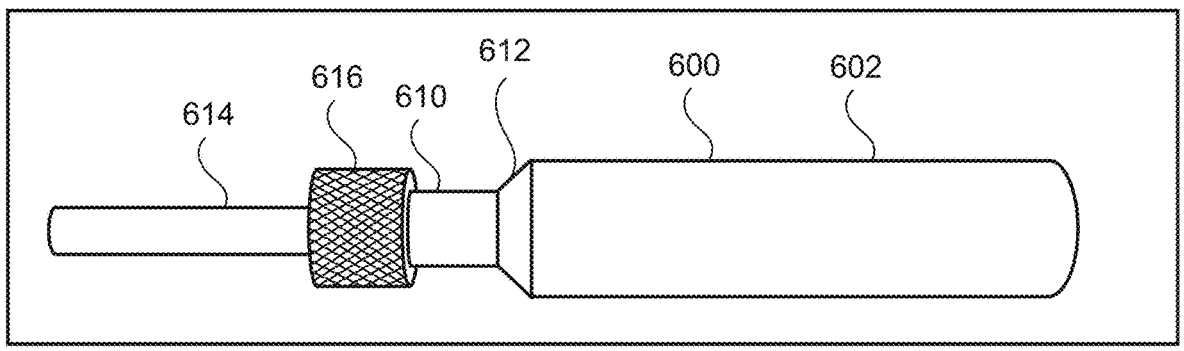

In FIG. 6D, device 400 is disposed within thin diameter end 610 of loading tube 600. Thin diameter end 610 has a suitable internal diameter for contracting the device, e.g., approximately 14 Fr. Loading tube 600 includes tapered section 612 between wide diameter end 602 and thin diameter end 610. Tapered section 612 facilitates radial compression of device 400 into thin diameter end 610. Loading tube 600 is coupled to loading cartridge 614 via coupling section 616 having a suitable coupling mechanism, e.g., threads, ribs. Loading cartridge 614 may be transparent and has a suitable internal diameter, e.g., approximately 14 Fr.

Figure 6E:
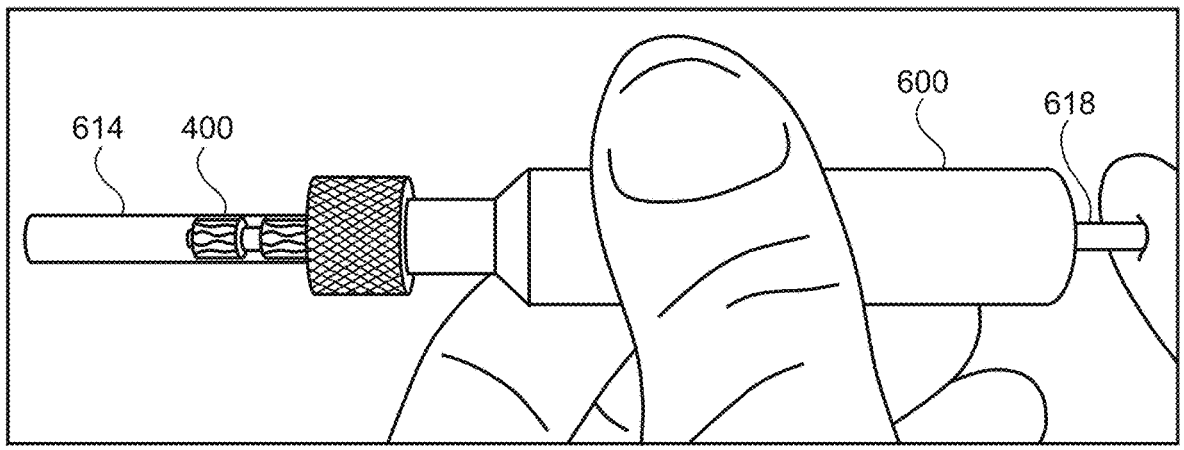
Figure 6F:
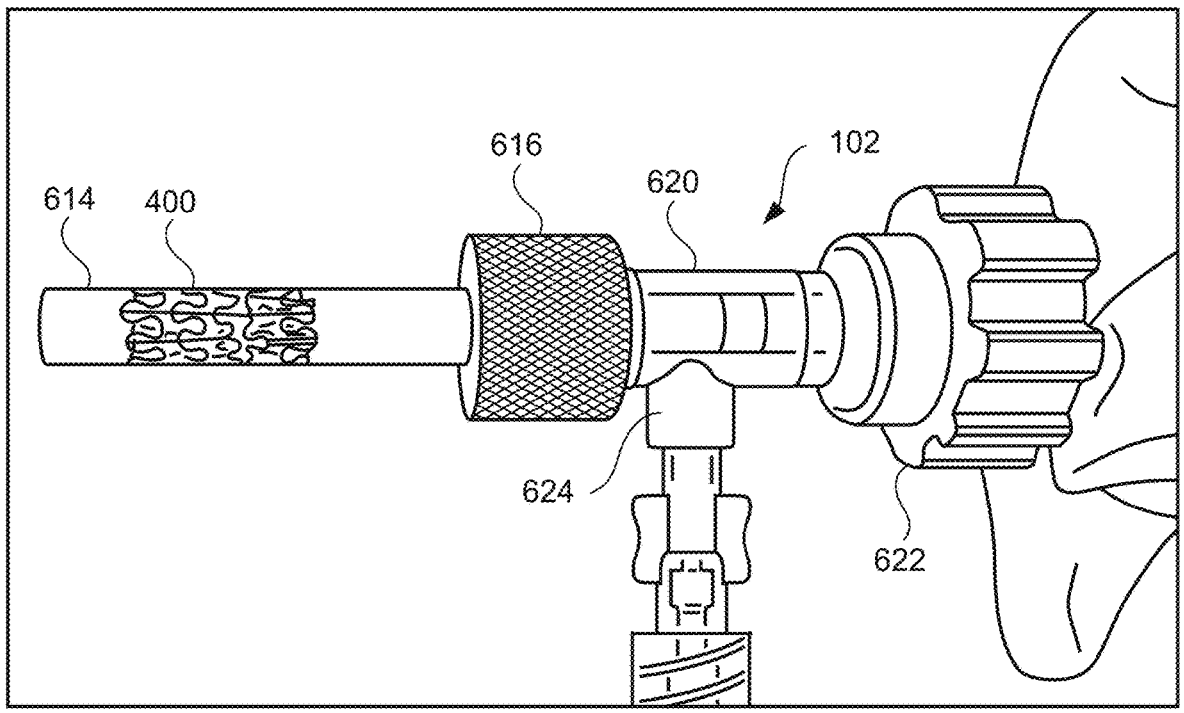

Referring to FIG. 6E, device 400 is pushed into loading cartridge 614 using pusher 618. Pusher 618 has a suitable diameter, e.g., approximately 14 Fr., and may have a "star"-shaped end (not shown). In accordance with one aspect of the invention, the thin leg end of loading tool 604 is long enough to serve as pusher 618. Loading cartridge 614 is disconnected from loading tube 600 and connected to hemostasis valve section 620, which may be a Tuohy-Borst valve, as shown in FIG. 6F. Valve section 620 includes knob 622 and Y-connector 624. Distal end 102 of apparatus 100 is inserted through knob 622 of valve section 620. Knob 622 and Y-connector 624 are adjusted to permit movement of apparatus 100 while maintaining a seal to prevent fluid leakage, e.g., air leakage, blood leakage. The steps shown in FIGS. 6A-6F may be performed while device 400 is immersed in an anticoagulant such as heparinized saline.

Figure 6G:
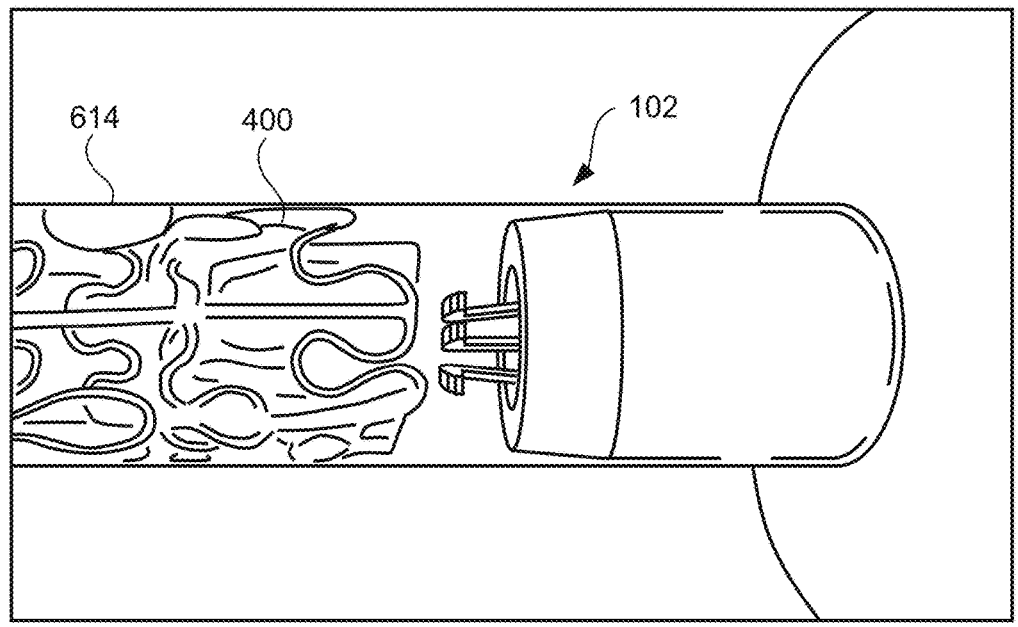
Figure 6H:
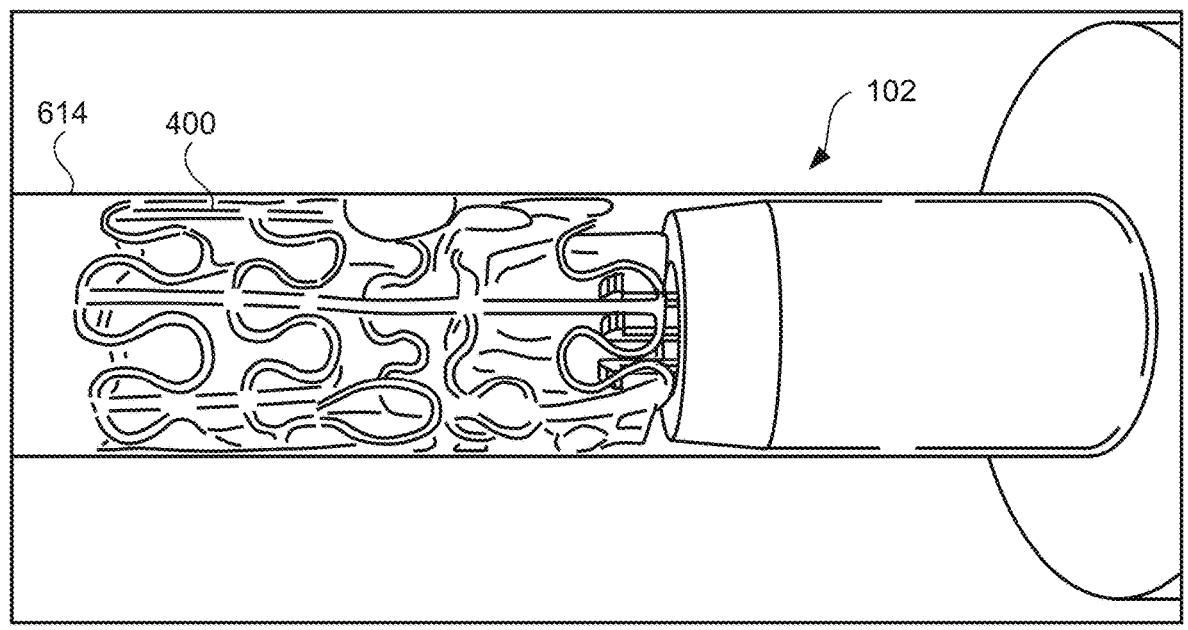
Figure 6I:
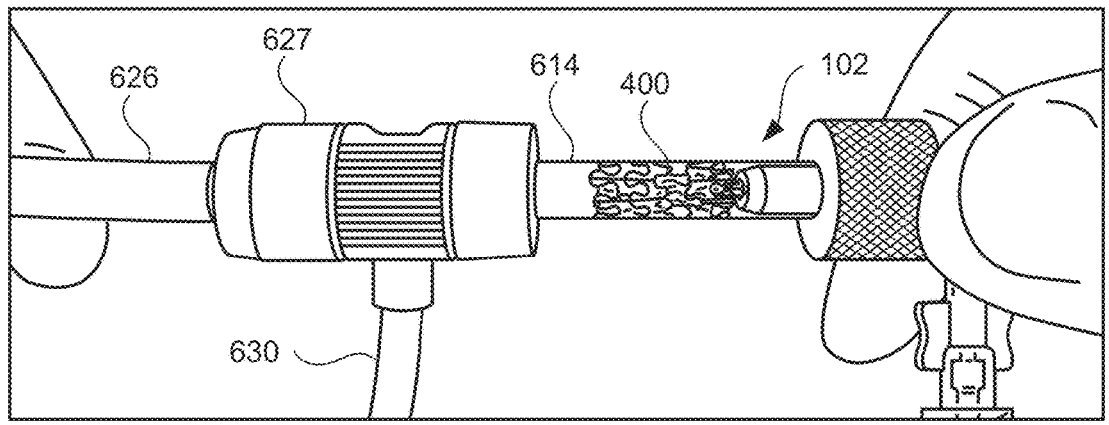

FIGS. 6G and 6H illustrate coupling device 400 to apparatus 100 at distal end 102. Distal end 102 is advanced within loading cartridge 614 toward device 400. The components of distal end 102 may be in the disengaged position as illustrated in FIG. 6G. For example, the release ring at distal end 102 may contact an outer section of the ramp portions of the latching legs such that the latching legs are disposed radially inward. Next, distal end 102 is moved longitudinally toward device 400 and rotated to align the latching legs with suitable portions of device 400, e.g., at openings between struts and rings of device 400. Once suitable position is achieved, the components of distal end 102 may move to the engaged position as illustrated in FIG. 6H. For example, the release ring may be moved via a pull-cord and handle such that the release ring contacts an inner section of the ramp portions of the latching legs so the latching legs extend radially outward. In accordance with another aspect of the invention, the release ring may be moved via a PEEK tube as described in further detail below. A medical professional, e.g., a clinician, may verify that device 400 is engaged to apparatus 100 by slowing advancing and retracting apparatus 100 a distance, e.g., approximately 5 mm, while device 400 remains in loading cartridge 614. In addition, a clinician may verify that apparatus 100 is capable of disengaging from device 400 within loading cartridge 614 by pressing handle to cause the components at distal end 102 to disengage and then moving distal end 102 away from device 400. After such verification, the clinician may reengage apparatus 100 to device 400. Preferably, device 400 is loaded into loading cartridge 614 shortly before implantation, so as to avoid unnecessarily compressing device 400 or re-setting of the optional closed shape of leaflets, which may interfere with later deployment or operation of the device.

Referring back to FIG. 5, the device then is implanted, first by identifying the fossa ovalis of the heart septum, across which device 400 is to be deployed (step 503). Specifically, a trans-septal puncture device, e.g., a mechanical needle such as a BROCKENBROUGH needle or a radiofrequency trans-septal puncture device, may be percutaneously introduced into the right atrium via the subject's venous vasculature, for example, via the femoral artery. Then, under fluoroscopic and/or echocardiographic visualization, the needle is pressed against the fossa ovalis, at a pressure insufficient to puncture the fossa ovalis. The pressure from the needle causes "tenting" of the fossa ovalis, i.e., causes the fossa ovalis to stretch into the left atrium. Other portions of the atrial septum are thick and muscular, and so do not stretch to the same extent as the fossa ovalis. Thus, by visualizing the extent to which different portions of the atrial septum tents under pressure from the needle, the fossa ovalis may be identified, and in particular, the central portion of the fossa ovalis may be located.

The fossa ovalis (particularly its central region) may be punctured with the trans-septal puncture device, and a guidewire may be inserted through the puncture by threading the guidewire through the needle into the left atrium, and then removing the needle (step 504). The puncture through the fossa ovalis then may be expanded by advancing a dilator over the guidewire through the puncture (step 505). Alternatively, a dilator may be advanced over the trans-septal puncture device, without the need for a guidewire. The dilator is used to further dilate the puncture and a sheath then is advanced over the dilator and through the fossa ovalis; the dilator and guidewire or needle then are removed. The sheath, which may be 14 Fr., is then flushed.

Figure 6J:
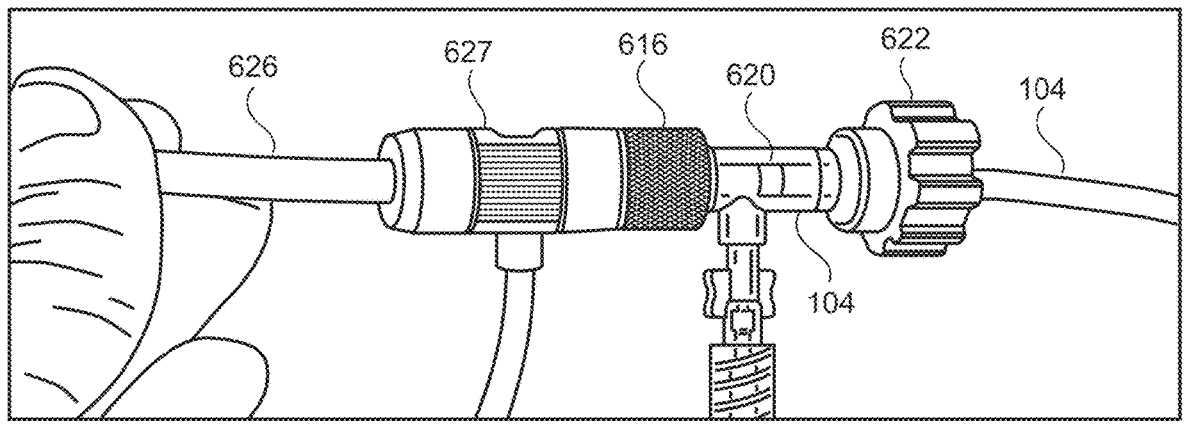
Figure 6K:
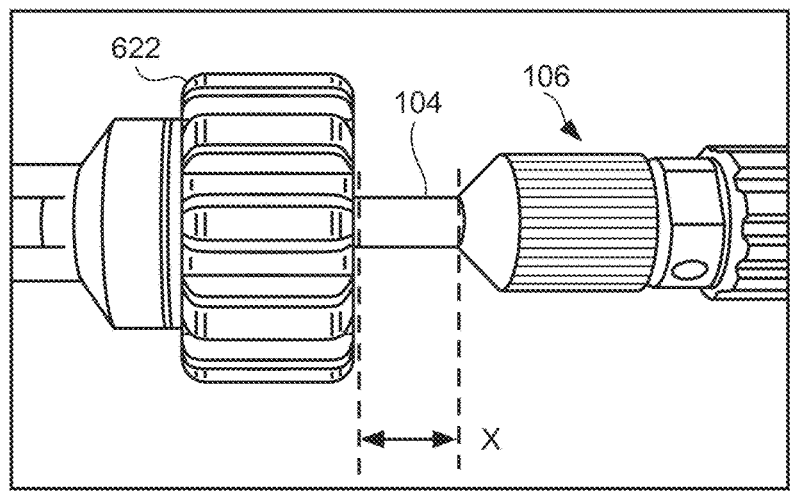

Distal end 102 of apparatus 100, with device 400 coupled thereto in a contracted, delivery state, then is advanced into the sheath (step 506). For example, the delivery system may be flushed, e.g., via fluid connected to fluid tube 630, and then loading cartridge 614 may be coupled to sheath 626, e.g., via port 627, as illustrated in FIG. 6. The clinician should verify that loading cartridge contains no air therein. In accordance with another aspect of the invention, a Tuohy Borst adapter having a Luer fitting may be used which allows for continuous flushing of the loading cartridge during connection of the loading cartridge to the hemostasis valve of the delivery sheath. Next, while holding sheath 626 in place, loading cartridge 614 is advanced distally within port 627 as illustrated in FIG. 6J. The device and delivery apparatus are advanced distally in sheath 626 until proximal end 106 of apparatus 100 is a predetermined distance X, e.g., approximately 1 cm, from knob 622 as illustrated in FIG. 6K. The delivery system again may be flushed, e.g., via fluid connected to fluid tube 630. The engagement of the latching legs of apparatus 100 with device 400 permit movement of device 400 longitudinally forward and longitudinally backward through sheath 626.

Figure 6L:
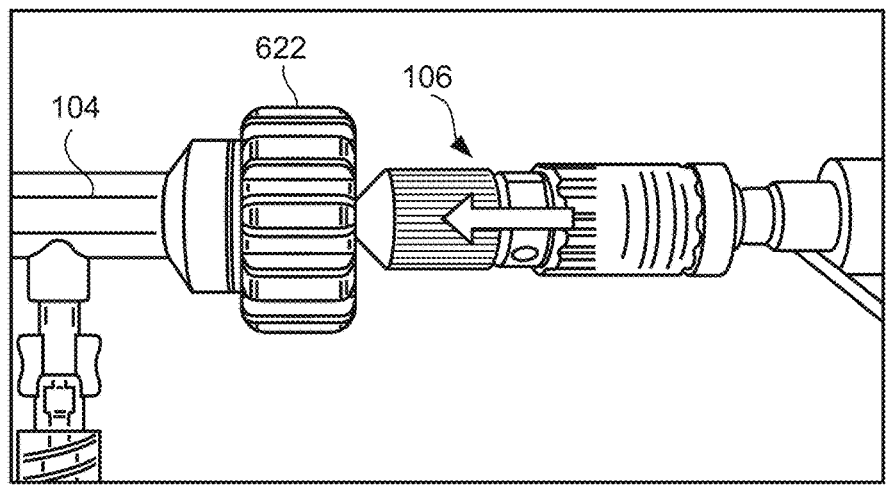
Figure 6M:
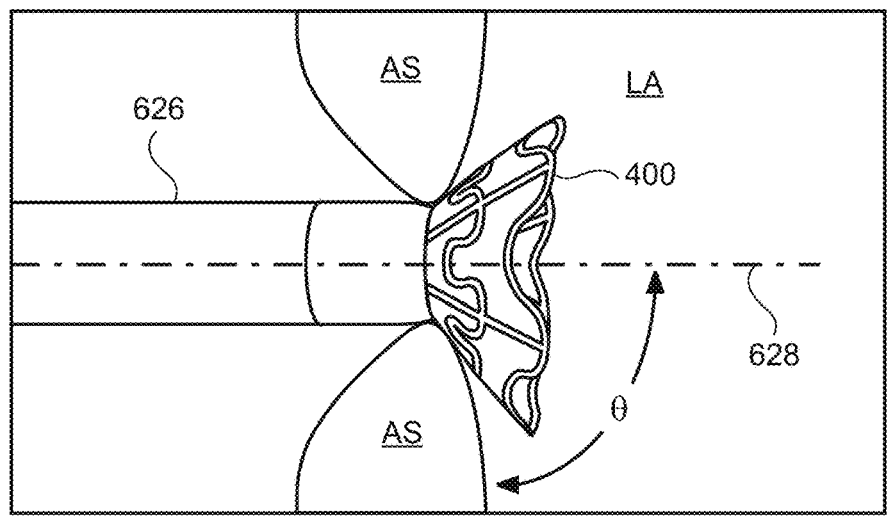
Figure 6N:
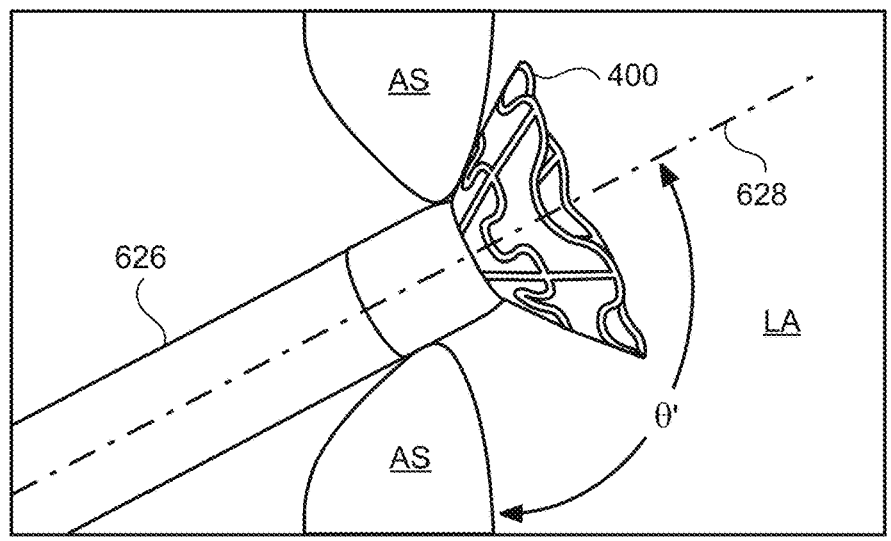

Then, under fluoroscopic and/or echocardiographic visualization, sheath 626 may be repositioned such that the distal tip of sheath 626 is disposed a predetermined distance, e.g., approximately 1-2 cm, distal to the fossa ovalis within the left atrium. Next, device 400 and apparatus 100 are advanced distally such that the device is partially advanced out of the sheath so the first flared end of the device protrudes out of the sheath and into the left atrium, and expands to its deployed state (step 507). For example, device 400 and apparatus 100 may be advanced distally until the handle at proximal end 106 contacts knob 622 as shown in FIG. 6L. In a preferred embodiment, the distance between proximal end 106 and distal end 102 of delivery device 100 is adjustable such that only the first flared end of shunt device 400 protrudes out of the sheath when the handle at proximal end 106 contacts knob 622. Such advancement causes device 400 to partially protrude out of sheath 626 and into left atrium LA, which causes the first flared end region to expand in the left atrium LA, as shown in FIG. 6M. The first flared end region of device 400 may protrude beyond the atrial septum AS into left atrium LA such that the angle θ between center axis 628 of device 400, sheath 626, apparatus 100, and/or catheter 104 and the outer surface of the atrial septum at the left atrial side below device 400 is generally perpendicular, e.g., between about 80 and about 100 degrees, between about 85 and about 95 degrees, or about 90 degrees, as shown in FIG. 6M. Alternatively, device 400 may be positioned across the atrial septum AS, e.g., across a puncture through the fossa ovalis, at a non-perpendicular angle between center axis 628 and the outer wall of the atrial septum at the left atrial side below device 400. For example, the angle θ' may be substantially greater than 90 degrees as shown in FIG. 6N. Such an angle may be appropriate when device 400, sheath 626, apparatus 100, and/or catheter 104 are advanced toward the atrial septum transapically or through the inferior vena cava. Exemplary angles θ' between center axis 628 and the outer surface of the atrial septum below device 400 include between about 110 and about 170 degrees, between about 120 and about 50 degrees, between about 130 and about 150 degrees about 120 degrees, about 125 degrees, about 130 degrees, about 135 degrees, about 140 degrees, about 145 degrees, about 150 degrees, about 155 degrees, about 160 degrees, about 165 degrees, and about 170 degrees.

Figure 6O:
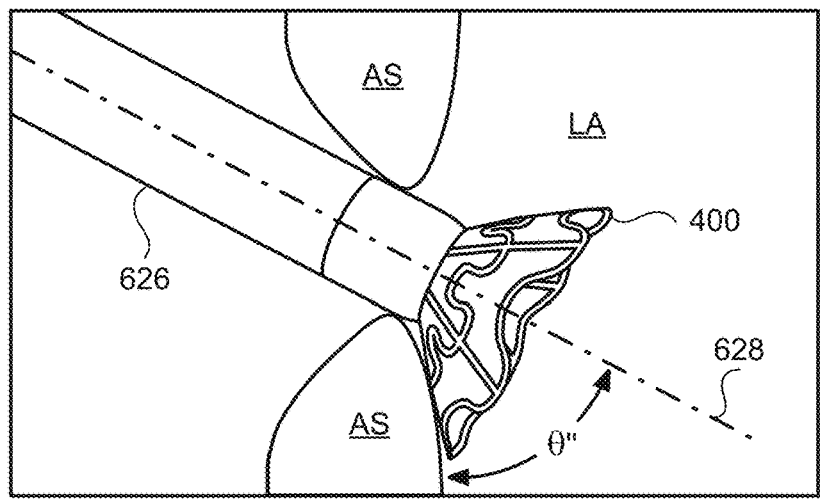

As another example, the angle θ" may be substantially less than 90 degrees as shown in FIG. 6O. Such an angle may be appropriate when device 400, sheath 626, apparatus 100, and/or catheter 104 are advanced toward the atrial septum through the superior vena cava. Exemplary angles θ" between center axis 628 and the outer surface of the atrial septum at the left atrial side below device 400 include between about 10 and about 70 degrees, between about 20 and about 60 degrees, between about 30 and about 50 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, and about 70 degrees.

An hourglass shape may aid in non-perpendicular deployment because the flared ends of the device engage the atrial septum, even when positioned at an angle relative to the central axis of the puncture through the atrial septum.

Next, under fluoroscopic and/or echocardiographic visualization, it is verified that the first flared end of the device protrudes from sheath 626 and then knob 622 of Tuohy-Borst connector 620 is used to lock the delivery system in place within the sheath 626. Sheath 626, along with the delivery system 100 are pulled proximally causing the first flared end region of device 400 to engage the left side of the atrial septum AS as shown in FIG. 6M. For example, as the latching legs of apparatus 100 are engaged with device 400 within sheath 626, device 400 is prevented from accidental deployment wholly within the left atrium LA, which may also assist in positioning the device when advanced at non-perpendicular angles as described in FIGS. 6N and 6O.

Figure 6P:
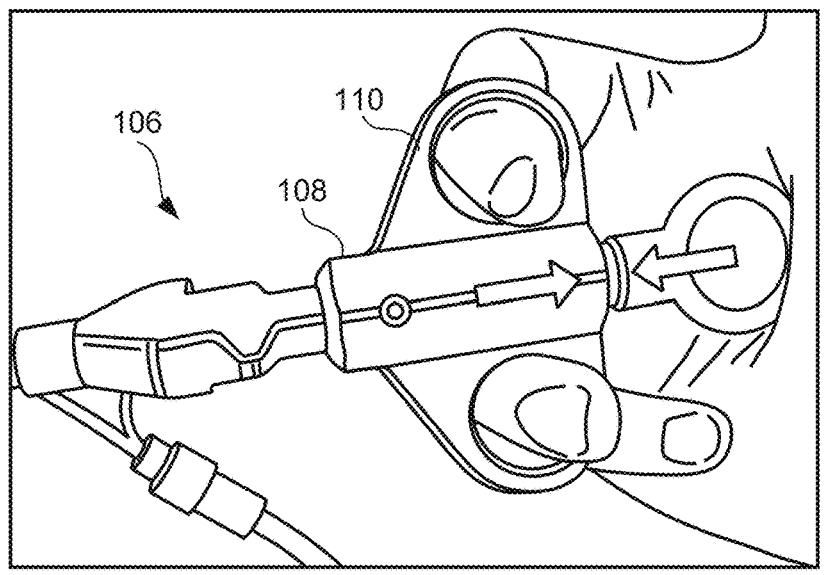

Using fluoroscopic and/or echocardiographic visualization, the clinician next verifies that the device is positioned across the fossa ovalis. The clinician then reduces the pulling force of the sheath and allows the fossa ovalis to straighten. Then, while holding sheath 626 in place, knob 622 is released and the components at distal end 102 of apparatus 100 are moved from an engaged position to a disengaged position, e.g., by actuating handle 108 as shown in FIG. 6P. Then, apparatus 100 is pulled proximally with the sheath 626 a predetermined distance, e.g., approximately 5-6 cm.

Figure 6Q:
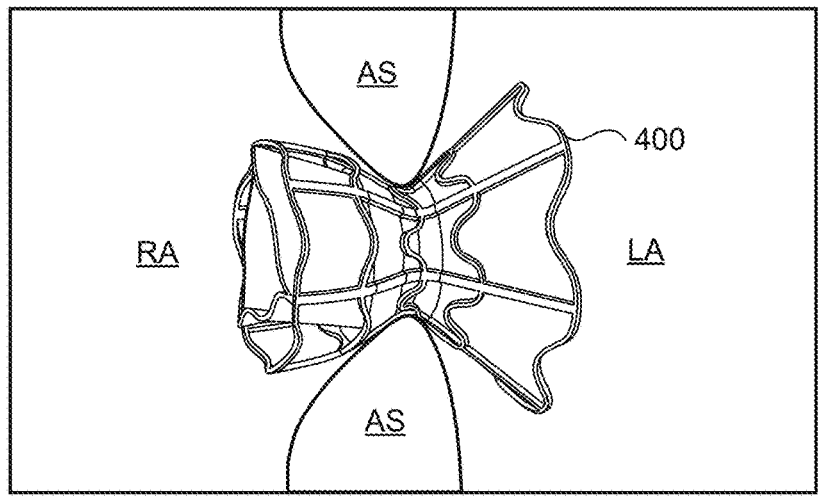

The shunt device then may be fully deployed by pulling the sheath proximally causing the first flared end region to engage the left side of the atrial septum and the neck of the device to lodge in the puncture through the fossa ovalis, and allowing expansion of the second flared end of the device into the right atrium as shown in FIG. 6Q (step 508). Any remaining components of the delivery system then may be removed, e.g., sheath and distal end of delivery apparatus (step 509). Once positioned in the fossa ovalis, the device shunts blood from the left atrium to the right atrium when the left atrial pressure exceeds the right atrial pressure (step 510), thus facilitating treatment and/or the amelioration of symptoms associated with CIF.

Figure 7A:
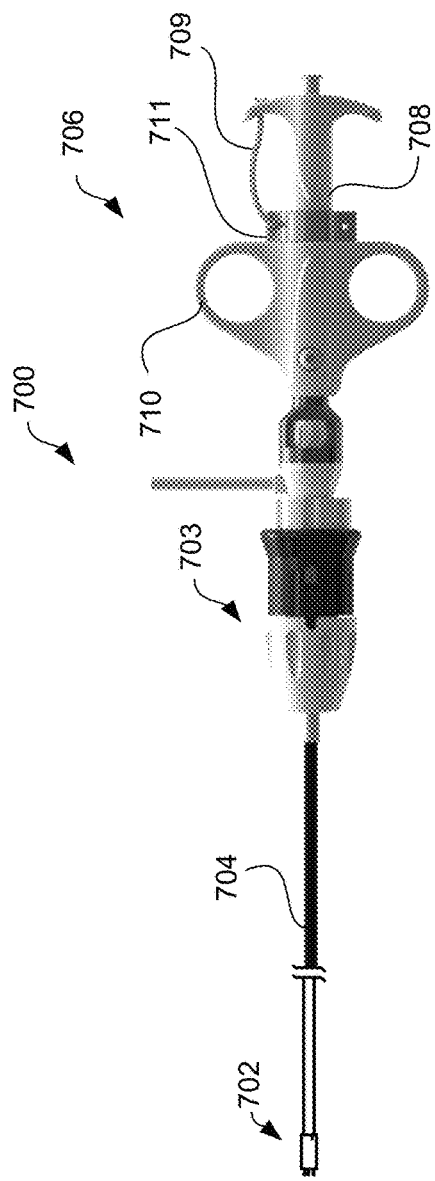
FIG. 7A illustrates a proximal end of an alternative exemplary apparatus for delivering devices in accordance with the present invention.
Figure 7B:
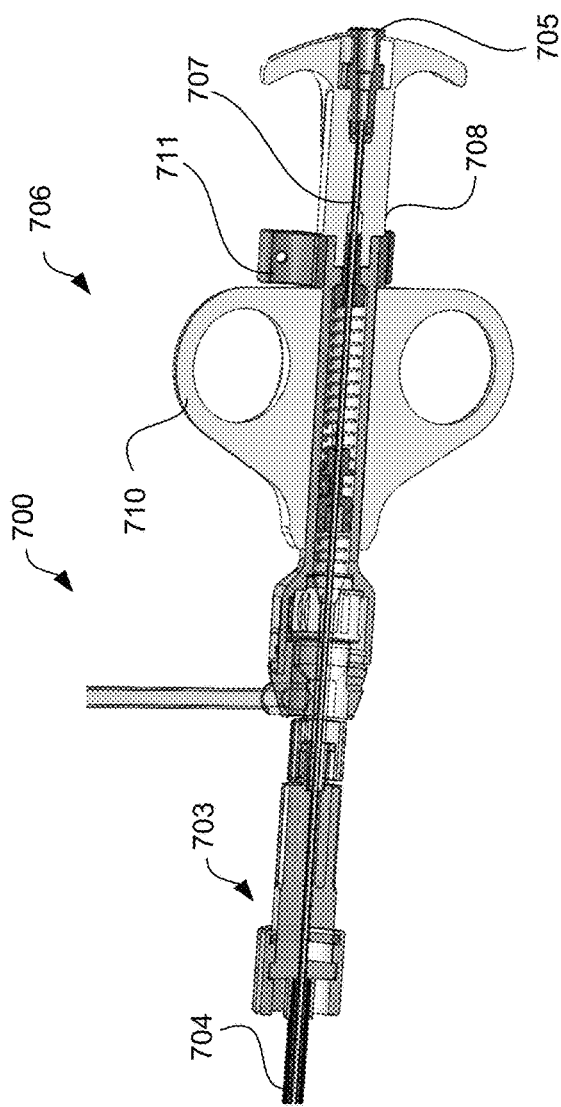
FIG. 7B illustrates a cross-sectional view of the apparatus of FIG. 7A.

Referring to FIGS. 7A and 7B, an alternative exemplary apparatus is provided for delivering interatrial shunt devices, e.g., device 400 of FIGS. 4A and 4B, and/or devices described in U.S. Pat. No. 9,629,715 to Nitzan, U.S. Pat. No. 9,713,696 to Yacoby, and U.S. Pat. No. 10,076,403 to Eigler. Apparatus 700 includes distal end 702, catheter 704, proximal end 706, and knob system 703. Distal end 702 comprises components suitable for coupling apparatus 700 to devices of the present invention, as described in detail below. Catheter 704 comprises a biocompatible tube shaft of suitable size, e.g., approximately 14 Fr., and suitable length, e.g., approximately 75-100 cm and preferably 85 cm. Proximal end 706 includes handle 708 that is designed to be manipulated, e.g., by a human hand, to transition components in distal end 702 from an engaged position to a disengaged position. In addition, apparatus 700 includes Luer connector 705 in communication with control tube 707 extending from proximal end 706 to distal end 702 of apparatus 100. For example, control tube 707 may extend through catheter 704 and through handle 708 for over-the-wire flushing, e.g., via a Tuohy Borst adapter connected to apparatus 700. Control tube 707 has a lumen extending therethrough sized to receive a guidewire.

Like handle 108, handle 708 may be manipulated, for example, by moving finger grips 710 proximally from a locked position shown to an unlocked position. In addition, handle 708 may be manipulated by moving finger grips 710 distally from the locked position to the unlocked position so as to transition components in distal end 702 from the disengaged position to the engaged position to load devices of the present invention. Handle 708 also may include securement mechanism 709 coupled to handle safety lock 711 such that finger grips 710 cannot be moved until handle safety lock 711 is released. Upon activation, handle 708 is retained in position, enabling a single user to perform the procedure.

Figure 8C:
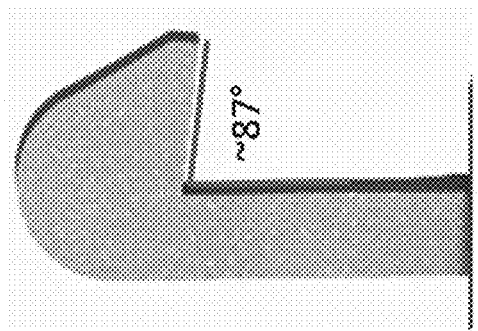
FIG. 8C illustrates the hook portion of the distal end of the alternative exemplary apparatus of FIGS. 8A and 8B.
Figure 8A:
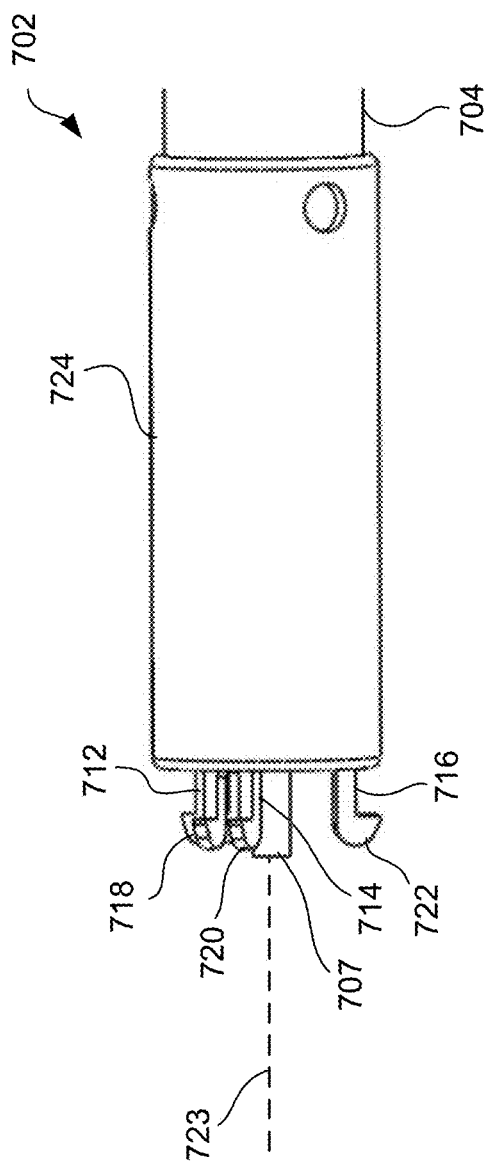
FIGS. 8A and 8B, respectively, illustrate the distal end of the alternative exemplary apparatus of FIGS. 7A and 7B in an engaged position and a disengaged position.
Figure 8B:
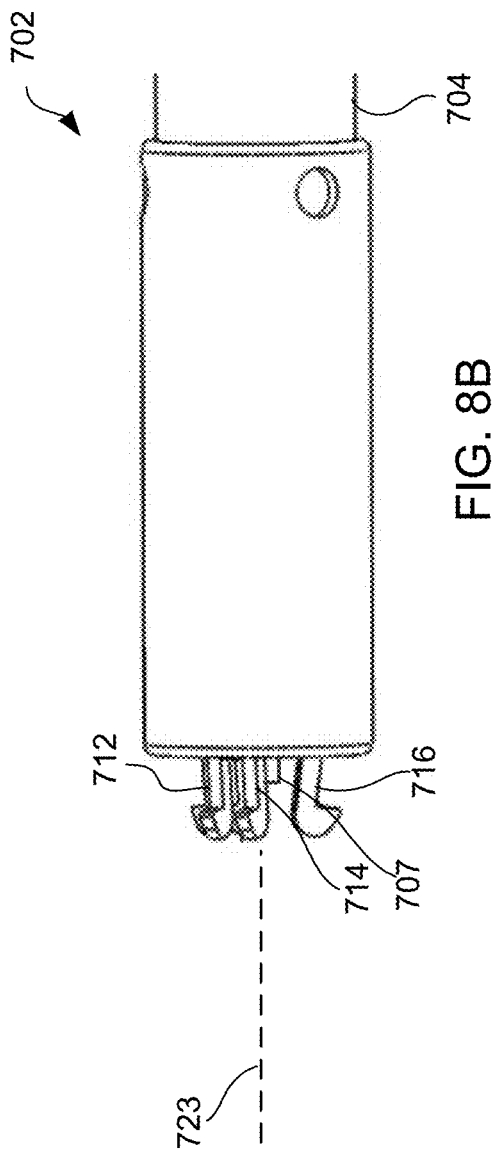

FIGS. 8A and 8B illustrate distal end 702 in the engaged position and the disengaged position, respectively. At distal end 702, apparatus 700 may include latching legs 712, 714, and 716 having hook portions 718, 720, and 722, respectively. Latching legs 712, 714, and 716 comprise a biocompatible material such as a biocompatible metal or polymer, and are positioned longitudinally and radially so as to firmly secure devices of the present invention for delivery. Hook portions 718, 720, and 722 extend outwardly from the distal end of latching legs 712, 714, and 716, respectively, and are configured to fit securely between struts and rings of the devices of the present invention. Preferably, hook portions 718, 720, and 722 hook outwardly away from center axis 723 of catheter 704 in both the engaged and disengaged positions as shown in FIGS. 8A and 8B. Center axis 723 is centered relative to catheter 704 on both a longitudinal and cross-sectional basis. By facing outwardly from center axis 723, hook portions 718, 720, and 722 may engage the inner surface of the device, e.g., within a lumen of a shunt.

In one embodiment, hook portions 718, 720, and 722 move generally radially away from center axis 723. The angle between the lower surface of the hook portion and the longitudinal axis of the latching leg is preferably less than 90 degrees and greater than 75 degrees, e.g., 87 degrees, as shown in FIG. 8C to enable a more secure engagement with the shunt. For example, an angle less than 75 degrees could result in failure to disengage the shunt from the delivery device after deployment, whereas an angle greater than 90 degrees could result in failure to achieve half-way retrieval of the shunt by the delivery device. Such improved engagement allows the delivery device to pull the distal flange of a half-deployed shunt back into the sheath ("halfway-retrieval") in the event the shunt's distal flange is deployed in an undesired location. As will be readily understood by one of ordinary skill in the art, while three latching legs are illustrated, more or fewer latching legs may be used without departing from the scope of the present invention. For example, one, two, four, five, six, or more latching legs may be used.

Catheter 704 may include cover tube 724 which may have a larger diameter than the remaining shaft of catheter 704. Cover tube 724 comprises a biocompatible material such as a biocompatible metal or polymer, and may be the same or different material than the remaining shaft of catheter 704. Components at distal end 702, such as latching legs 712, 714, and 716, may be at least partially disposed within cover tube 724. Referring back to FIGS. 8A and 8B, distal end 702 includes control tube 707, e.g., a polyether ether ketone (PEEK) tube, having a lumen extending therethrough sized to receive a guidewire, as described in more detail below. Control tube 707 is moveable between an engaged position, where the distal end of control tube 707 extends past the distal end of cover tube 724 as shown in FIG. 8A, and a disengaged position, where the distal end of control tube 707 is moved proximally, but still extends past the distal end of cover tube 724 as shown in FIG. 8B.

Referring now to FIGS. 9A to 9D, the inner components at distal end 702 of apparatus 700 are described. FIGS. 9A and 9B respectively illustrate distal end 702 in the engaged position of FIG. 8A and the disengaged position of FIG. 8B, respectively. As shown in FIG. 9A, catheter 704 and cover tube 724 comprise lumens 726 and 728, respectively, for housing the inner components. Latching legs 712 and 714 share common ramp portion 730 having inner section 732 and outer section 734 while latching leg 716 has separate ramp portion 736 having inner section 738 and outer section 740. Inner sections 732 and 738 are angled so as to be positioned closer to central axis 723 of catheter 704 and cover tube 724 relative to the positions of outer sections 734 and 740. Latching legs may also include jogs and protrusions. For example, latching leg 716 illustratively includes protrusion 742 proximal to ramp portion 736, and jog 744 between hook portion 722 and ramp portion 736. Protrusion 742 is configured to contact the distal surface of annular member 748 to maintain suitable positioning of latching leg 716. Jog 744 is shaped to prevent release ring 746 from moving too far distally.

Release ring 746 is coupled to latching legs 712, 714, and 716. For example, latching legs 712, 714, and 716 may be partially disposed within release ring 746 as illustrated in FIGS. 9A to 9D. Release ring 746 is moveable within cover tube 724. Release ring 746 may be located in a first position, e.g., an engaged position, where release ring 746 contacts inner sections 732 and 738 of ramp portions 730 and 736 such that latching legs 712, 714, and 716 extend radially outward as shown in FIGS. 9A and 9C. Release ring 746 may be moved to a second position, e.g., a disengaged position, where release ring 746 contacts outer sections 734 and 740 of ramp portions 730 and 736 such that latching legs 712, 714, and 716 move radially inward as shown in FIGS. 9B and 9D. In one embodiment, release ring 746 is configured to move from the second position to the first position to load a device of the present invention and to move from the first position to the second position to release the device.

Annular member 748 may be partially disposed in the proximal end of cover tube 724 and configured to couple cover tube 724 to catheter 704 via a suitable coupling mechanism, e.g., teeth 750, ribs. Annular member 748 includes lumen 752 sized to accept control tube 707 therethrough.

Control tube 707 is coupled to release ring 746 and actuation of control tube 707 moves release ring 746 from the first position shown in FIG. 9A to the second position shown in FIG. 9B, and vice versa. In a preferred embodiment, control tube 707 is coupled to handle 708 such that control tube 707 is actuated by moving finger grips 710 from a locked position to an unlocked position, and vice versa. In addition, control tube 707 includes lumen 755 extending therethrough sized to receive a guidewire such that distal end 702 of apparatus 700 may be advanced over a guidewire to the desired device deployment location. The over-the-wire capability enables safe retrieval of a fully embolized device.

Control tube 707 may be coupled to release ring 746 via release ring base 756. In this embodiment, release ring base 756 is directly coupled to release ring 746 and control tube 707 such that actuation of control tube 707 moves release ring base 756 to move release ring 746 from the first position the second position, and vice versa.

Spring 758 may be coupled to the proximal surface of release ring base 756 and the distal surface of annular member 748 such that release ring base 756 and annular member 748 maintain spring 758 therebetween. Spring 758 is configured to bias release ring 746 towards a particular position such as towards the first position as shown in FIG. 9A.

FIGS. 9A and 9C illustrate the components at distal end 702 in an engaged position, where FIG. 9C omits cover tube 724 for clarity. As control tube 707 is actuated, e.g., via handle 708, release ring 746 is moved, e.g., via release ring base 756, from the engaged position to the disengaged position shown in FIGS. 9B and 9D, where FIG. 9D omits cover tube 724 for clarity. Release ring 746 slides along ramp portions 730 and 736 from inner sections 732 and 738 to outer sections 734 and 740 such that latching legs 712, 714, and 716 move from being extended radially outward to being positioned radially inward. As release ring 746 moves from the engaged position to the disengaged position, spring 758 is compressed and as release ring 746 moves from the disengaged position to the engaged position, spring 758 is decompressed.

Figure 10B:
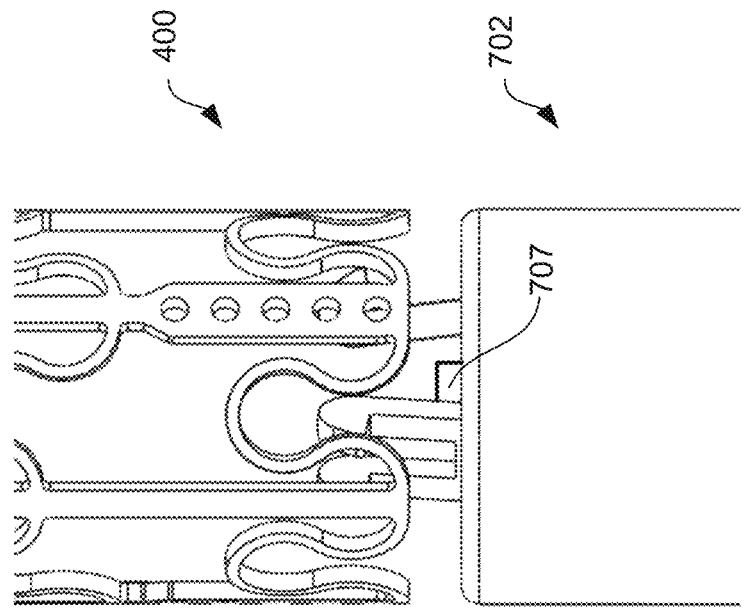
FIG. 10B illustrates the alternative exemplary apparatus disengaged from the exemplary device.
Figure 10A:
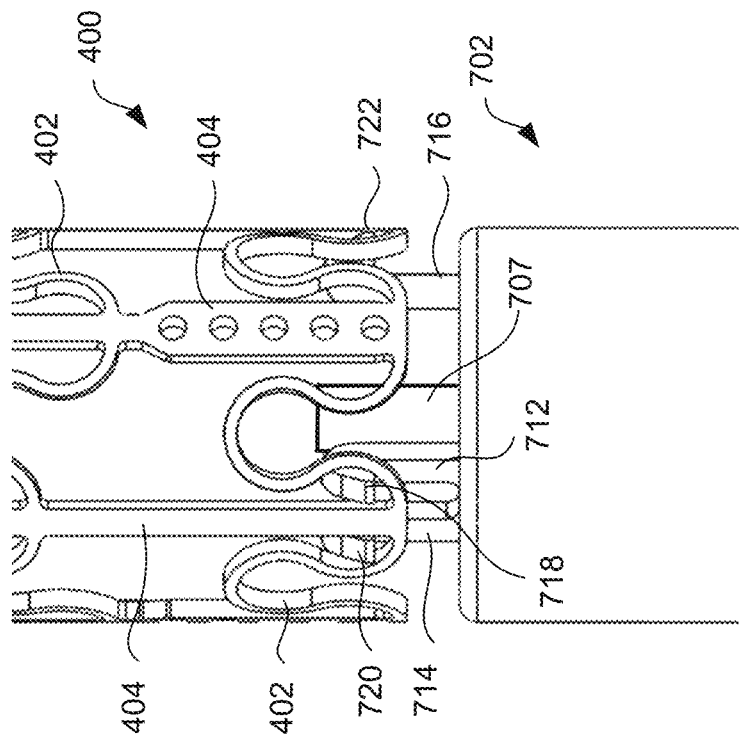
FIG. 10A illustrates the distal end of the alternative exemplary apparatus of FIGS. 8A and 8B engaged to an exemplary device, partially shown, in accordance with the present invention

FIG. 10A illustrates the components at distal end 702 of apparatus 700 engaged to an exemplary interatrial shunt device and FIG. 10B illustrates the components disengaged from the exemplary device. Device 400 includes rings 402 and struts 404 and may be constructed similar to devices described in U.S. Pat. No. 9,629,715 to Nitzan, U.S. Pat. No. 9,713,696 to Yacoby, and U.S. Pat. No. 10,076,403 to Eigler. As shown in FIG. 10A, latching legs 712, 714, and 716 are sized, shaped, angled, and spaced apart from one another so as to engage device 400 in openings between rings 402 and struts 404 when device 400 is in a contracted, delivery state. Hook portions 718, 720, and 722 also are sized, shaped, and angled to fit between rings 402 and struts 404 and hook portions 718, 720, 722 hook outwardly away from the center axis at the distal end of the delivery apparatus such that hook portions 718, 720, 722 are disposed in the lumen of device 400 in the engaged position of FIG. 10A and engage at the inner surface of device 400. Preferably, hook portions 718, 720, and 722 move radially away from center axis 723 at an angle less than 90 degrees, e.g., 87 degrees, toward proximal end 706 of apparatus 700 as shown in FIG. 8C to enable halfway retrieval of a partially deployed device. As shown in FIG. 10B, latching legs 712, 714, and 716 are configured to move radially inward a sufficient distance to decouple hook portions 718, 720, and 722 from device 400 in the disengaged position, thereby releasing device 400 for implantation.

Figure 11:
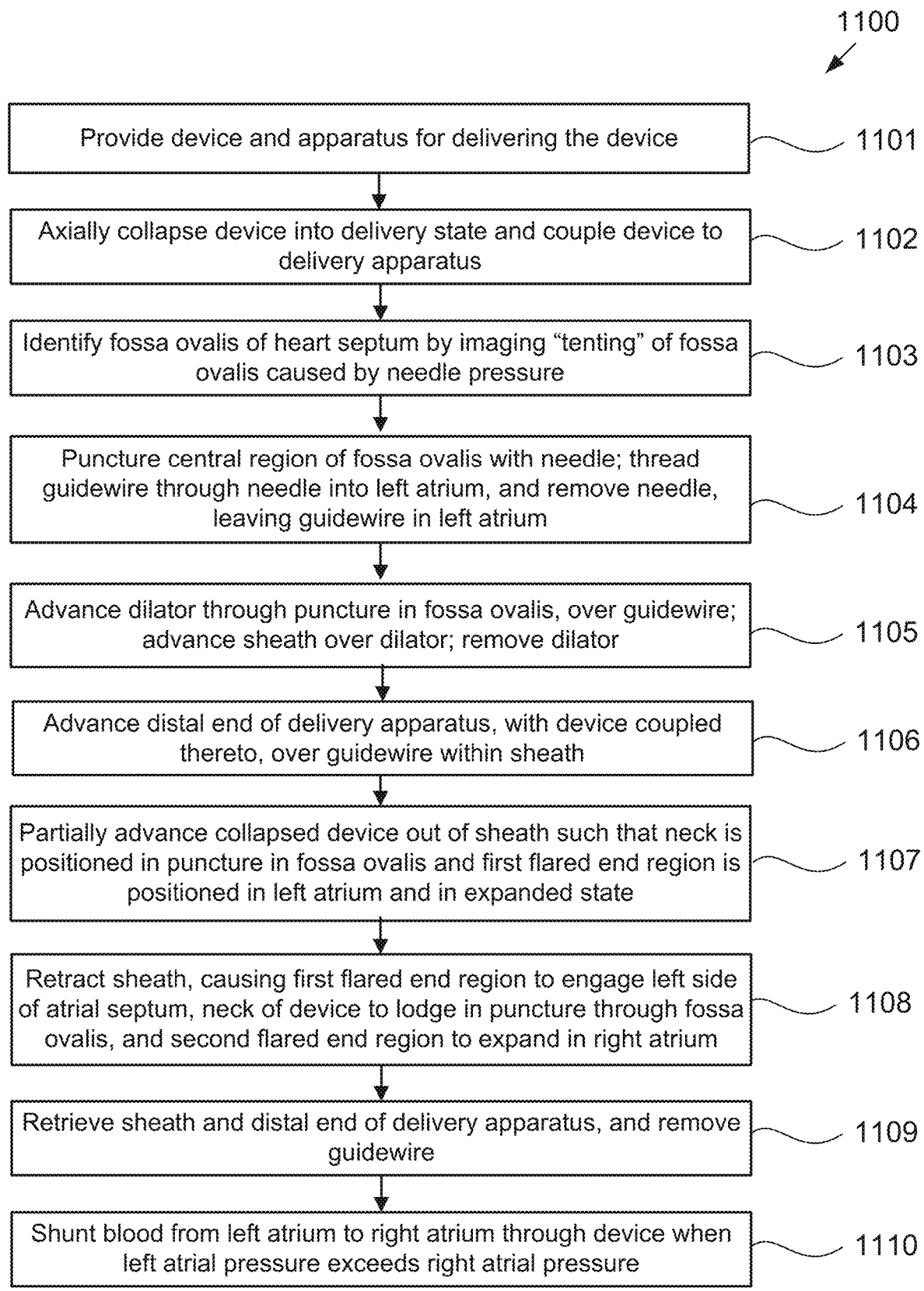
FIG. 11 is a flow chart of steps in an exemplary method of percutaneously implanting an hourglass-shaped device in a puncture through the fossa ovalis using the alternative exemplary apparatus of FIGS. 7A and 7B, according to some embodiments of the present invention.

FIG. 11 is a flowchart of exemplary method 1100 of delivering device 400 to reduce left atrial pressure in a subject, for example, a human having a heart condition, using apparatus 700 illustrated in FIGS. 7A and 7B. Steps 1101-1104 are similar to steps 501-504 described in FIG. 5, except that apparatus 700 is used instead of apparatus 100, and for brevity are not discussed again here. At step 1105, a dilator having a guidewire lumen sized and shaped to receive the guidewire therethrough is advanced over the guidewire across the atrial septum through the fossa ovalis into the left atrium. A sheath is then advanced over the dilator across the atrial septum through the fossa ovalis into the left atrium. The dilator is then removed. In accordance with another aspect of the present invention, a sheath having a dilator disposed therein may be advanced together over the guidewire across the atrial septum through the fossa ovalis into the left atrium.

At step 1106, distal end 702 of apparatus 700, with device 400 coupled thereto, is advanced through the sheath over the guidewire until proximal end 706 of apparatus 700 is a predetermined distance from the proximal end of the sheath such that distal end 702 of apparatus 700 is a predetermined distance from the distal end of the sheath. The guidewire is received from the Luer connector 705 via lumen 755 of control tube 707. Steps 1107-1110 are similar to steps 507-510 described in FIG. 5, except that apparatus 700 is used instead of apparatus 100 and the guidewire may be removed through Luer connector 705 at step 1109, and for brevity are not described again herein. Thus, for example, the components at distal end 702 of apparatus 700, e.g., latching legs 712, 714, and 716, are moved from an engaged position to a disengaged position, e.g., by actuating the handle at proximal end 706 to decouple hook portions 718, 720, and 722 from device 400 in the disengaged position, before the sheath is retracted to deploy device 400 within the atrial septum.

Figure 12A:
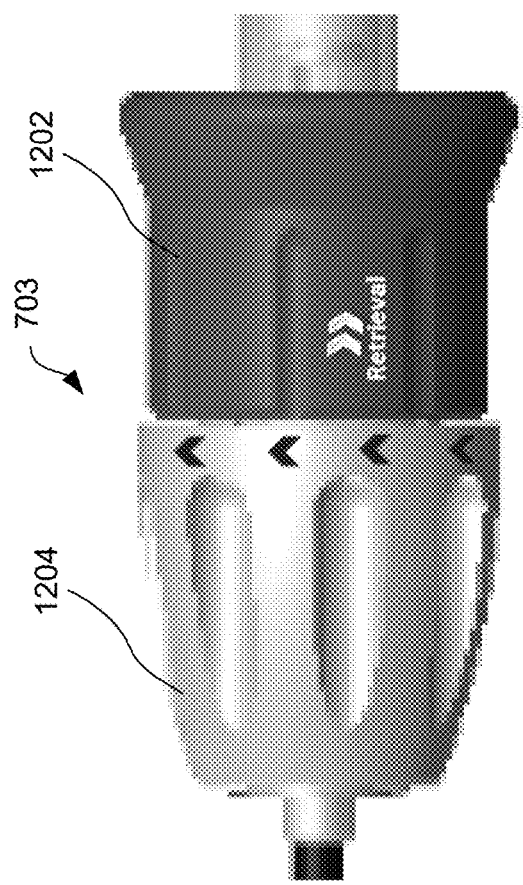
FIGS. 12A to 12C illustrate the knob system at the proximal end of the alternative exemplary apparatus of FIGS. 7A and 7B in accordance with the present invention.

In accordance with another aspect of the present invention, knob system 703 may be used for length adjustment of apparatus 700 relative to the sheath during deployment of device 400 at the atrial septum, e.g., to assist in halfway retrieval of device 400. For example, referring now to FIGS. 12A-12C, knob system 703 includes proximal knob 1202, distal knob 1204, and optional lock nut 1206. Referring to FIG. 12A, proximal knob 1202 may be pulled proximally to enable rotating distal knob 1204 clockwise to assist in "halfway retrieval" of device 400 as described here. Distal knob 1204 is rotatable to shorten the distance between the knob 1204 and the distal end 702 of apparatus 700, thus pulling distal end 702 proximally within the sheath. For example, in the event that the first flared end region of device 400 is deployed and the second flared end region is still in a collapsed state within the sheath and coupled to distal end 702 of apparatus 700, distal knob 1204 may be rotated clockwise to retract distal end 702, and thus device 400, within the sheath. As distal end 702 is retracted within the sheath, device 400 is also retracted, thus causing the first flared end region to collapse into the sheath.

Figure 12C:
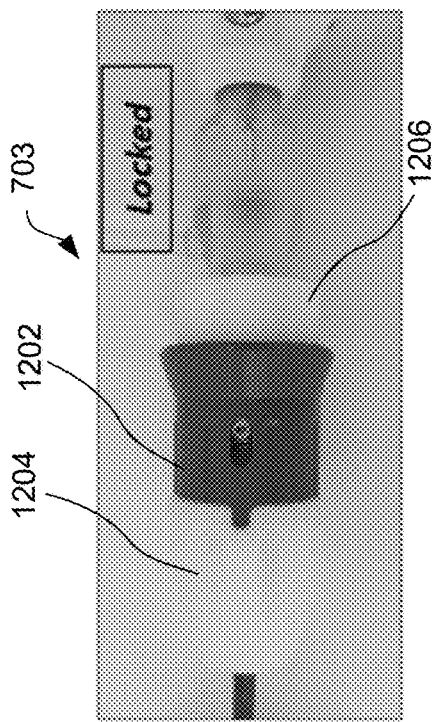
Figure 12B:
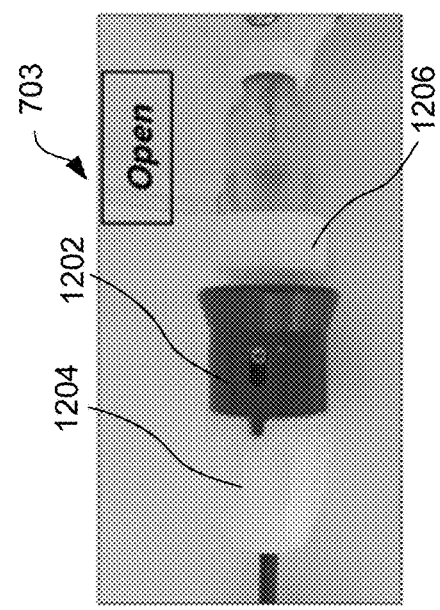

Referring now to FIGS. 12B and 12C, lock nut 1206 is moveable between an open and closed position to permit retraction of proximal knob 1202, and thereby rotation of distal knob 1204. Referring to FIG. 12B, lock nut 1206 is in an open position such that proximal knob 1202 may be pulled proximally and distal knob 1204 may be rotated to the adjust the length of catheter 704 relative to the length of the sheath. When the length of catheter 704 relative to the length of the sheath is at the desired amount, lock nut 1206 may be moved to the closed position as shown in FIG. 12C to fix the set length.

Figure 13:
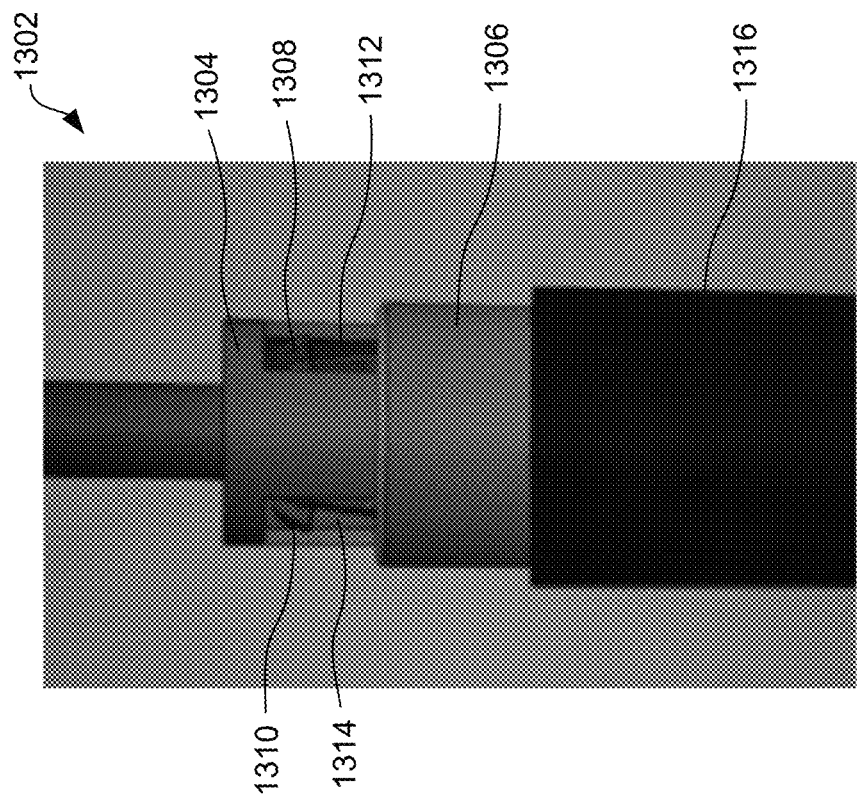
FIG. 13 illustrates an alternative embodiment of the distal end of the delivery apparatus constructed in accordance with the principles of the present invention, wherein the engagement mechanism for coupling the delivery system to the shunt is embedded within a tube to better ensure the disengagement of the shunt from the engagement hooks following its deployment.

Referring to FIG. 13, an alternative distal end of an apparatus for delivering devices of the present invention is provided. Distal end 1302 is constructed similar to distal end 102 described in FIGS. 2A to 3D, or distal end 702 described in FIGS. 8A to 9D, except that distal end 1302 includes tube 1304 extending distally from cover tube 1306. Thus, distal end 1302 includes hook portions 1308 and 1310 that move away from a center axis of the catheter as described above, and tube 1304 includes windows 1312 and 1314 sized for hook portions 1308 and 1310 to protrude through in the engaged position as described in FIGS. 2A, 3A, 3C, 8A, 9A, and 9C to engage device 400 in a collapsed state within sheath 1316. As shown in FIG. 13, when hook portions 1308 and 1310 are in the disengaged position as described in FIGS. 2B, 3B, 3D, 8B, 9B, and 9D, hook portions 1308 and 1310 do not extend beyond the diameter of tube 1304 which prevents the risk of entanglement. As will be readily understood by one of ordinary skill in the art, while two latching legs are illustrated, more or fewer latching legs may be used without departing from the scope of the present invention. For example, one, three, four, five, six, or more latching legs may be used, and accordingly, tube 1304 may include a corresponding number of windows.

Figure 14:
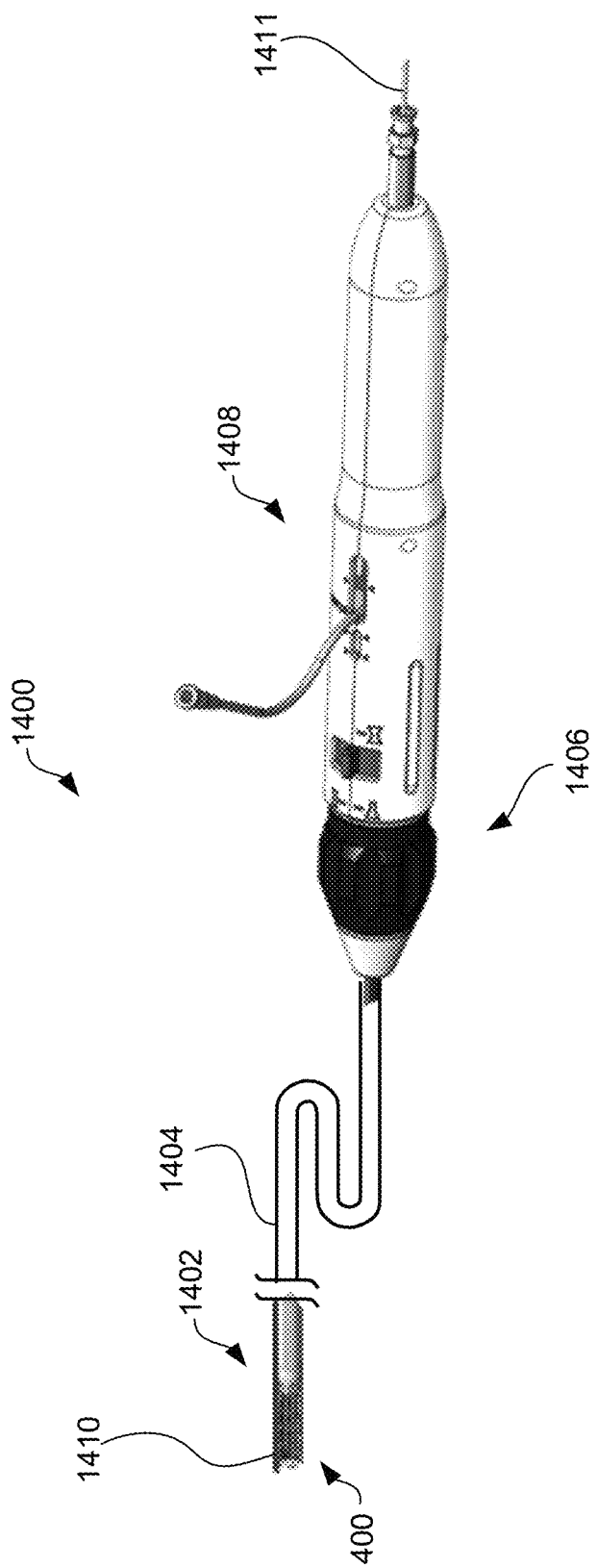
FIG. 14 illustrates yet another alternative exemplary apparatus for delivering devices in accordance with the present invention.

Referring to FIG. 14, an alternative exemplary apparatus is provided for delivering interatrial shunt devices, e.g., device 400 of FIG. 4A, 4B or 6Q, and/or devices described in U.S. Pat. No. 9,629,715 to Nitzan, U.S. Pat. No. 9,713,696 to Yacoby, and U.S. Pat. No. 10,076,403 to Eigler. Apparatus 1400 includes distal end 1402, catheter 1404, and proximal end 1406 having handle 1408 for actuating distal end 1402. Distal end 1402 is sized and shaped to be advanced through sheath 1410, which is sized to extend between distal end 1402 and proximal end 1406 over catheter 1404. Apparatus 1400 may include inner catheter 1411 extending from distal end 1402 through catheter 1404 and through proximal end 1406, e.g., past the proximal most part as shown. Inner catheter 1411 has a lumen sized to receive a guidewire therethrough.

Figure 15:
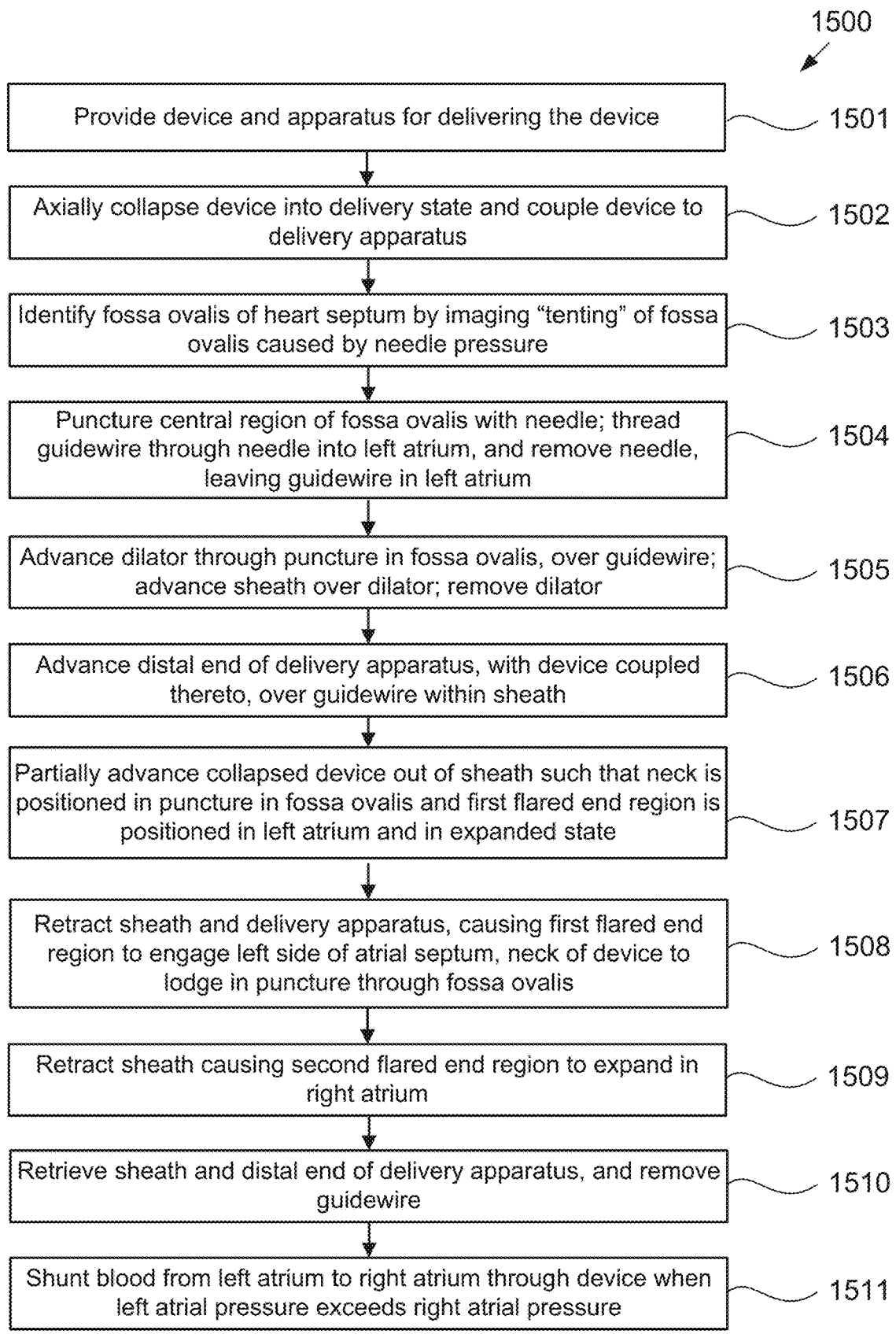
FIG. 15 is a flow chart of steps in an exemplary method of percutaneously implanting an hourglass-shaped device in a puncture through the fossa ovalis using the alternative exemplary apparatus of FIG. 14, according to some embodiments of the present invention.
Figure 16A:
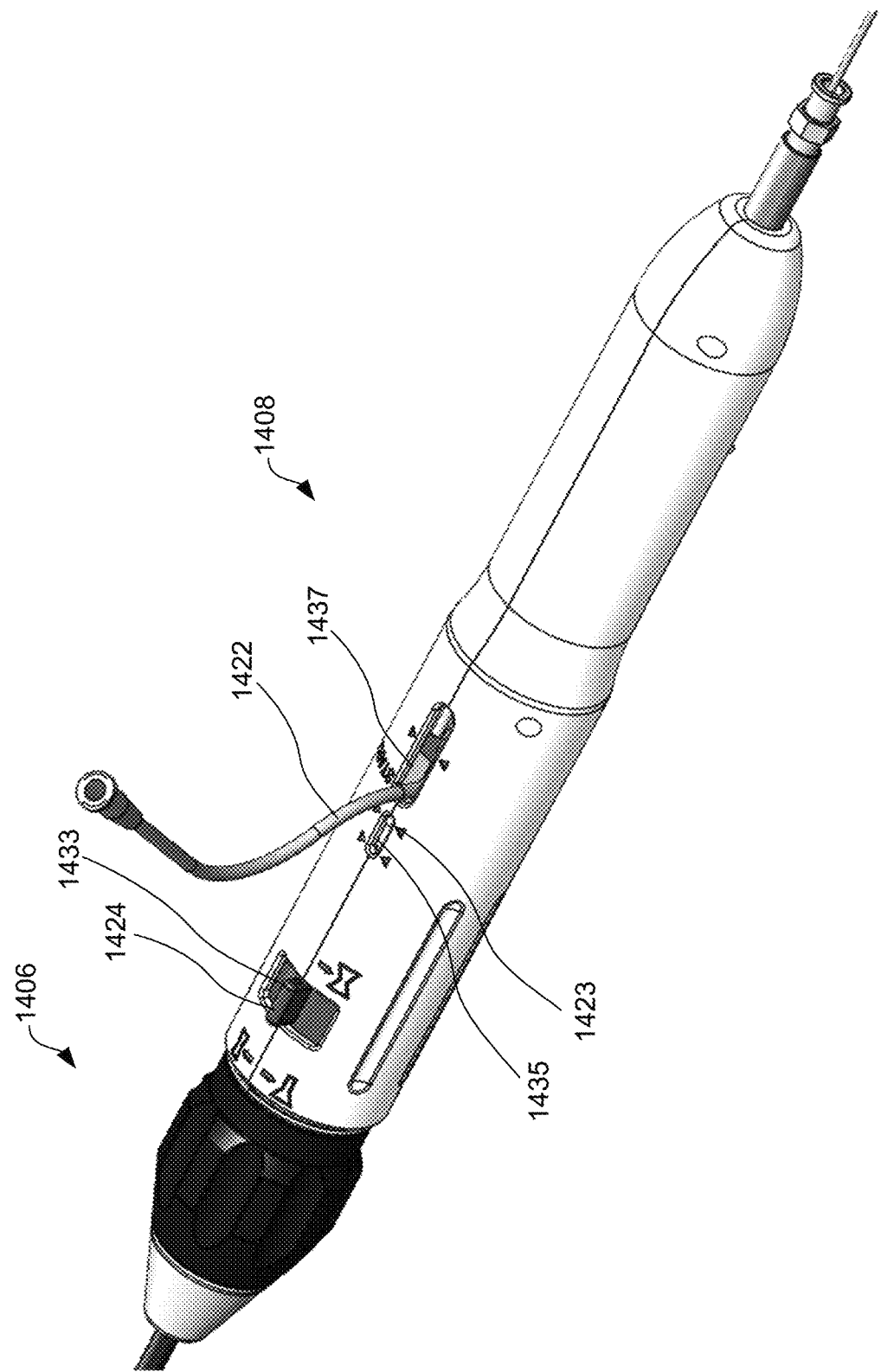
FIGS. 16A-16T schematically illustrate steps taken during the method of FIG. 15, according to some embodiments of the present invention.
Figure 16B:
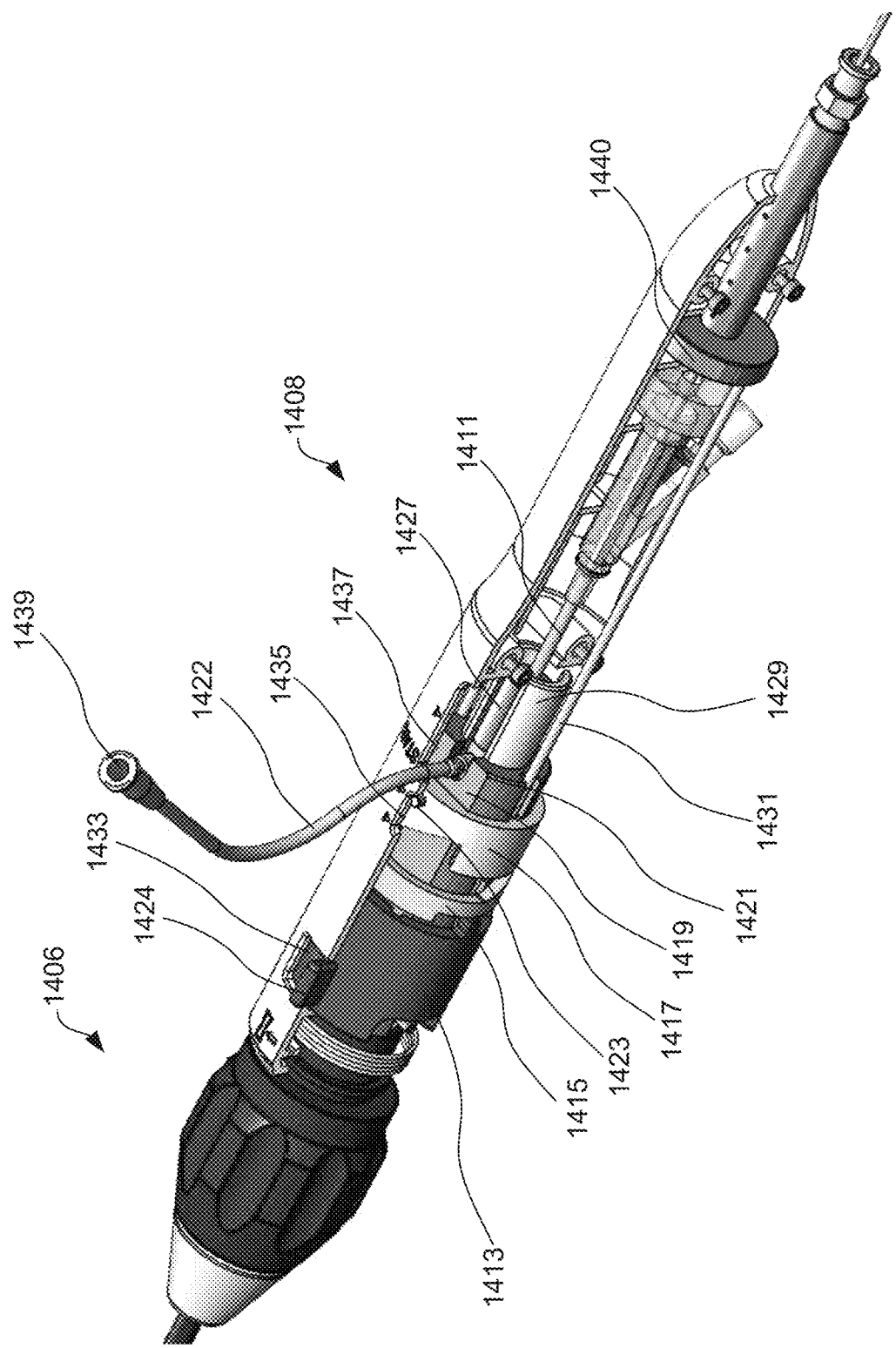

Exemplary method 1500 of delivering device 400 to reduce left atrial pressure in a subject, for example, a human having a heart pathology, using apparatus 1400 illustrated in FIG. 14 will now be described with reference to FIG. 15. Some of the steps of method 1500 may be further elaborated by referring to FIGS. 16A-16T. Steps 1501-1507 are similar to steps 1101-1107 described in FIG. 11, except that apparatus 1400 is used instead of apparatus 700, and thus for brevity these steps are not discussed again here. FIG. 16A is a perspective view of proximal end 1406 of apparatus 1400 and FIG. 16B is a partial cross-sectional view illustrating internal components. FIGS. 16A and 16B illustrate handle 1408 at proximal end 1406 of apparatus 1400 when distal end 1402 having device 400 coupled thereto, and catheter 1404 are advanced over the guidewire and through sheath 1410 across the fossa ovalis (step 1506). Handle 1408 includes first actuator 1422, second actuator 1423, and third actuator 1424 for actuating the components within the distal region of sheath 1410 such that the shunt transitions between a contracted delivery state, to a partially expanded state, and then to a fully expanded deployed state. First, second, and third actuators 1422, 1423, and 1424 may be buttons, switches, levers, touchscreens, or the like. First, second, and third actuators 1422, 1423, and 1424 may be combined into a single component, two components, or may be more than three components.

In addition, handle 1408 includes knob 1401. The inner components of knob 1401 includes a threaded portion that corresponds with a threaded portion coupled to sheath 1410. Accordingly, as knob 1401 is rotated about the longitudinal axis of handle 1408, rotational movement of knob 1401 is converted to translational movement of the threaded portion coupled to sheath 1410 along the longitudinal axis of handle 1408, thereby causing movement of sheath 1410 relative to catheter 1404. This permits gradual adjustment of the length of sheath 1410 relative to catheter 1404, and accordingly halfway-retrieval of device 400 when device is halfway deployed as will be described in further detail below. Knob 1401 may not be rotated until third actuator 1424 is moved from a locked position to an unlocked position.

As illustrated in FIG. 16B, third actuator 1424 may be coupled to third actuator component 1413 rotatable about the longitudinal axis of handle 1408, parallel to inner catheter 1411, between a first, second, and third position. For example, FIGS. 16A and 16B illustrate third actuator 1424 in the first position, such that third actuator 1424 is centered within opening 1433 of the housing of handle 1408. Third actuator component 1413 may include a toothed pattern along its proximal end for engaging with a corresponding indent along the distal end of actuator ring 1415, wherein actuator ring 1415 is freely rotatable about the longitudinal axis of handle 1408. As shown in FIG. 16B, there is a defined space between an edge of the tooth of third actuator component 1413 and an edge of the indent of actuator ring 1415 when third actuator 1424 is in the first position. When third actuator 1424 is moved to the third position, such that third actuator component 1413 is rotated, e.g., clockwise, about the longitudinal axis of handle 1408, the edge of the tooth of third actuator component 1413 engages with the edge of the indent of actuator ring 1415. This prevents actuator ring 1415 from rotating in an opposite direction, e.g., counter-clockwise, about the longitudinal axis of handle 1408. Thus, second actuator 1423 and second actuator component 1417 are also prevented from moving distally within opening 1435 along the longitudinal axis of handle 1408.

When third actuator 1424 is moved to the second position, such that third actuator component 1413 is rotated, e.g., counter-clockwise, about the longitudinal axis of handle 1408, the space between the edge of the tooth of third actuator component 1413 and the edge of the indent of actuator ring 1415 increases such that actuator ring 1415 is free to rotate in the same direction, e.g., counter-clockwise until the edge of the indent of actuator ring 1415 engages with the edge of the tooth of third actuator component 1413. In addition, third actuator component 1413 is operatively coupled to a locking mechanism between inner catheter 1411 and a hub disposed within the distal region of sheath 1410 as described in further detail below.

Actuator ring 1415 also may include a grooved pattern along its proximal end for engaging with a corresponding indent along the distal end of second actuator component 1417 coupled to second actuator 1423. Accordingly, the edge of the tooth of third actuator component 1413 may further engage with the indent of actuator ring 1415, to thereby rotate actuator ring 1415 until the groove of actuator ring 1415 engages with the indent of second actuator component 1417. Second actuator 1423 may be moveable between a first and second position. For example, FIGS. 16A and 16B illustrate second actuator 1423 in the first position, such that first actuator 1422 is positioned proximally relative to opening 1435 of the housing of handle 1408. Third actuator component 1413, actuator ring 1415, and second actuator component 1423 include a lumen sized and shaped to receive first actuator component 1419 coupled to first actuator 1422. In addition, the lumens of third actuator component 1413 and actuator ring 1415 are sized and shaped to permit rotation about first actuator component 1419, whereas the lumen of second actuator component 1417 may be sized and shaped such that second actuator component 1417 is only permitted to move longitudinally along first actuator component 1419.

First actuator component 1419 is moveable along the longitudinal axis of handle 1408, parallel to inner catheter 1411, between a first and second position. For example, FIGS. 16A and 16B illustrate first actuator 1422 in the first position, such that first actuator 1422 is positioned distally relative to opening 1437 of the housing of handle 1408. As illustrated in FIG. 16B, first actuator component 1419 may include one or more lumens 1421 sized and shaped to receive one or more guiderails 1431, such that first actuator component 1419 is moveable between the first and second positions along guiderails 1431. One or more guiderails 1431 are coupled at one end to second actuator component 1417, and coupled at an opposite end to pusher plate 1440 disposed at the proximal end of handle 1408, wherein pusher plate 1440 is fixedly coupled to a proximal portion of inner catheter 1411. Accordingly, movement of second actuator component 1417 from the first position to the second position causes pusher plate to move distally within the housing of handle 1408 via guiderails 1431, thereby causing inner catheter 1411 to move distally within the distal region of sheath 1410.

First actuator component 1419 includes a lumen sized and shaped to receive centering element 1429, wherein centering element 1429 is fixed relative to handle 1408. First actuator 1422 is further coupled to proximal portion 1427 sized and shaped to move within a lumen of centering element 1429. Proximal portion 1427 includes a lumen sized and shaped to receive inner catheter 1411, such that proximal portion 1427 is moveable between the first and second positions along inner catheter 1411. First actuator 1422 may be moveably coupled to inner catheter 1411 via proximal portion 1427, and may include port 1439 for coupling to a fluid source to introduce fluid into the guidewire lumen of inner catheter 1411 for flushing. In addition, first actuator component 1419 is coupled to sheath 1410 for extending and retracting the distal end of sheath 1410 as described in further detail below.

Figure 16C:
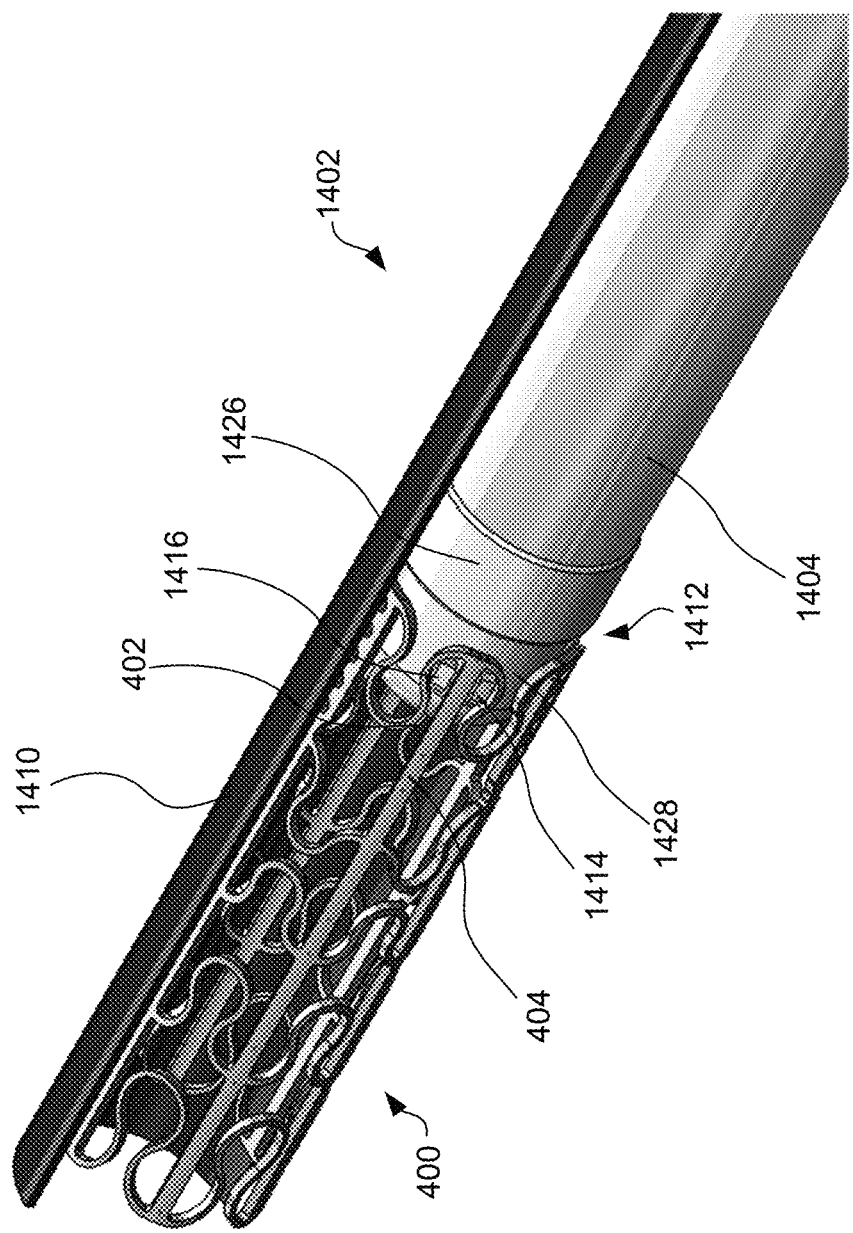

FIG. 16C illustrates distal end 1402 having device 400 coupled thereto in a collapsed state and catheter 1404 disposed within the distal portion of sheath 1410 (shown in cross-section for clarity), e.g., in a position suitable for percutaneous delivery to the left atrium of the patient. Distal end 1402 includes hub 1412 disposed distal to the distal end of catheter 1404. Hub 1412 may have engagement portion 1428 disposed distal to ring portion 1426, and a proximal portion that is moveably disposed within a cavity of catheter 1404 as described in further detail below. Ring portion 1426 has a diameter that is equal to or slightly less than the diameter of the inner wall of sheath 1410 such that hub 1412 may move backwards and forwards within sheath 1410. Engagement portion 1428 of hub 1412 has a diameter less than that of ring portion 1426, such that device 400 may fit between the outer surface of engagement portion 1428 and sheath 1410 when device 400 is in a collapsed, delivery state. Engagement portion 1428 may have a cylindrical shape and a curved distal end as shown. Hub 1412 is moveable relative to catheter 1404 within sheath 1410 along an inner catheter disposed within a lumen extending through hub 1412 and catheter 1404 as described in further detail below. Hub 1412 is releasably coupled to the distal end of catheter 1404 via a locking mechanism operatively coupled to third actuator 1424, such that actuation of third actuator 1424 from the first position to the second position causes the locking mechanism to unlock, thereby decoupling hub 1412 from catheter 1404.

In addition, hub 1412 includes one or more engagers, e.g., protrusions 1414, 1416 and 1418, extending radially outward from a central axis of catheter 1404, such that the one or more engagers are disposed circumferentially about the outer surface of hub 1412, e.g., at engagement portion 1428, and are configured to fit securely between struts and rings of the interatrial devices for delivery. Thus, each of the one or more engagers may be sized to engage device 400 in openings between rings 402 and struts 404 when device 400 is in a contracted, delivery state. For example, the distance from the central axis of hub 1412 to the outermost surface of each of the one or more engagers is equal to or slightly less than the inner radius of sheath 1410 so that hub 1412 may be moveable within sheath 1410. The distance from the central axis of hub 1412 to the outermost surface of each of the one or more engagers may be equal to the distance from the central axis of hub 1412 to the outer surface of ring portion 1426. Accordingly, device 400 may be constrained between the one or more engagers and ring portion 1426, and between engagement portion 1428 and sheath 1410 in order to prevent dislodgement or early deployment of device 400 within sheath 1410. As shown in FIG. 16C, protrusions 1414 and 1416 engage device 400 in openings between rings 402 and struts 404 such that device 400 is constrained between hub 1412 and the inner wall of sheath 1410 in a contracted, delivery state. As will be readily understood by one of ordinary skill in the art, while two engagers are illustrated, more or fewer engagers may be used without departing from the scope of the present invention. For example, one, three, four, five, six, seven, eight, or more engagers may be used.

FIG. 16D is a partial cross-sectional schematic of the delivery apparatus within the sheath during step 1506, wherein the delivery apparatus is coupled to device 400, and FIG. 16E illustrates the delivery apparatus of FIG. 16D with device 400 omitted for clarity. As shown in FIG. 16D, the distal end of sheath 1410, with the delivery apparatus disposed therein, is advanced across the atrial septum AS. Protrusions 1414 and 1416 fit securely between struts and rings of device 400 such that device 400 is constrained between protrusions 1414 and 1416 and ring portion 1426, and between engagement portion 1428 and sheath 1410. As shown in FIG. 16E, hub 1412 is adjacent to catheter 1404 such that proximal portion 1432 of hub 1412 is disposed within cavity 1436 of catheter 1404. Cavity 1436 is sized and shaped to receive proximal portion 1432 of hub 1412 a predetermined distance. Cavity 1436 has a larger outer diameter than the outer diameter for the lumen in catheter 1404 that receives inner catheter 1411. Proximal portion 1432 is coupled to ring portion 1426 via connector 1434. Hub 1412 may be releasably coupled to catheter 1404 via a locking mechanism for engaging catheter 1404 to at least one of ring portion 1426 or proximal portion 1432.

In addition, inner catheter 1411 is disposed within a central lumen extending through hub 1412 and catheter 1404. Inner catheter 1411 may include a stop, e.g., lock ring 1438, fixed at a distal end of inner catheter 1411, wherein lock ring 1438 is sized and shaped to be disposed within cavity 1430 of hub 1412. Cavity 1430 may extend through at least a portion of engagement portion 1428 of hub 1412, or completely through engagement portion 1428 of hub 1412 and at least a portion of ring portion 1426 of hub 1412. Lock ring 1438 ensures that hub 1412 does not extend beyond a predetermined distance distally along inner catheter 1411, and that inner catheter 1411 does not retract beyond the predetermined distance proximally relative to hub 1412. Inner catheter 1411 also may include guidewire lumen 1425 sized and shaped to receive a guidewire therethrough. For example, delivery apparatus 1400 may be advanced over a guidewire such that the distal end of sheath 1410 having distal end 1402 coupled to device 400 disposed therein, is positioned across the fossa ovalis.

Figure 16F:
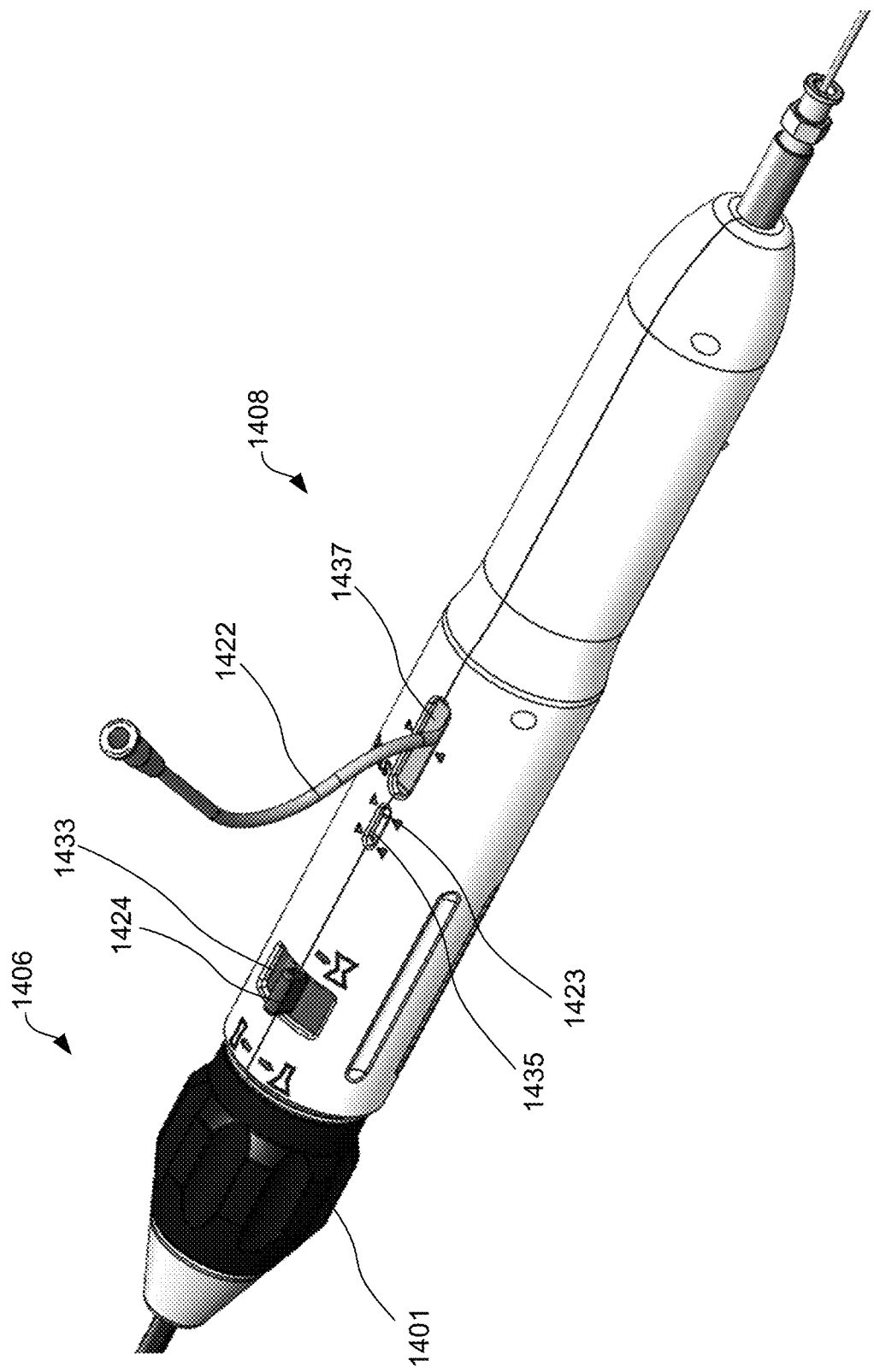
Figure 16G:
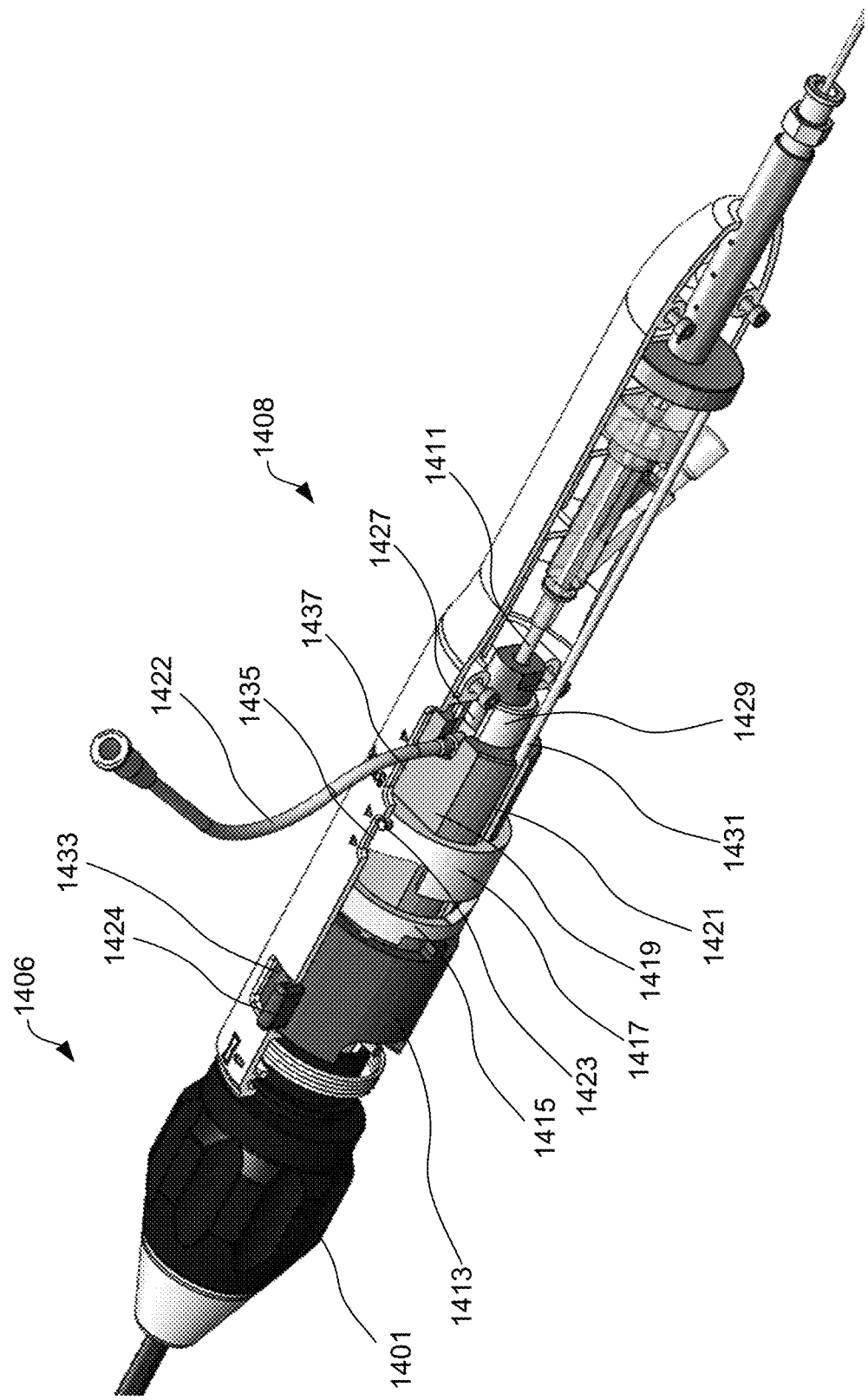
Figure 16H:
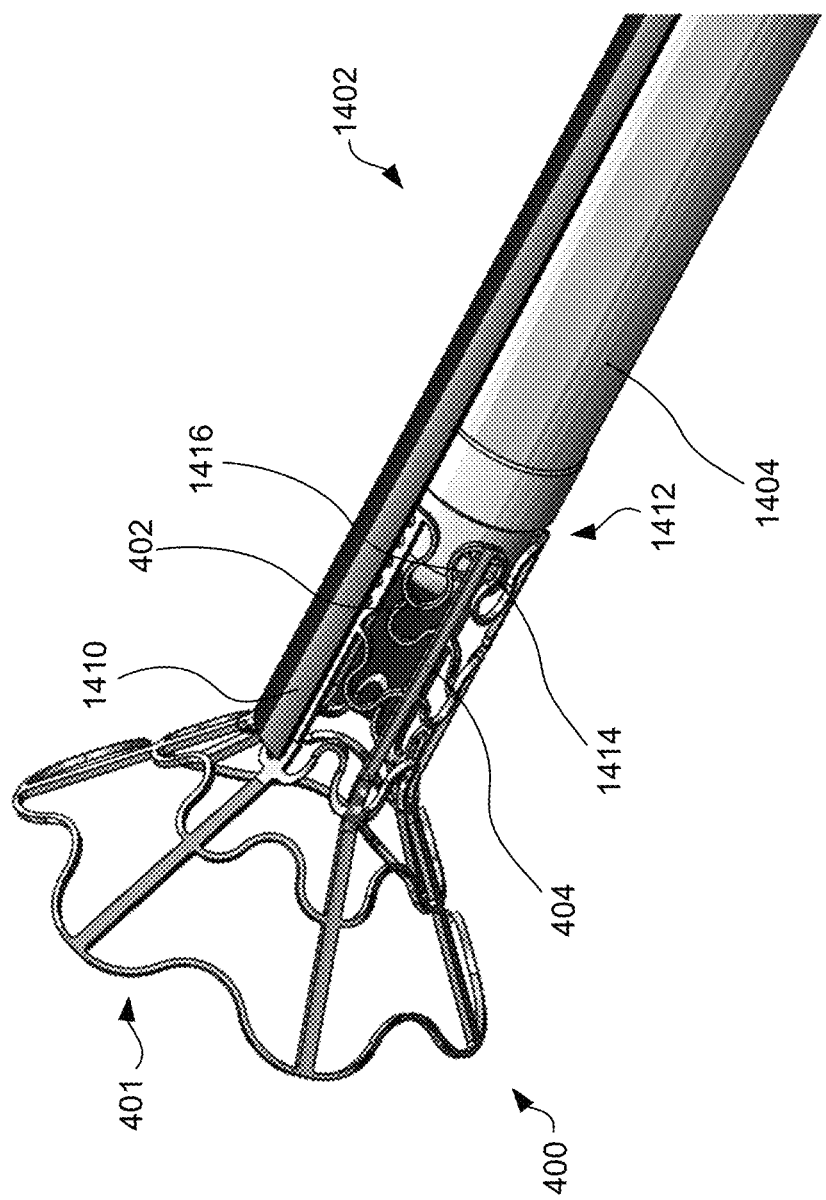

Referring now to FIGS. 16F and 16G, first actuator 1422 is then moved from a first initial position to a second position within opening 1437 of the housing of handle 1408, which causes distal end 1402 including inner catheter 1411 and hub 1412 having device 400 coupled thereto, and catheter 1404 to move relative to sheath 1410. As illustrated in FIG. 16G, movement of first actuator 1422 causes first actuator component 1419 to move from the first initial position to the second position through the lumens of second actuator component 1417, actuator ring 1415, and third actuator component 1413 along guiderail 1431, and proximal portion 1427 to move from the first initial position to the second position along inner catheter 1411 within centering element 1429. Specifically, movement of first actuator 1424 from the first initial position to the second position causes first actuator component 1419 operatively coupled to sheath 1410 to move sheath 1410 relative to catheter 1404, hub 1412, and inner catheter 1411, thereby exposing first flared end region 401 of device 400 beyond the distal end of sheath 1410 such that first flared end region 401 expands to its deployed state in the left atrium as shown in FIG. 16H (step 1507). According to one aspect of the invention, actuation of first actuator 1422 may cause catheter 1404, hub 1412, and inner catheter 1411 to be advanced distally while sheath 1410 remains stationary with respect to atrial septum AS.

FIG. 16I is a cross-sectional schematic of the delivery apparatus within the sheath during step 1507, wherein device 400 is partially deployed, and FIG. 16J illustrates the delivery apparatus of FIG. 16I with device 400 omitted for clarity. As shown in FIG. 16I, first flared end region 401 of device 400 is deployed in the left atrium of the patient a predetermined distance from the atrial septum AS. Referring to FIG. 16J, the delivery apparatus, e.g., hub 1412 and catheter 1404 moves distally within sheath 1410 relative to sheath 1410, such that first flared end region 401 extends beyond the distal end of sheath 1410 and transitions from a collapsed, delivery state to an expanded, deployed state within the left atrium, while the second flared end of device 400 remains in a collapsed, delivery state within the distal end of sheath 1410.

Figure 16K:
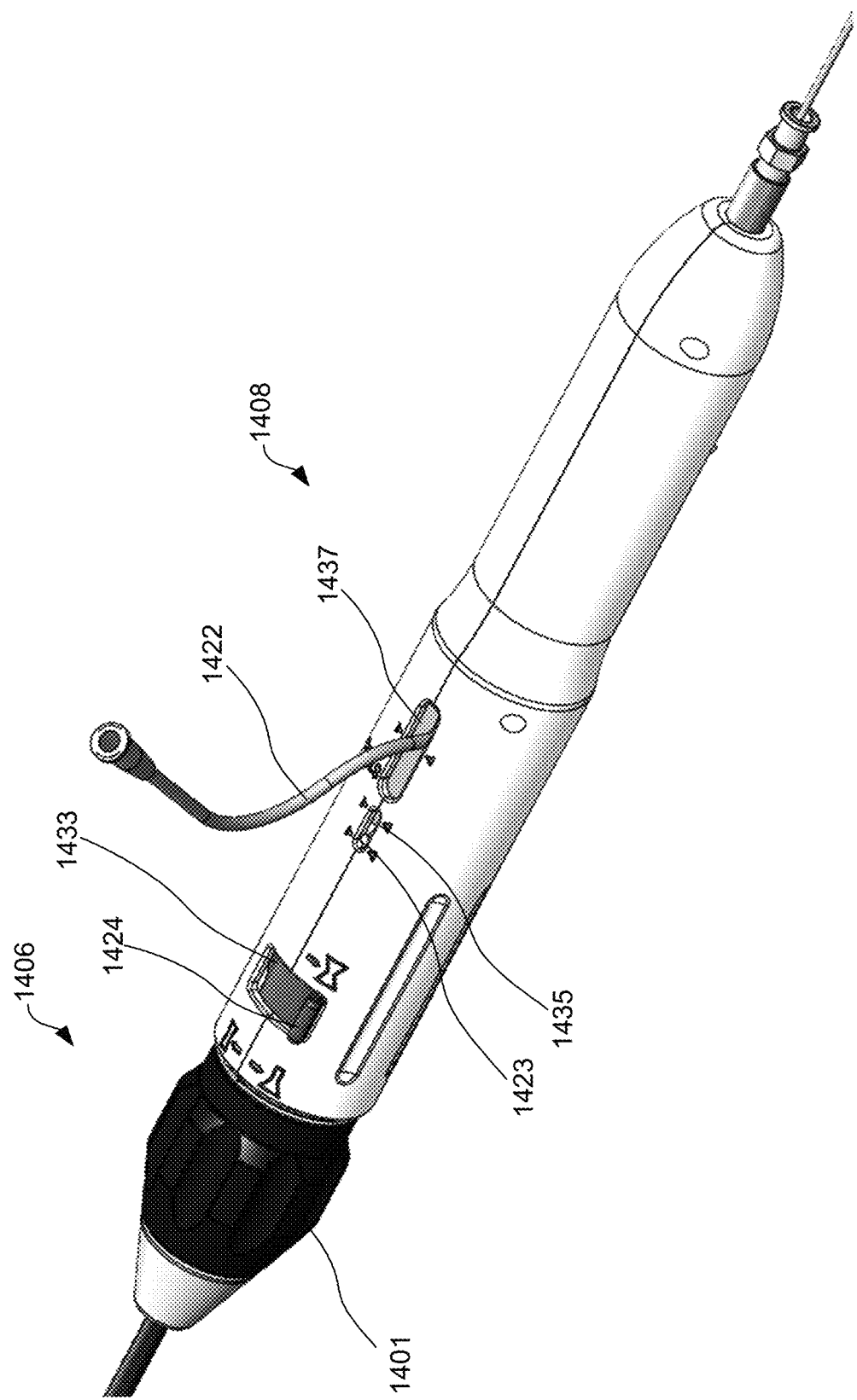
Figure 16L:
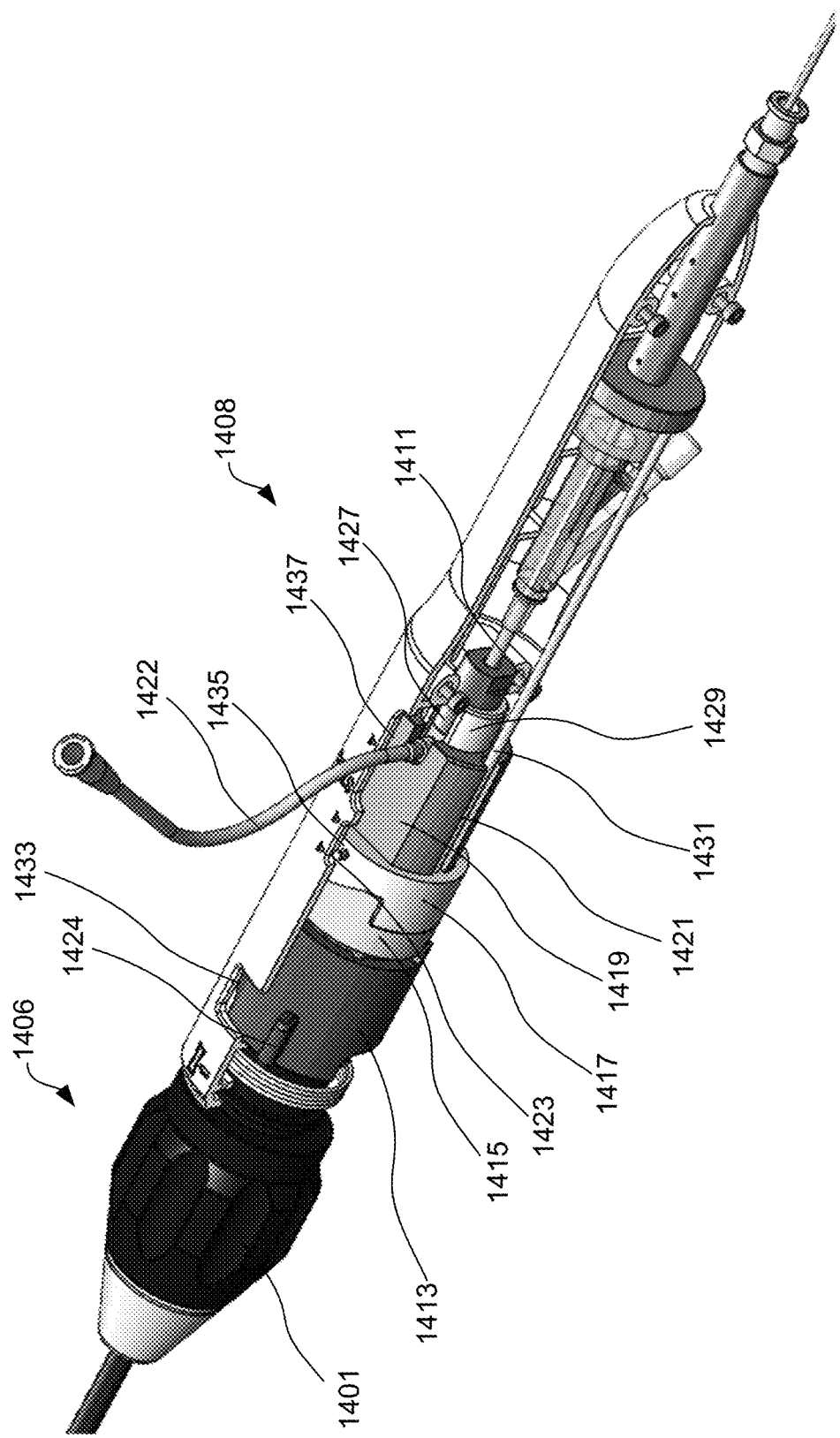
Figure 16M:
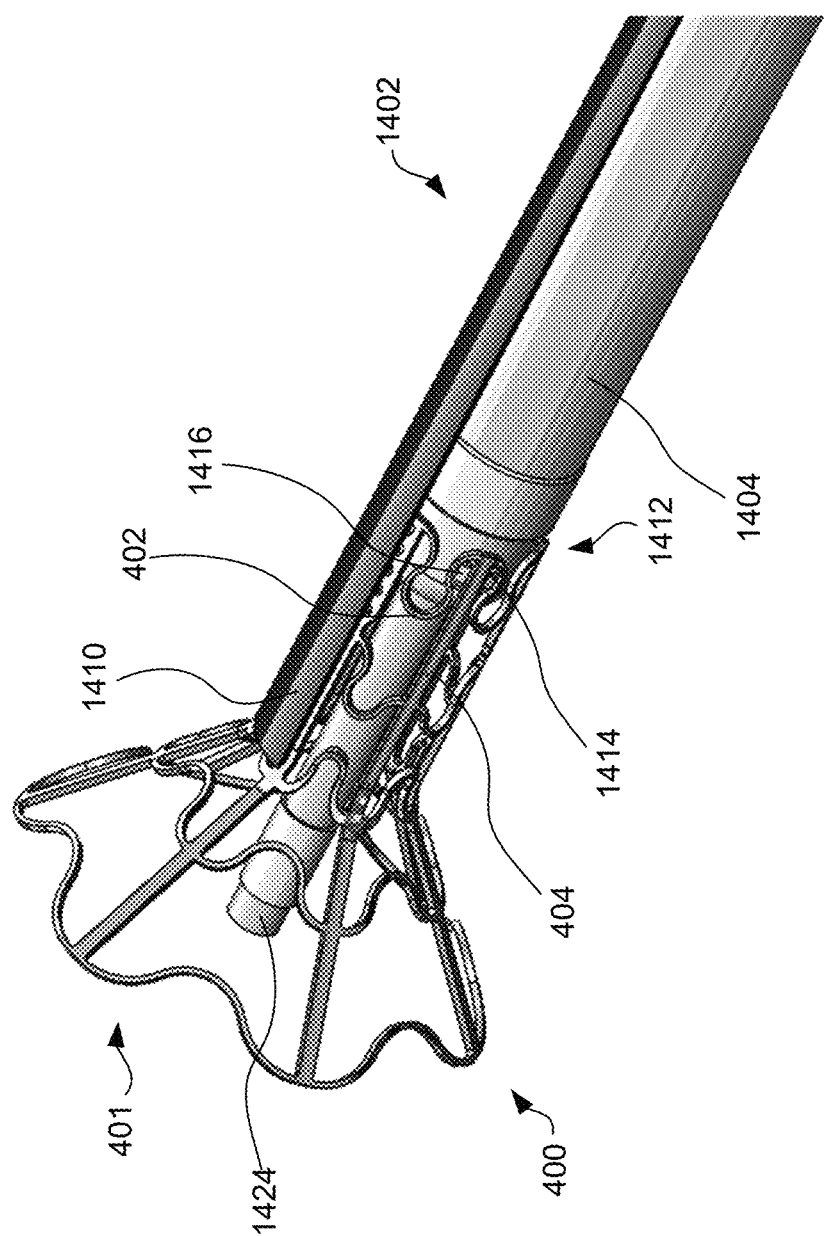

Referring now to FIGS. 16K and 16L, second actuator 1423 may then be moved from the first initial position to the second position which causes second actuator component 1417 to move distally along first actuator component 1419 within the housing of handle 1408. As second actuator component 1417 moves distally along first actuator component 1419, the distal edge of second actuator component 1417 interacts with the groove of actuator ring 1415, thereby causing actuator ring 1415 to rotate until the indent of actuator ring 1415 engages with the edge of the tooth of third actuator component 1413. In addition, movement of second actuator component 1417 from the first initial position to the second position causes inner catheter 1411 to move distally relative to hub 1412, catheter 1404, and sheath 1410 via guiderails 1431 and pusher plate 1440 as illustrated in FIG. 16M. Accordingly, the delivery apparatus, e.g., sheath 1410, inner catheter 1411, catheter 1404, and hub 1412 coupled to device 400, may be pulled proximally until first flared end region 401 engages the atrial septum from within the left atrium (step 1508).

FIG. 16N is a cross-sectional schematic of the delivery apparatus within the sheath during step 1508, wherein inner catheter 1411 has been moved distally relative to sheath 1410, hub 1412, and catheter 1404 such that lock ring 1438 is no longer disposed within cavity 1430 of engagement portion 1428 of hub 1412, and the delivery apparatus is pulled proximally until first flared end region 401 engages the left side of atrial septum AS. FIG. 16O illustrates the delivery apparatus of FIG. 16N with device 400 omitted for clarity. Specifically, FIG. 16O illustrates sheath 1410, hub 1412, inner catheter 1411, and catheter 1404 pulled proximally with respect to atrial septum AS. Using fluoroscopic or echocardiographic visualization, the clinician next verifies that the device is positioned across the fossa ovalis. The clinician then reduces the pulling force of sheath 1410, catheter 1404, and hub 1412, and allows the fossa ovalis to straighten. In accordance with one aspect of the present invention, the physician may reduce and/or stop the pulling force of the delivery apparatus upon force feedback provided by the atrial septum against the delivery apparatus, which indicates that device 400 is properly positioned within the opening of the atrial septum. This may prevent accidentally deploying the entire device in the left atrium and may assist in positioning the device when advanced at non-perpendicular angles.

Referring back to FIG. 16L, third actuator 1424 may then be moved from the first initial position to the second position, which causes third actuator component 1413 to rotate about first actuator component 1419. The engagement between the tooth of third actuator component 1413 and the indent of actuator ring 1415 allows rotation of third actuator component 1413 to rotate actuator ring 1415 in the same direction, e.g., counter-clockwise, until the groove of actuator ring 1415 engages with the indent of second actuator component 1417. This causes the locking mechanism to decouple hub 1412 and catheter 1404 to permit full deployment of device 400.

If for any reason device 400 is not in the proper position for deployment within the atrial septum, sheath 1410 may be advanced over device 400 while catheter 1404 is stationary, thereby collapsing first flared end region 401 within sheath 1410. Specifically, knob 1401 of handle 1408 may be rotated to cause sheath 1410 to move translationally relative to catheter 1404 and device 400, to thereby collapse device 400 within sheath 1410. For example, sheath 1410 may be moved over collapsed device 400 until device 400 is completely collapsed within sheath 1410. Distal end 1402, with device 400 disposed therein, may then be retrieved. Alternatively, distal end 1402 may be repositioned relative to the fossa ovalis of the atrial septum prior to partially advancing first flared end region 401 out of sheath 1410 within the left atrium.

Figure 16P:
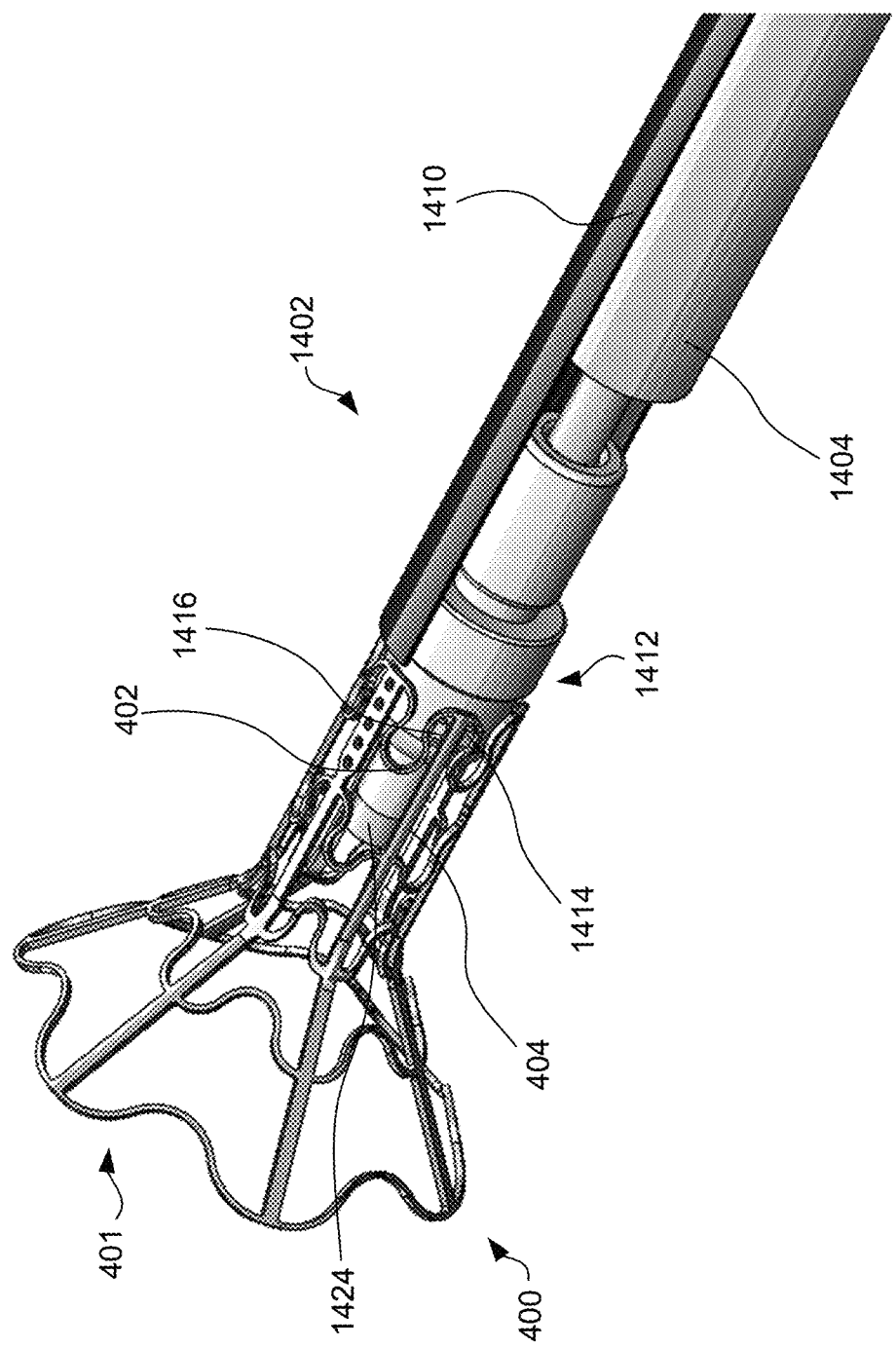

When third actuator 1424 is in the second position and hub 1412 and catheter 1404 are decoupled, the delivery apparatus may be pulled proximally by the physician such that the atrial septum maintains device 400 in position against the left side of the atrial septum until second flared end region 403 of device 400 is no longer constrained between hub 1412 and sheath 1410 as shown in FIG. 16P. As sheath 1410, catheter 1404, and inner catheter 1411 are retracted proximally, hub 1412 remains stationary with respect to the atrial septum as the one or more engagers of hub 1412 are engaged with the struts of second flared end region 403 of device 400 within sheath 1410. Hub 1412 is permitted to move distally along inner catheter 1411 until cavity 1430 of hub 1412 prevents lock ring 1438 of inner catheter 1411 from further proximal movement. When second flared end region 403 of device 400 is exposed beyond the distal end of sheath 1410, second flared end region 403 then transitions from a collapsed, delivery state to an expanded, deployed state within the right atrium, and neck region 405 is lodged in the puncture of the atrial septum (step 1509).

Figure 16S:
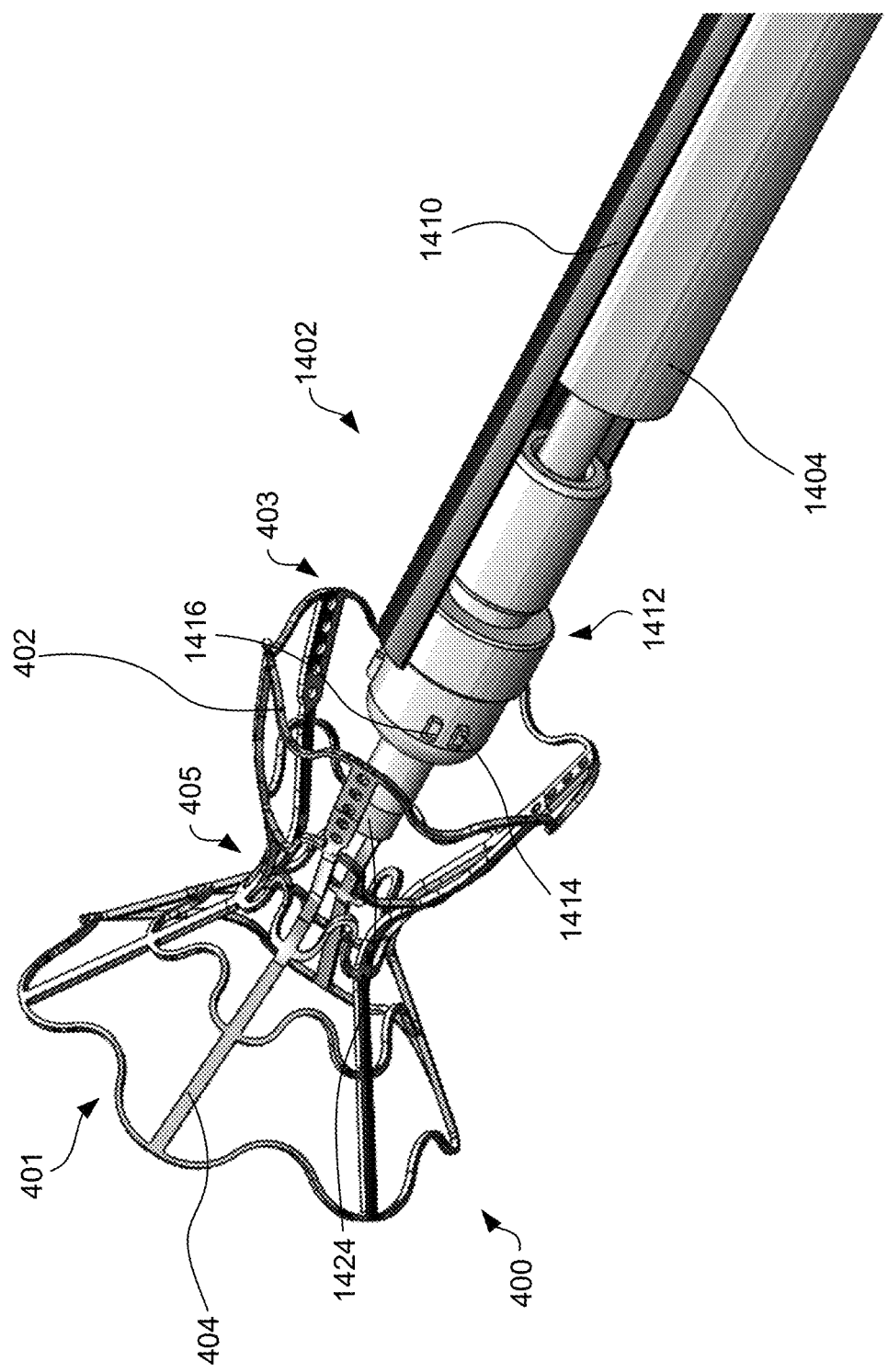

FIG. 16Q is a cross-sectional schematic of the delivery apparatus within the sheath during step 1509, wherein the delivery apparatus is pulled proximally such that second flared end region 403 of device 400 is no longer constrained between hub 1412 and sheath 1410. FIG. 16R illustrates the delivery apparatus of FIG. 16Q with device 400 omitted for clarity. As shown in FIG. 16Q, sheath 1410 is no longer disposed over protrusions 1414 and 1416 such that second flared end region 403 is no longer constrained in the collapsed, delivery state, thereby causing first flared end region 401 to engage the left side of the atrial septum and neck region 405 of the device to lodge in the puncture through the fossa ovalis, and allowing expansion of second flared end region 403 of the device into the right atrium as shown in FIG. 16S.

Referring back to FIG. 16R, inner catheter 1411, catheter 1404, and sheath 1410 are pulled proximally while hub 1412 of the delivery apparatus, e.g., engagement portion 1428, ring portion 1426, and proximal portion 1432, remains stationary with respect to atrial septum AS until at least a portion of proximal portion 1432 of hub 1412 is no longer disposed within cavity 1436 of catheter 1404. In addition, at least a partial portion of ring lock 1438 of inner catheter 1411 may be disposed within cavity 1430 of engagement portion 1428 of the hub. As described above, ring lock 1438 and cavity 1430 prevent inner catheter 1411 from being pulled proximally relative to the hub beyond a predetermined distance.

Figure 16T:
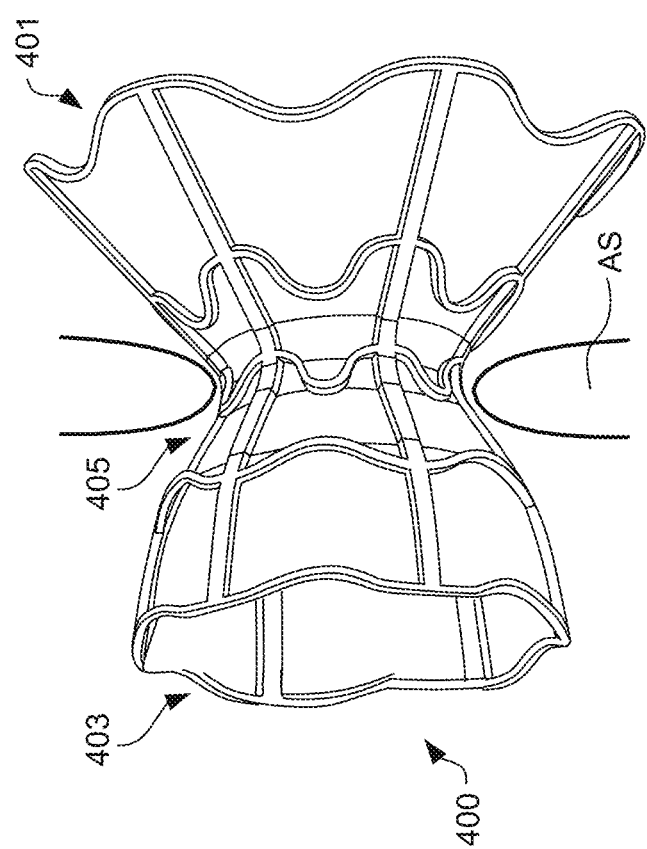

Any remaining components of the delivery system then may be removed, e.g., sheath, distal end of delivery apparatus, the catheter, and the guidewire (step 1510). Once positioned in the fossa ovalis as shown in FIG. 16T, device 400 shunts blood from the left atrium to the right atrium when the left atrial pressure exceeds the right atrial pressure (step 1511), thus facilitating treatment and/or the amelioration of symptoms associated with CIF.

It should be noted that the inventive devices also may be used with patients having disorders other than heart failure. For example, in one embodiment the device may be implanted in a subject suffering from myocardial infarction, for example in the period immediately following myocardial infarction (e.g., within a few days of the event, or within two weeks of the event, or even within six months of the event). During such a period, the heart remodels to compensate for reduced myocardial function. For some subjects suffering from severe myocardial infarction, such remodeling may cause the function of the left ventricle to significantly deteriorate, which may lead to development of heart failure. Implanting an inventive device during the period immediately following myocardial infarction may inhibit such deterioration in the left ventricle by reducing LAP and LVEDP during the remodeling period. The device optionally then may be removed as described in further detail below.

Exemplary method 1700 of retrieving device 400 from a subject, for example, from a puncture through the fossa ovalis, will now be described with reference to FIG. 17. The steps of method 1700 may be further elaborated by referring to FIGS. 18A-18F.

Figure 17:
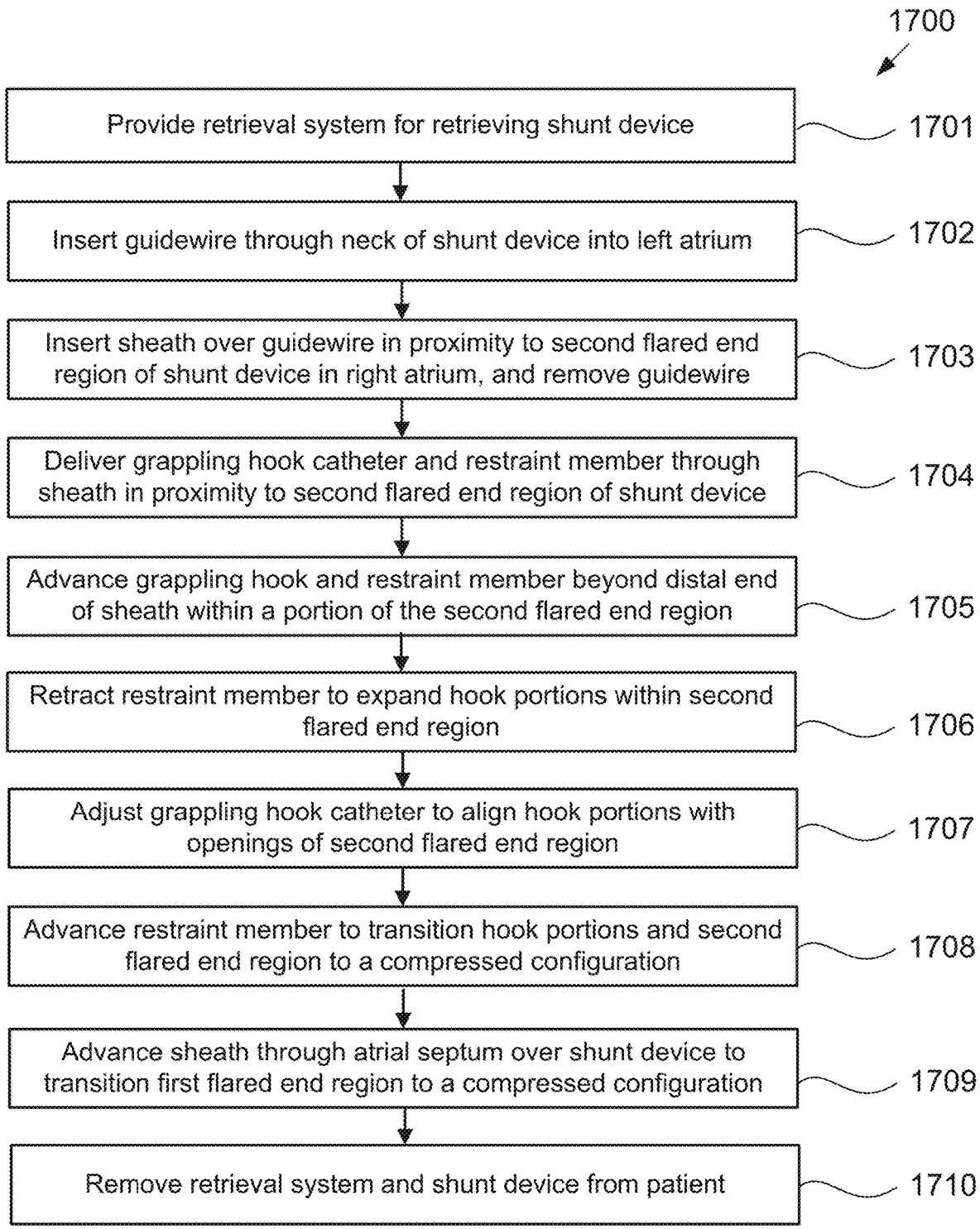
FIG. 17 is a flow chart of steps in an exemplary method of retrieving an hourglass-shaped device implanted in a puncture through the fossa ovalis in accordance with the present invention.

FIG. 17 is a flow chart of steps in an exemplary method of retrieving an hourglass-shaped device implanted in a puncture through the fossa ovalis in accordance with the present invention. At step 1701, a retrieval system for retrieving an implanted shunt device, e.g., hourglass-shaped device 400 of FIG. 4, is provided. For example, the retrieval system includes a retrieval catheter, e.g., grappling hook, having one or more hook portions at the distal end thereof which preferably are formed of a shape memory metal and are biased toward a position radially outward from a central axis of the retrieval catheter, a restraint member coupled to a control tube and positioned over at least a portion of the retrieval catheter, and a sheath having a lumen sized and shaped to receive the retrieval catheter and the restraint member. The hook portions are sized and shaped to align with the openings between the struts and rings of the shunt device. Accordingly, the number of hook portions may correspond with the number of openings between the struts and rings of the shunt device.

At step 1702, a guidewire is inserted through the neck of the implanted shunt device through the fossa ovalis of the atrial septum into the left atrium. The guidewire may be inserted using techniques readily known in the art. At step 1703, the sheath is inserted over the guidewire and positioned in proximity to the flared end region of the shunt device disposed in right atrium. The guidewire may then be removed. At step 1704, the retrieval catheter and the restraint member are delivered through the sheath in proximity to the flared end region of the shunt device disposed in right atrium. FIG. 18A is a partial cross-sectional schematic of retrieval system 1800 during step 1704. As illustrated in FIG. 18A, sheath 1802 having retrieval catheter 1804 and restraint member 1808 disposed therein is positioned in proximity to second flared end region 403 of device 400 within the right atrium. Restraint member 1808 is positioned over a portion of retrieval catheter 1804 such that hook portions 1806 are maintained in a compressed configuration within sheath 1802. Although only two hook portions 1806 are illustrated in FIG. 18A, as will be understood by a person ordinarily skilled in the art, retrieval catheter 1804 may include less or more than two hook portions, e.g., one, three, four, five, or six hook portions. Restraint member 1808 may be moved proximally and distally over retrieval catheter 1804 within sheath 1802 via control tube 1810. Alternatively, a control wire having sufficient stiffness may be used to move restraint member 1808 within sheath 1802.

Figure 18C:
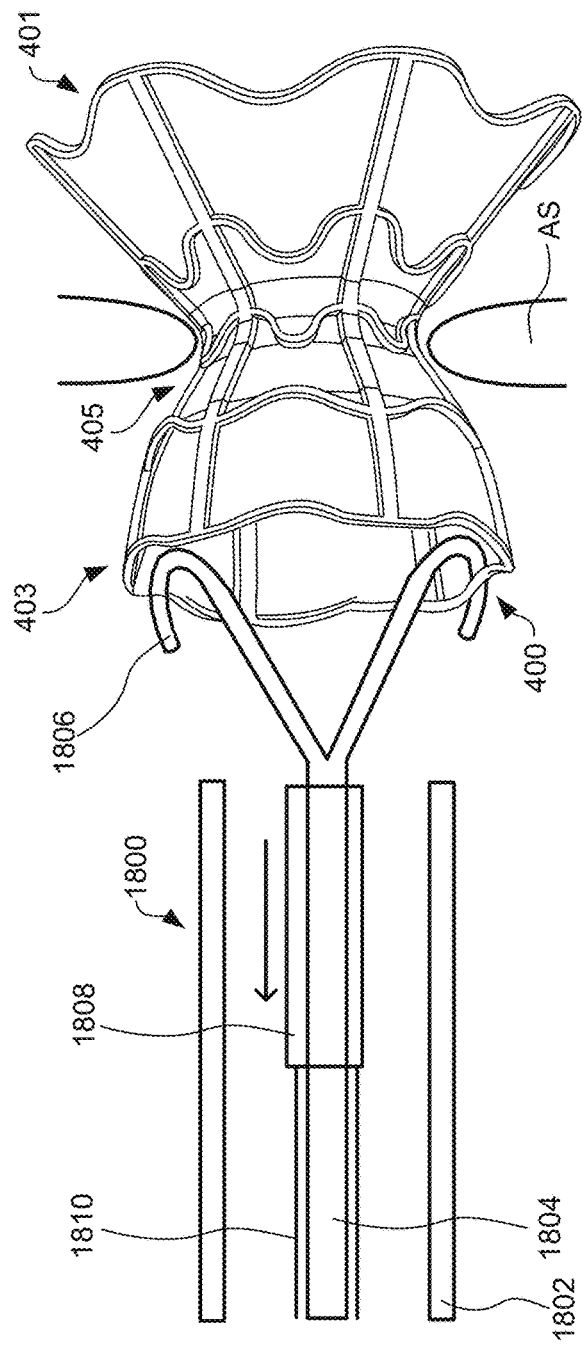

At step 1705, retrieval catheter 1804 along with restraint member 1808 are advanced distally and exposed beyond the distal end of sheath 1802 within the right atrium such that hook portions 1806 are within at least a portion of second flared end region 403 of device 400, as illustrated in FIG. 18B. At step 1706, restraint member 1808 is retracted proximally along retrieval catheter 1804 within sheath 1802 via control tube 1810. Accordingly, hook portions 1806 expand radially outward from the central axis of retrieval catheter 1804 as they are no longer restrained by restraint member 1808, as illustrated in FIG. 18C. At step 1707, retrieval catheter 1804 may be adjusted to align hook portions 1806 with the openings between the struts and rings of second flared end region 403 of device 400.

Figure 18D:
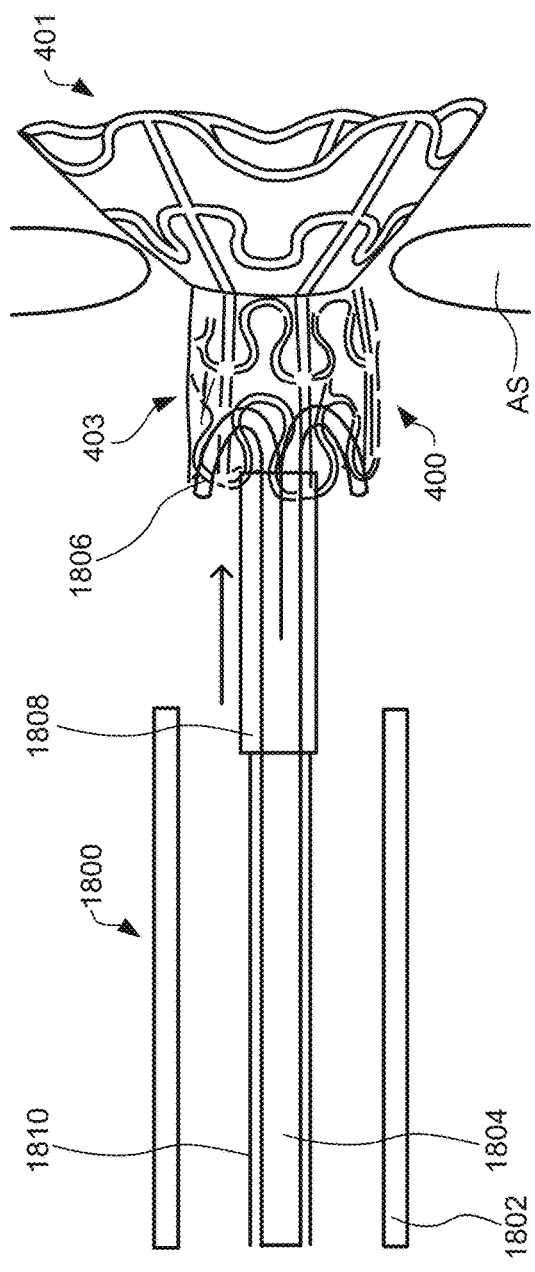

At step 1708, while hook portions 1806 are maintained in placed and engaged with second flared end region 403 of device 400, restraint member 1808 is advanced distally toward hook portions 1806 via control tube 1810, thereby causing hook portions 1806, and accordingly second flared end region 403, to transition to a compressed configuration, as illustrated in FIG. 18D. Next, at step 1709, sheath 1802 is advanced distally over retrieval catheter 1804 and device 400, through the atrial septum AS and into the left atrium, thereby causing first flared end region 401 of device 400 to transition to a compressed configuration within sheath 1802, as illustrated in FIG. 18E. Finally, at step 1710, system 1800 is pulled proximally to remove retrieval system 1800 and device 400 from the patient, as illustrated in FIG. 18F.

In accordance with another aspect of the present invention, exemplary method 1900 of retrieving device 400 from a subject, for example, from a puncture through the fossa ovalis, will now be described with reference to FIG. 19. The steps of method 1900 may be further elaborated by referring to FIGS. 20A-20G.

Figure 19:
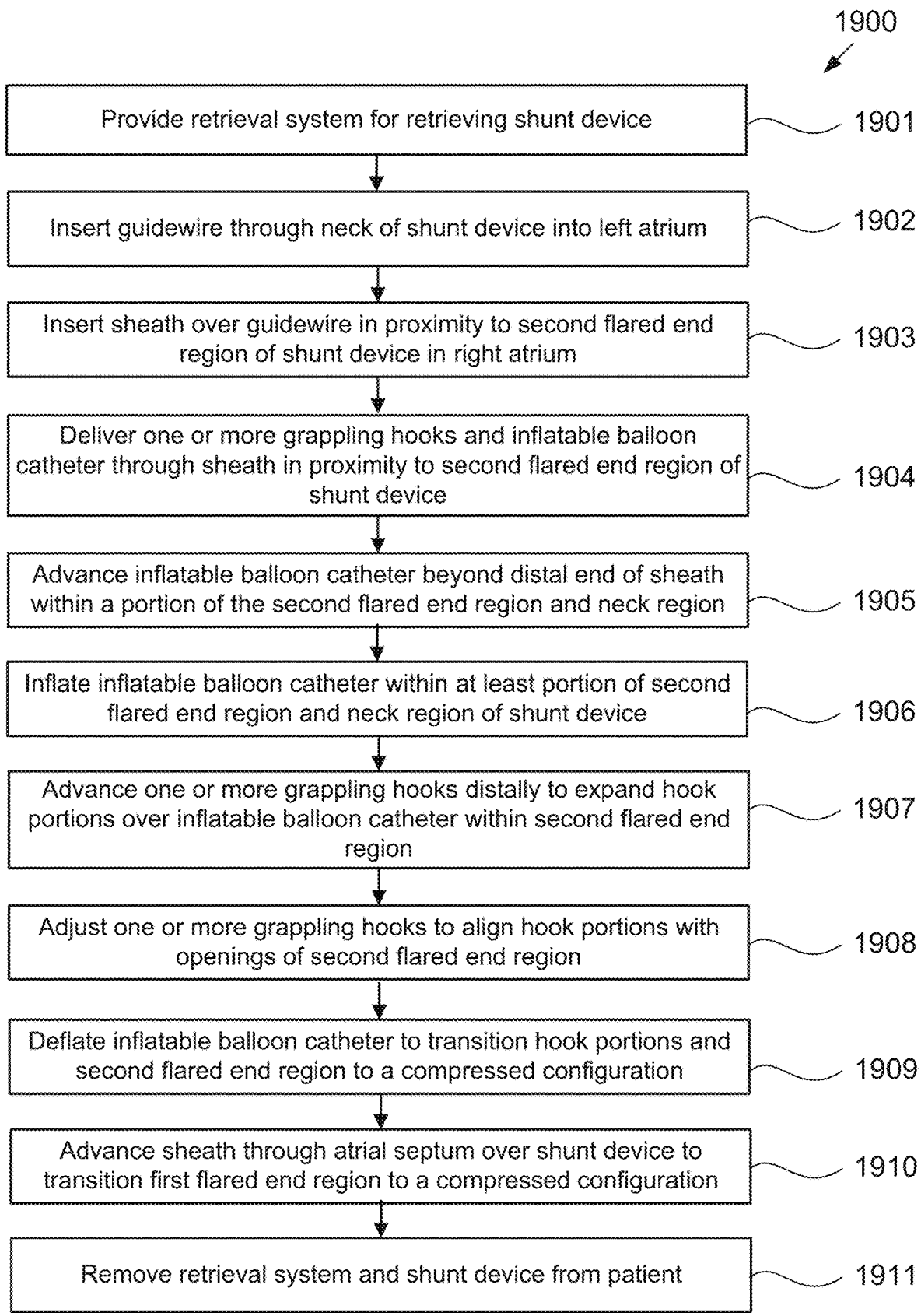
FIG. 19 is a flow chart of steps in an alternative exemplary method of retrieving an hourglass-shaped device implanted in a puncture through the fossa ovalis in accordance with the present invention.
Figure 20G:
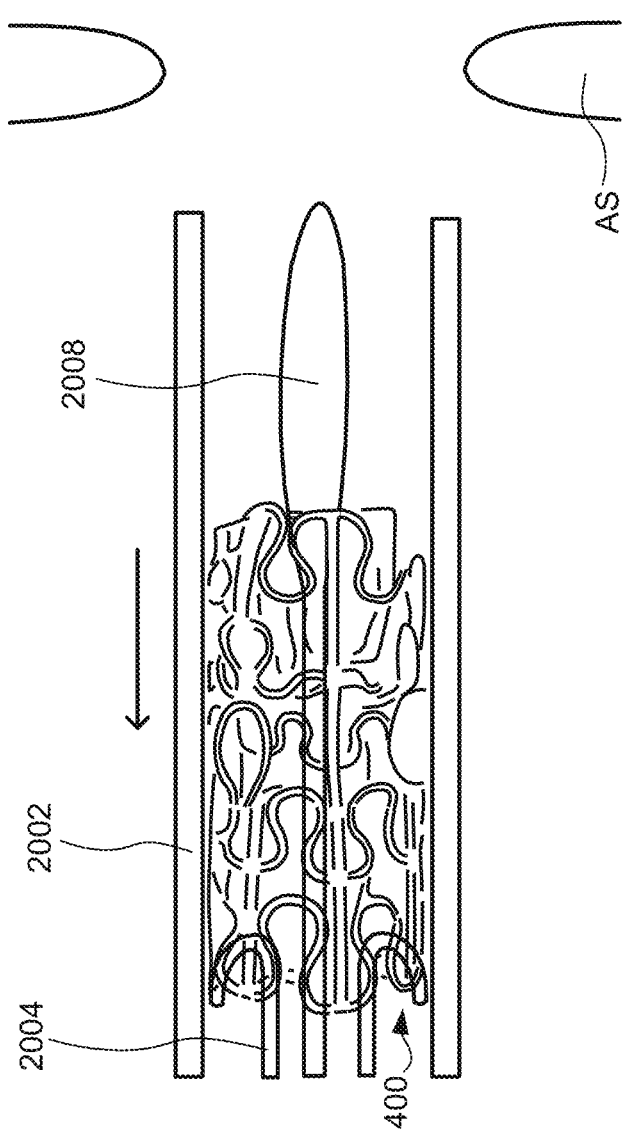

FIG. 19 is a flow chart of steps in an exemplary method of retrieving an hourglass-shaped device implanted in a puncture through the fossa ovalis in accordance with the present invention. At step 1901, a retrieval system for retrieving an implanted shunt device, e.g., hourglass-shaped device 400 of FIG. 4, is provided. For example, the retrieval system includes grappling hook having one or more hook portions at the distal region thereof which preferably are formed of a shape memory metal and are biased radially inward toward a central axis of the retrieval system, an inflatable balloon catheter, and a sheath having a lumen sized and shaped to receive the grappling hook and the inflatable balloon catheter. The one or more curved hooked portions of the grappling hook are sized and shaped to align with the openings between the struts and rings of the shunt device in an expanded state. Accordingly, the number of hook portions may correspond with the number of openings between the struts and rings of the shunt device. As will be understood by a person ordinarily skilled in the art, the inflatable balloon catheter may be delivered within a separate balloon channel moveable within the sheath.

At step 1902, a guidewire is inserted through the neck of the implanted shunt device through the fossa ovalis of the atrial septum into the left atrium. The guidewire may be inserted using techniques readily known in the art. At step 1903, the sheath is inserted over the guidewire and positioned in proximity to the flared end region of the shunt device disposed in right atrium. At step 1904, the grappling hook and the inflatable balloon catheter are delivered through the sheath over the guidewire in proximity to the flared end region of the shunt device disposed in right atrium. FIG. 20A is a partial cross-sectional schematic of retrieval system 2000 during step 1904. As illustrated in FIG. 20A, sheath 2002 having grappling hook 2004 and inflatable balloon catheter 2008 in a deflated state disposed therein is positioned in proximity to second flared end region 403 of device 400 within the right atrium. Although only two hook portions 2006 are illustrated in FIG. 20A, as will be understood by a person ordinarily skilled in the art, grappling hook 2004 may include less or more than two hook portions 2006, e.g., one, three, four, five, or six hook portions. Hook portions 2006 of grappling hook 2004 may be joined together at a proximal region of grappling hook 2004, e.g., via a ring having a lumen sized and shaped to receive inflatable balloon catheter 2008 such that grappling hook 2004 may move proximally or distally over inflatable balloon catheter 2008 within sheath 2002.

At step 1905, inflatable balloon catheter 2008 is advanced distally, e.g., over the guidewire (not shown), and exposed beyond the distal end of sheath 2002 within the right atrium in a deflated condition such that inflatable balloon catheter 2008 is positioned within at least a portion of second flared end region 403 of device 400, as illustrated in FIG. 20B. At step 1906, inflatable balloon catheter 2008 is inflated to an inflated state within at least a portion of second flared end region 403 and neck region 405 of device 400, as illustrated in FIG. 20C. For example, inflatable balloon catheter 2008 may be coupled to a source of fluid at its proximal end outside the patient's body for inflation of inflatable balloon catheter 2008, and may expand to have a diameter equal to the diameter of neck region 405 of device 400. Inflation of inflatable balloon catheter 2008 aligns retrieval system 2000 with device 400.

At step 1907, grappling hook 2004 is advanced distally and exposed beyond the distal end of sheath 2002 within the right atrium. As illustrated in FIG. 20D, hook portions 2006 of grappling hook 2004 bend radially outwardly in an expanded state as they move across the surface of inflatable balloon catheter 2008 in the inflated state. At step 1908, grappling hook 2004 may be adjusted to align hook portions 2006 with the openings between the struts and rings of second flared end region 403 of device 400.

At step 1909, while hook portions 2006 are maintained in placed and engaged with second flared end region 403 of device 400, inflatable balloon catheter 2008 is deflated and advanced distally into the left atrium. Alternatively, inflatable balloon catheter 2008 may be deflated and removed from the patient's body or deflated and retracted into a balloon channel within sheath 2002. Deflation of inflatable balloon catheter 2008 causes hook portions 2006 of grappling hook 2004, and accordingly second flared end region 403, to transition to a compressed configuration, as illustrated in FIG. 20E.

Next, at step 1910, sheath 2002 is advanced distally over grappling hook 2004, device 400, and inflatable balloon catheter 2008, through the atrial septum AS and into the left atrium, thereby causing first flared end region 401 of device 400 to transition to a compressed configuration within sheath 2002, as illustrated in FIG. 20F. Finally, at step 1911, system 2000 is pulled proximally to remove retrieval system 2000 and device 400 from the patient, as illustrated in FIG. 18G.

Figure 21A:
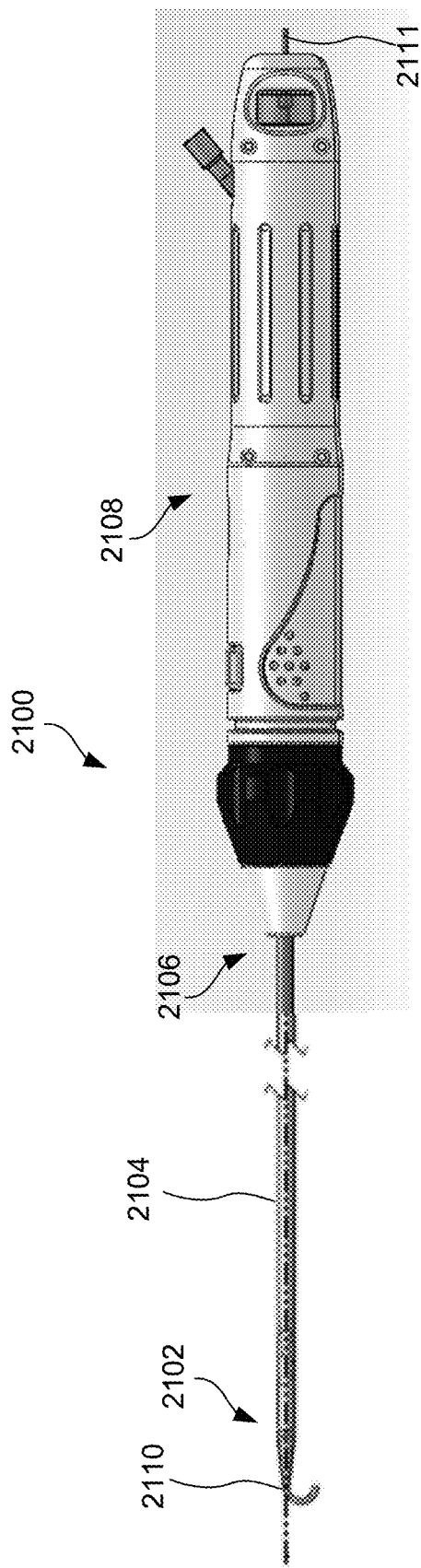
FIG. 21A illustrates yet another alternative exemplary apparatus for delivering devices in accordance with the present invention.
Figure 21B:
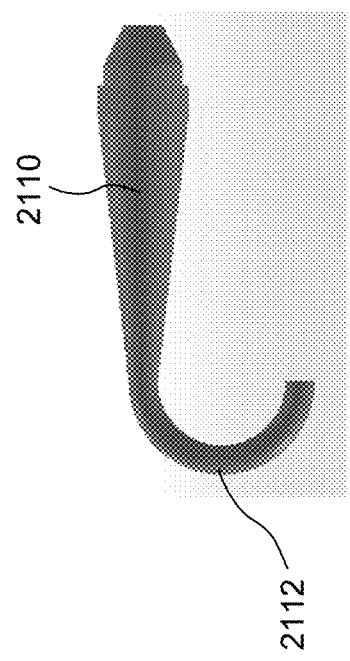
FIG. 21B illustrates the distal end of the apparatus of FIG. 21A.

Referring to FIG. 21A, an alternative exemplary apparatus is provided for delivering interatrial shunt devices, e.g., device 400 of FIG. 4A, 4B or 6Q, and/or devices described in U.S. Pat. No. 9,629,715 to Nitzan, U.S. Pat. No. 9,713,696 to Yacoby, and U.S. Pat. No. 10,076,403 to Eigler. Apparatus 2100 includes distal end 2102, catheter 2104, and proximal end 2106 having handle 2108 for actuating distal end 2102. Distal end 2102 is removeably coupled to distal tip 2110 having flexible pigtail-shaped portion 2112 extending therefrom as illustrated in FIG. 21B. Apparatus 2100 may include an engagement apparatus disposed within catheter 2104 extending from proximal end 2106 to distal end 2102 for delivery and/or retrieval of the interatrial shunt device. The components of apparatus 2100 may include a guidewire lumen sized to receive a guidewire therethrough as described in further detail below.

Figure 22:
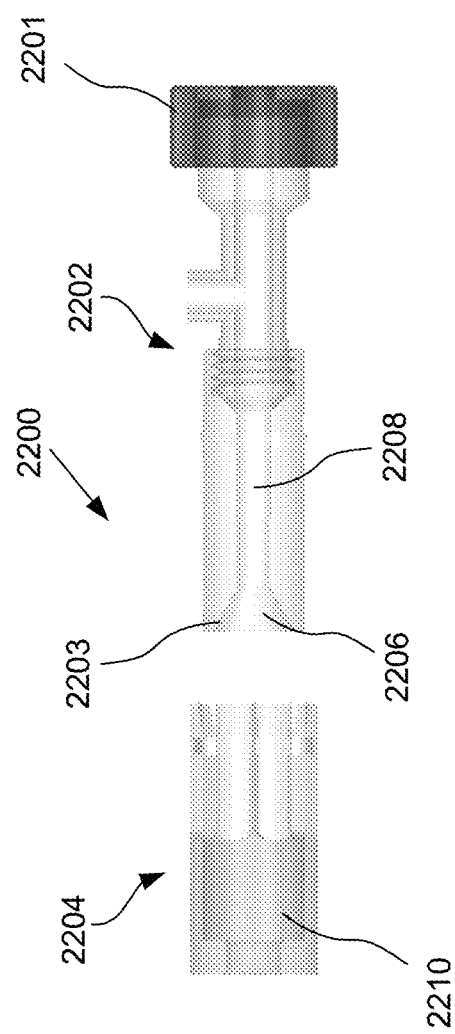
FIG. 22 illustrates a loading tool for loading an exemplary shunt device into the apparatus of FIG. 21A.

Referring now to FIG. 22, an exemplary loading tool is provided for loading an exemplary hourglass-shaped interatrial shunt constructed in accordance with the principles of the present invention into distal end 2102 of apparatus 2100. Loading tool 2200 includes proximal loader 2202 and distal loader 2204. Proximal loader 2202 and distal loader 2204 may be constructed from, e.g., injection molding, and made of a transparent plastic material such that loading of device 400 therein may be visible by the user. Proximal loader 2202 has lumen 2208 extending from proximal end 2201 to distal end 2203 of proximal loader 2202, wherein lumen 2208 is sized and shaped to receive device 400 in a collapsed delivery state as well as distal tip 2110 and catheter 2104 of apparatus 2100. As illustrated in FIG. 22, lumen 2208 has conical shaped cavity 2206 at its distal open end which corresponds to the shape of one of the flared end regions of device 400, e.g., the flared end region configured to be disposed within the left atrium when device 400 is implanted. Further, cavity 2206 is sized such that device 400 must be inserted into proximal loader 2202 in a specific orientation as will be described in further detail below, thereby ensuring proper loading of device 400 into apparatus 2100. In addition, distal loader 2204 has cavity 2210 sized and shaped to receive distal end 2203 of proximal loader 2202.

Figure 23:
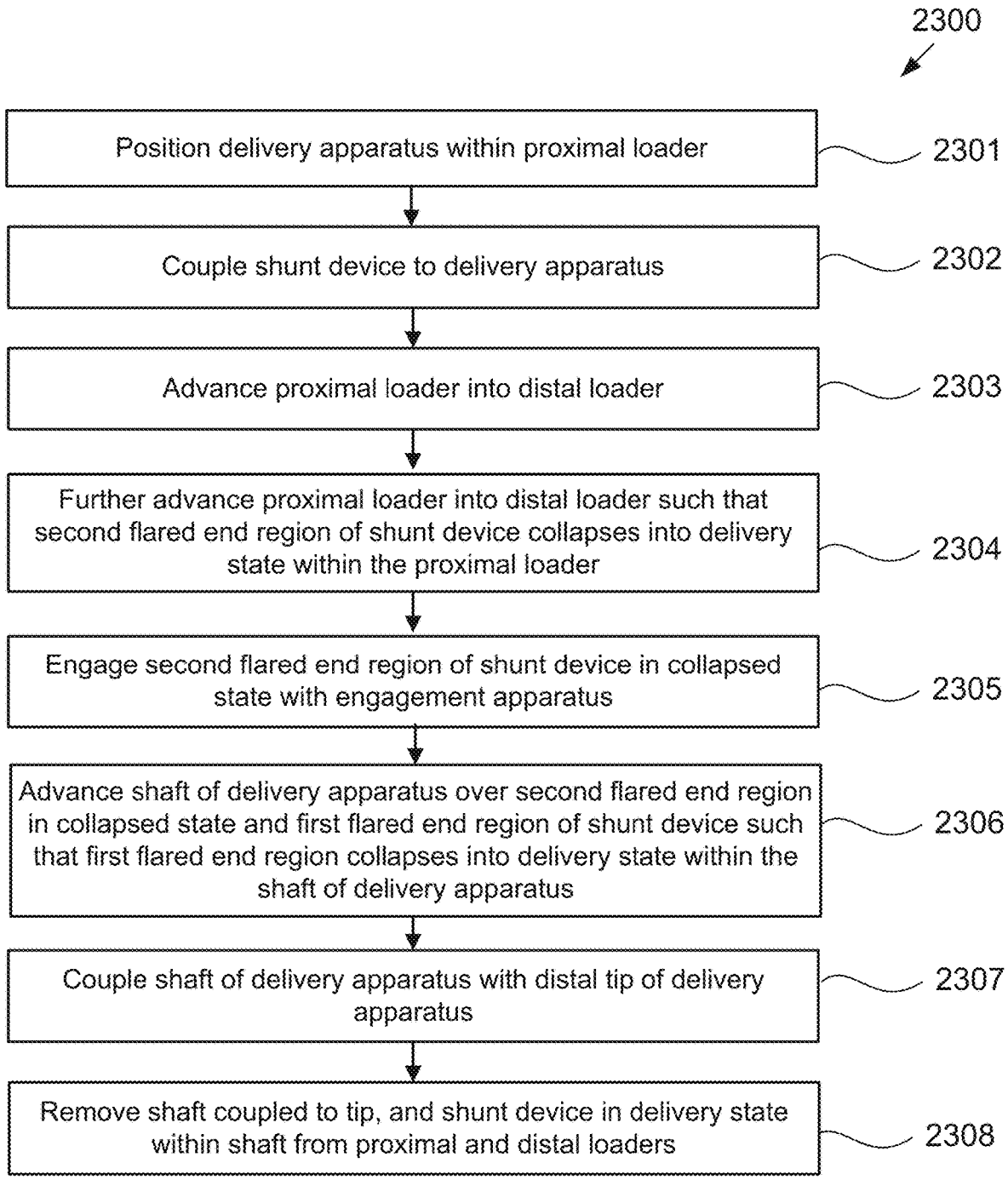
FIG. 23 is a flow chart of steps in a method of using the loading tool of FIG. 22 to load an exemplary shunt device into the apparatus of FIG. 21A.
Figure 24A:
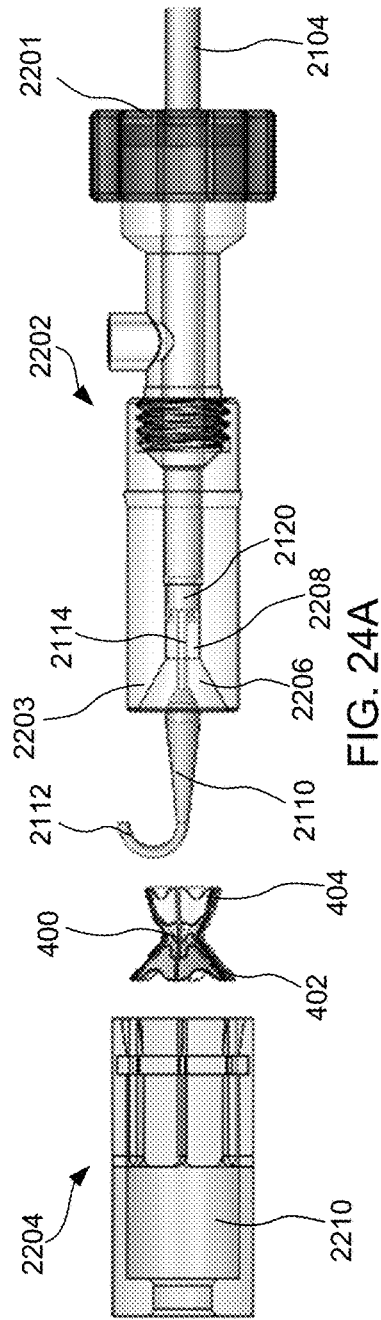

Exemplary method 2300 of using loading tool 2200 to load device 400 into apparatus 2100 will now be described with reference to FIG. 23. Some of the steps of method 2300 may be further elaborated be referring to FIGS. 24A-24F. FIG. 24A illustrates proximal loader 2202, distal loader 2204, the distal components of apparatus 2100, and device 400. As illustrated in FIG. 24A, apparatus 2100 is positioned within proximal loader 2202 such that the distal portion of catheter 2104 and engagement apparatus 2120 are disposed within lumen 2208, and distal tip 2110 extends beyond distal end 2203 of proximal loader 2202 (step 2301). As shown in FIG. 24A, distal tip 2110 is moveably coupled to catheter 2104 via pull-cord 2114. Engagement apparatus 2120 may be constructed similar to delivery apparatus 100 of FIG. 1A and delivery apparatus 700 of FIG. 7A. For example, engagement apparatus 2120 includes latching legs having hook portions which may be controllably transitioned between a disengaged and engaged position for engaging with device 400 in a collapsed delivery state. Engagement apparatus 2120 is moveably disposed within the lumen of catheter 2104 and may be coupled to the distal end of an inner catheter disposed within catheter 2104.

Figure 24B:
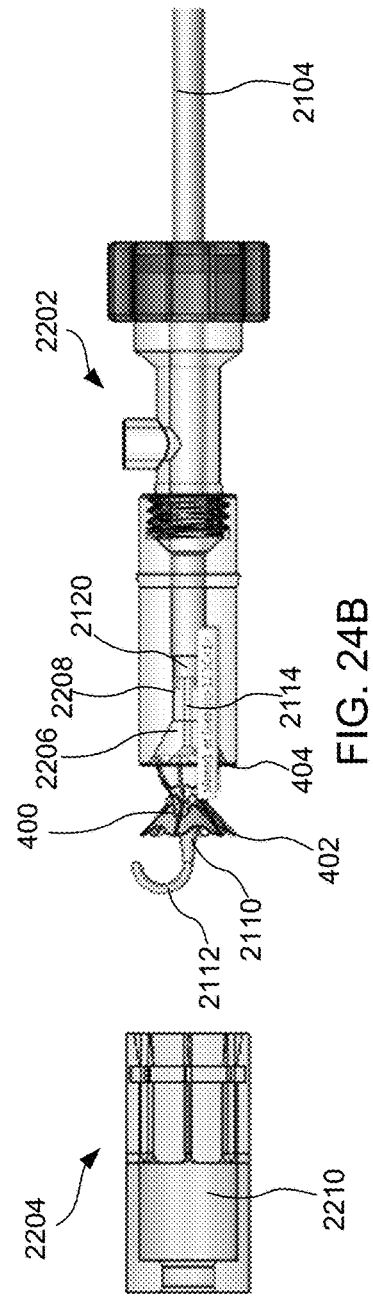

FIG. 24B illustrates device 400 coupled to distal tip 2110 of apparatus 2100 while apparatus 2100 is disposed within lumen 2208 of proximal loader 2202 (step 2302). Specifically, device 400 is inserted over pigtail-shaped portion 2112 to be disposed over distal tip 2110, such that the outlet end of second flared end region 403 of device 400 is adjacent to cavity 2206 of proximal loader 2202. Cavity 2206 has a size and shape that corresponds to first flared end region 401 in an expanded state, and which may receive the outlet end of second flared end region 403 of device 400 in the expanded state. This ensures that device 400 is properly loaded into apparatus 2100 as the inlet end of first flared end region 401 could not be inserted into cavity 2206 of proximal loader 2202.

Figure 24C:
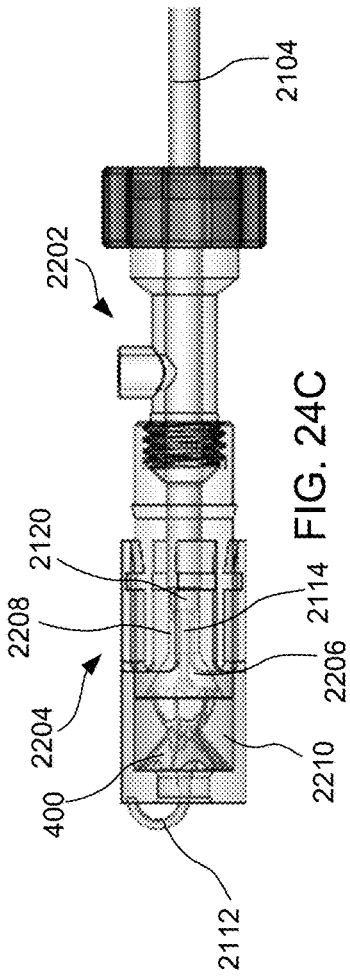

FIG. 24C illustrates proximal loader 2202 having apparatus 2100 coupled to device 400 therein, advanced within cavity 2210 of distal loader 2204 (step 2303). Specifically, proximal loader 2202 is advanced within cavity 2210 of distal loader 2204 until first flared end region 401 of device 400 contacts the inner wall of cavity 2210. As proximal loader 2202, and accordingly apparatus 2201, are further advanced into cavity 2210 of distal loader 2204 (step 2304), second flared end region 403 transitions from an expanded stated to a collapsed delivery state within lumen 2208 of proximal loader 2202 as illustrated in FIG. 24D. Specifically, the conical shape of cavity 2206 of proximal loader 2202 causes second flared end region 403 to crimp into the collapsed state as force is applied to second flared end region 403 by proximal loader 2202. In addition, pigtail-shaped portion 2212 and at least a portion of distal tip 2110 extend beyond an opening of distal loader 2204. Steps 2303 and 2304 may be completed in a single motion.

In accordance with the principles of the present invention, the latching legs and hook portions of engagement apparatus 2120 may be actuated to be in a disengaged position, e.g., contracted inward, before proximal loader 2202 is completely advanced within distal loader 2204 so that the engagement hooks of engagement apparatus 2120 may be appropriately aligned with the struts of second flared end region 403 of device 400, and so that second flared end region 403 can smoothly enter lumen 2208 of proximal loader 2202. Once aligned, the latching legs and hook portions of engagement apparatus 2120 may be actuated to be in a engaged position to engage with second flared end region 403 of device 400 within lumen 2208 of proximal loader 2202 (step 2305).

FIG. 24E illustrates catheter 2104 advanced further through lumen 2208 of proximal loader 2202 over engagement apparatus 2120, device 400, and pull-cord 2114 until the distal end of catheter 2104 engages with distal tip 2110 (step 2306). Specifically, as the distal tip of catheter 2104 comes into contact with first flared end region 401, further advancement of catheter 2104 against the outer surface of first flared end region 401 cause first flared end region 401 to crimp into a collapsed state within the lumen of catheter 2104. The distal end of catheter 2104 may then be coupled to distal tip 2110 (step 2307). Finally, apparatus 2100 having device 400 in a collapsed delivery state therein and engaged with engagement apparatus 2120 within catheter 2104 of apparatus 2100, is removed from proximal loader 2202 and distal loader 2204 (step 2308).

Figure 25A:
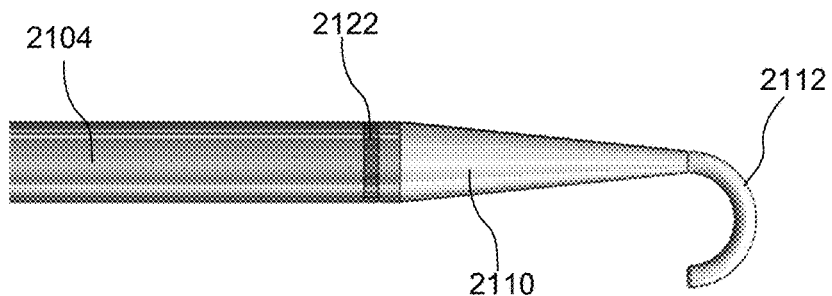
FIG. 25A illustrates the distal end of the apparatus of FIG. 21A having an exemplary shunt device loaded therein.
Figure 25B:
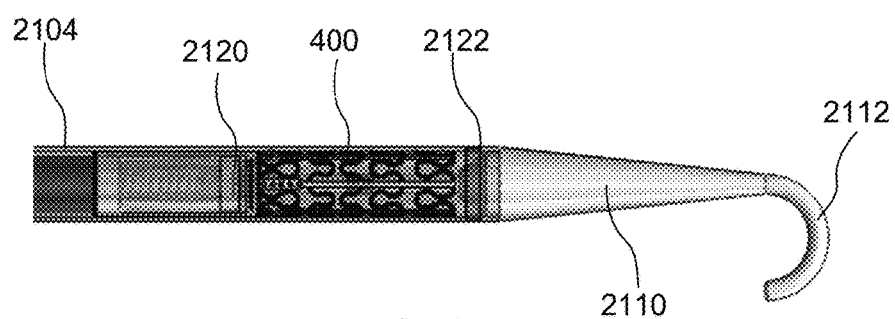
FIGS. 25B-25C illustrate the inner components of the distal end of the apparatus of FIG. 25A.

FIG. 25A illustrates catheter 2104 coupled to distal tip 2110 of apparatus 2100. As shown in FIG. 25A, apparatus 2100 may include radiopaque marker 2122 disposed at the distal end of catheter 2104 for assisting in accurate deployment of device 400 within the interatrial septum. Specifically, as described in further detail below, radiopaque marker 2122 may be visualized by the physician during the delivery procedure to ensure that it is aligned with the atrial septum for proper delivery. FIG. 25B illustrates the components within catheter 2104 with device 400 loaded therein. As illustrated in FIG. 25B, collapsed device 400 is positioned within catheter 2104 such that one end is engaged with engagement apparatus 2120, and the other end is aligned with radiopaque marker 2122 so that the neck region of device 400 is a predetermined distance from radiopaque marker 2122. As described in further detail below, knowing where the neck region of device 400 is within catheter 2104, by knowing its distance from radiopaque marker 2122 will assist in proper and accurate deployment of device 400 within the fossa ovalis.

Figure 25C:
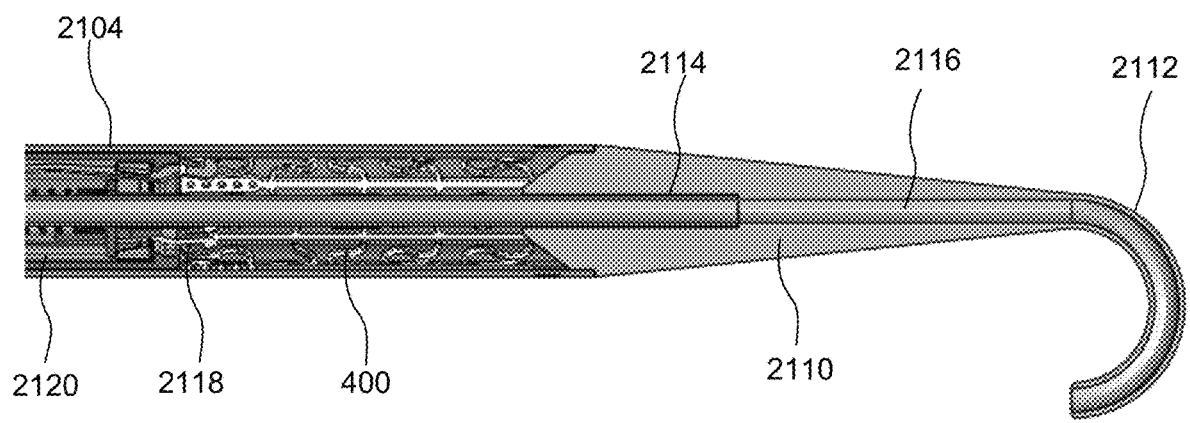

FIG. 25C is a cross-sectional view of the distal end of apparatus 2100. As shown in FIG. 25C, apparatus 2100 may include guidewire lumen 2116 extending therethrough, e.g., from an opening at the end of pigtail-shaped portion 2116 through distal tip 2110 and pull-cord 2114 to the proximal end of apparatus 2100. Guidewire lumen 2116 is sized and shaped to receive a guidewire so that apparatus 2100 may be advanced over the guidewire across the atrial septum for implantation of device 400. In addition, as illustrated in FIG. 25C, engagement apparatus 2120 includes hook portions 2118 which may be constructed similar to the hook portions of delivery apparatus 100 of FIG. 1A and delivery apparatus 700 of FIG. 7A, for engaging and disengaging device 400 with engagement apparatus 2120.

FIGS. 26A and 26B illustrates handle 2108 coupled to distal end 2106 of apparatus 2100. As shown in FIG. 26A, handle 2108 includes safety trigger 2126 and knob 2124. As illustrated in FIG. 26B, knob 2124 includes a threaded portion that corresponds with threaded portion of catheter component 2127 coupled to catheter 2104. Accordingly, as knob 2124 is rotated about the longitudinal axis of handle 2108, rotational movement of knob 2124 is converted to translational movement of catheter component 2127 along the longitudinal axis of handle 2108, thereby causing movement of catheter 2104 relative to engagement apparatus 2120. This permits gradual adjustment of the length of catheter 2104 relative to engagement apparatus 2120, and accordingly halfway-retrieval of device 400 when device is halfway deployed as will be described in further detail below. Knob 2124 may not be rotated until safety trigger 2126 is moved from a locked position to an unlocked position.

Exemplary method 2700 of delivering device 400 to reduce left atrial pressure in a subject, for example, a human having a heart pathology, using apparatus 2100 illustrated in FIG. 21A will now be described with reference to FIG. 27. Some of the steps of method 2700 may be further elaborated by referring to FIGS. 28A-28I.

Figure 28A:
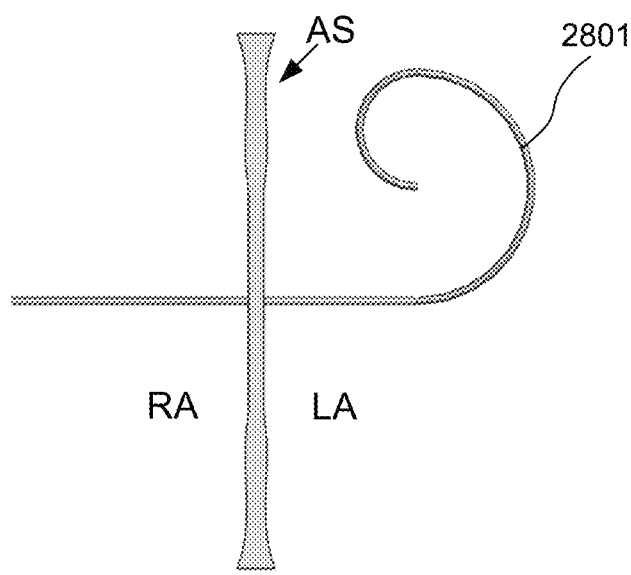
FIGS. 28A-28I schematically illustrate steps taken during the method of FIG. 27, according to some embodiments of the present invention.

At step 2701, an interatrial shunt, e.g., device 400, and apparatus 2100 of FIG. 21A for delivering device 400 are provided. Then, at step 2702, device 400 is collapsed radially to a contracted delivery state and coupled to apparatus 2100, e.g., using method 2300 of FIG. 23. Steps 2703 and 2704 are similar to steps 503 and 504 described in FIG. 5, and thus for brevity these steps are not discussed again here. FIG. 28A illustrates guidewire 2801 disposed across the atrial septum in left atrium LA (step 2704).

Figure 28B:
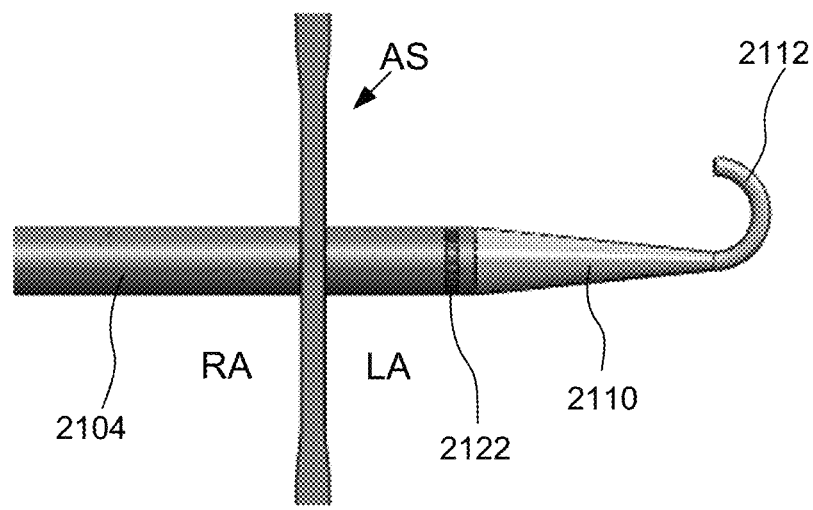
Figure 28C:
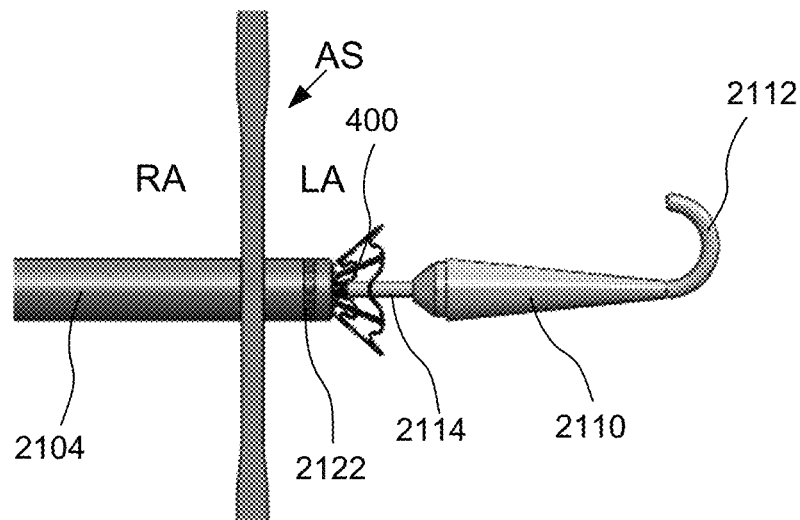

Pigtail-shaped portion 2112 of distal tip 2110 of delivery apparatus 2100 with device 400 collapsed therein and coupled to engagement apparatus 2120 of apparatus 2100 is then advanced over guidewire 2801 through the puncture in the fossa ovalis and into left atrium LA (step 2705) as illustrated in FIG. 28B. Next, catheter 2104 is retracted proximally relative to distal tip 2110 and engagement apparatus 2120 coupled to collapsed device 400 such that device 400 is partially advanced out of catheter 2104 (step 2706). Such advancement causes device 400 to partially protrude out of catheter 2104 and into left atrium LA, which causes the first flared end region to expand to its deployed expanded state in the left atrium LA, as shown in FIG. 28C.

Figure 28D:
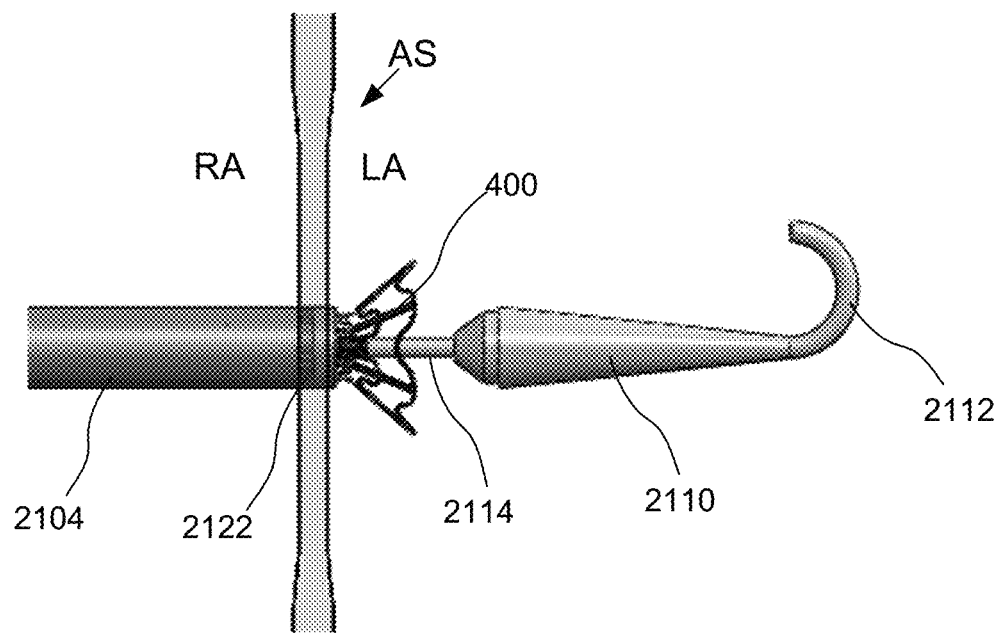
Figure 28E:
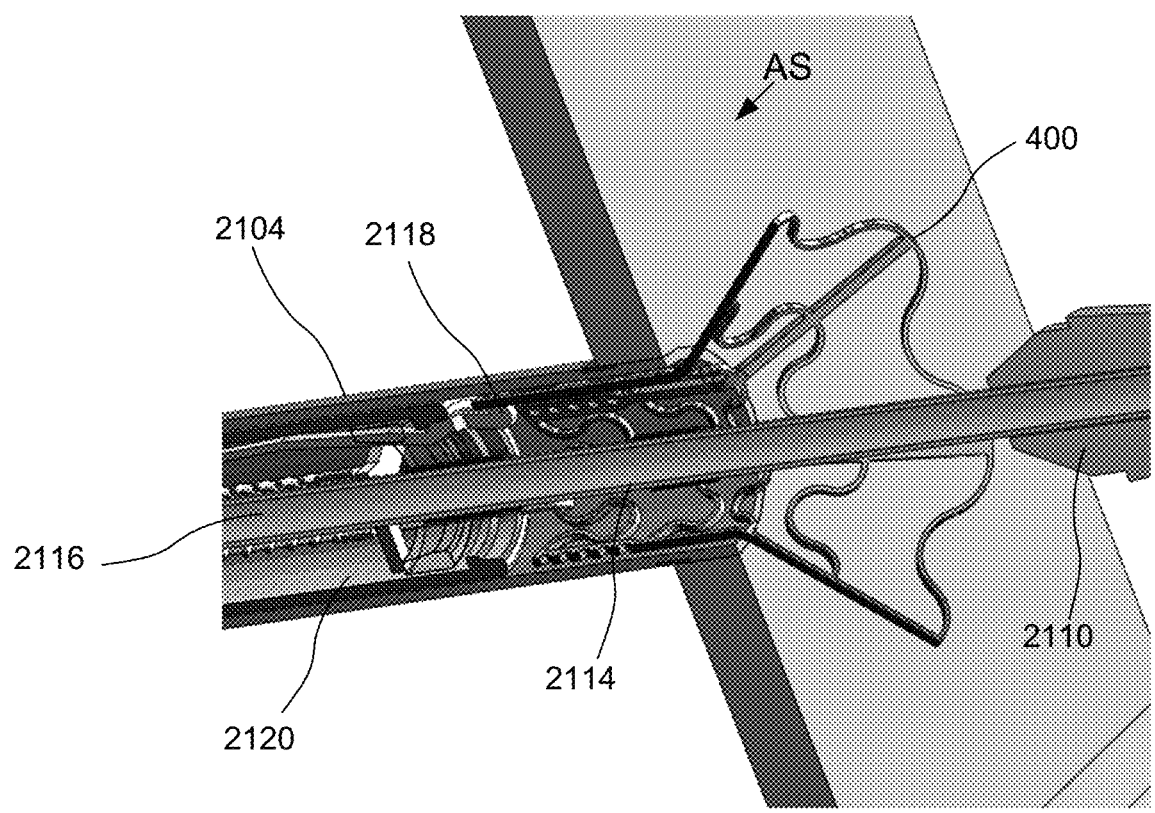

Then, under fluoroscopic and/or echocardiographic visualization, apparatus 2100 may be repositioned such that radiopaque marker 2801 is aligned with the fossa ovalis (step 2707) as illustrated in FIGS. 28D and 28E. As shown in FIG. 28E, when apparatus 2100 is in the proper position, the neck region of device 400 will be aligned with the fossa ovalis for accurate deployment of device 400 within the atrial septum. Thus, device 400 will be loaded to a specific position within catheter 2104 of apparatus 2100 relative to radiopaque marker 2122 during method 2300 described above.

Figure 28F:
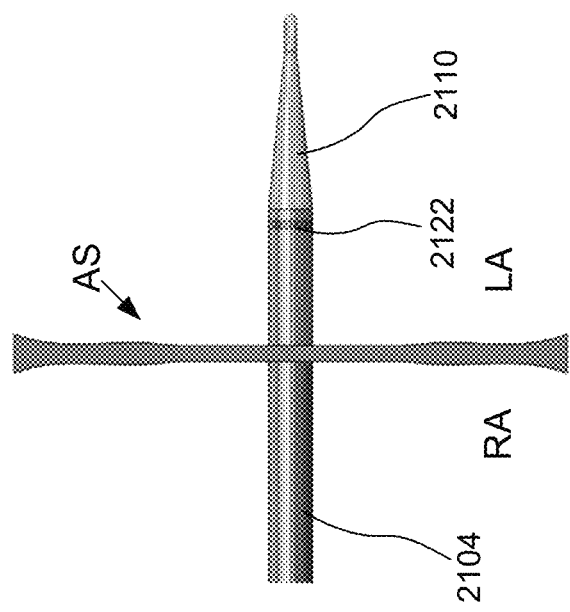

If for any reason device 400 is not in the proper position for deployment within the atrial septum, catheter 2104 may be advanced over device 400 while distal tip 2110 is stationary, thereby collapsing the first flared end region within catheter 2104 (step 2708) as illustrated in FIG. 28F. Specifically, knob 2124 of handle 2108 may be rotated to cause catheter 2104 to move translationally relative to engagement apparatus 2120 and distal tip 2110 of apparatus 2100, to thereby collapse device 400 within catheter 2104. For example, catheter 2104 may be moved over collapsed device 400 until catheter 2104 engages with distal tip 2110 as shown in FIG. 28F. Apparatus 2100, with device 400 disposed therein, may then be retrieved, e.g., over guidewire 2801 (step 2709). Alternatively, apparatus 2100 may be repositioned relative to the fossa ovalis of the atrial septum prior to returning to step 2706 and partially advancing the first flared end region out of catheter 2104 within left atrium LA.

Figure 28G:
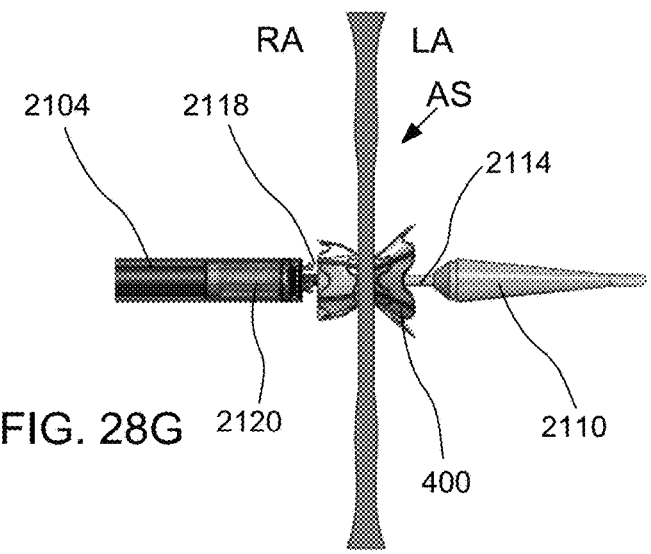

After step 2707 described above, when device 400 is properly positioned relative to the atrial septum, engagement apparatus 2120 may be disengaged from device 400, e.g., hook portions 2118 may be moved from an engaged positioned radially inward to a disengaged position. Then, catheter 2104 may be retracted proximally relative to distal tip 2110, causing the second flared end region of device 400 to be exposed within right atrium RA beyond the distal end of catheter 2104 such that the second flared end region transitions from the collapsed delivery state to an expanded state within right atrium RA (step 2710) as illustrated in FIG. 28G. Specifically, knob 2124 of handle 2108 may be rotated in the opposite direction to cause catheter 2104 to move translationally relative to engagement apparatus 2120 and distal tip 2110 of apparatus 2100, to thereby expose the second flared end region of device 400 within right atrium RA. Accordingly, the flared end region of device 400 will be disposed within left atrium LA, the neck region of device 400 will be lodged within the puncture through the fossa ovalis, and the second flared end region of device 400 will be disposed within right atrium RA. In addition, pull-cord 2114 will be positioned within a central lumen of device 400.

Figure 28H:
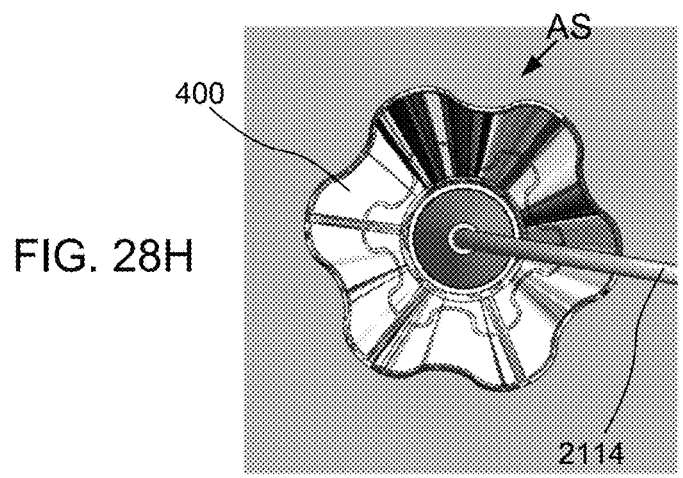
Figure 28I:
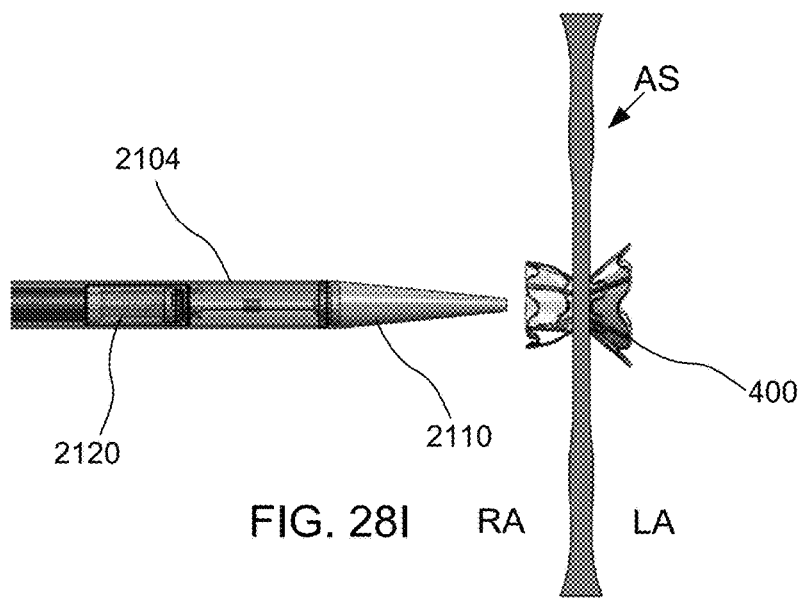
Figure 29B:
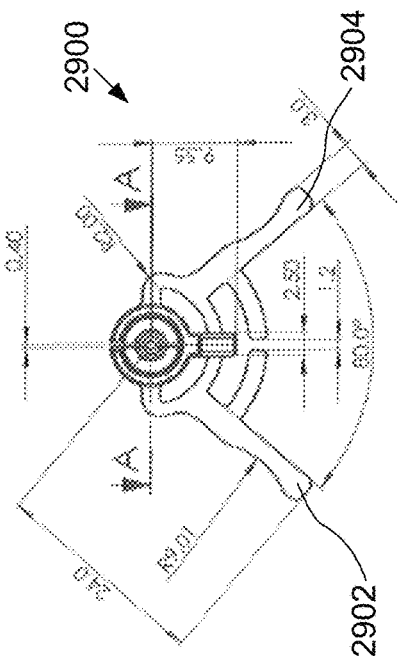
FIGS. 29A-29D illustrate a guidewire loading tool constructed in accordance with the principles of the present invention.
Figure 29D:
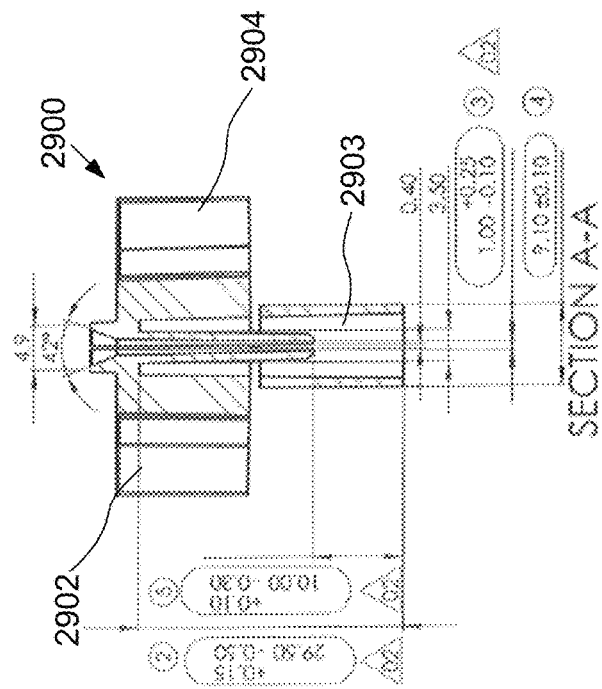
Figure 29A:
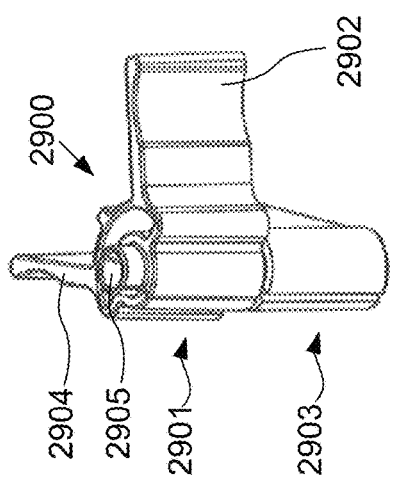
Figure 29C:
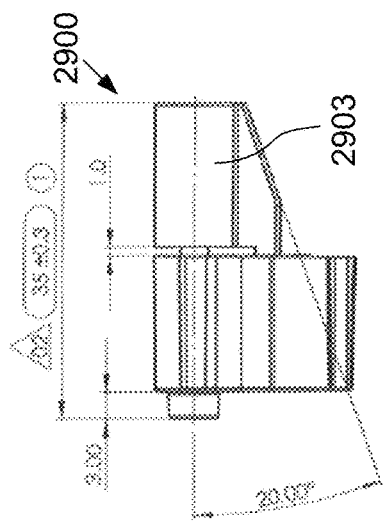

As illustrated in FIG. 28H, which shows device 400 from within right atrium RA, distal tip 2110 is sized and shaped to fit through the central lumen of device 400 in the full expanded state. When device 400 is fully expanded within the atrial septum, apparatus 2100 may be retrieved (step 2711) by pulling distal 2100 proximally, e.g., until catheter 2104 engages with distal tip 2110 as shown in FIG. 28I. Guidewire 2801 may then be removed. Blood may then be shunted from left atrium LA to right atrium RA through device 400, e.g., when left atrial pressure exceeds right atrial pressure (step 2712).

Referring now to FIGS. 29A-29D, an exemplary guidewire loading tool constructed in accordance with the principles of the present invention is described. Guidewire loading tool 2900 is designed for use with loading cartridge 614 of FIGS. 6D-6I. Specifically, as illustrated in FIGS. 29A-29D, guidewire loading tool 2900 has proximal portion 2903 and distal portion 2901, and two flexible wings, e.g., first flexible wing 2902 and second flexible wing 2904, coupled to and extending radially away from distal portion 2901. First flexible wing 2902 and second flexible wing 2904 each have lateral end portions having an edge that runs parallel to the longitudinal axis of proximal portion 2903 and distal portion 2901, which permit guidewire loading tool 2900 to be placed on a flat horizontal surface while a guidewire is loaded therein as described in further detail below.

In addition, guidewire loading tool 2900 has central lumen 2905 extending through proximal portion 2903 and distal portion 2901, sized and shaped to receive loading cartridge 614 therein, e.g., when device 400 is collapsed in a delivery state within loading cartridge 614 as described above with reference to FIG. 6F. Referring again to FIG. 29A, first and second flexible wings 2902 and 2904 are designed such that when a force is applied against first and second flexible wings 2902 and 2904 toward each other, the diameter of central lumen 2905 is increased to permit insertion and removal of loading cartridge 614 therein. Accordingly, first and second flexible wings 2902 and 2904 are biased toward an open position whereby central lumen 2905 has a smaller diameter than when first and second flexible wings 2902 and 2904 are pressed toward each other.

Figure 30A:
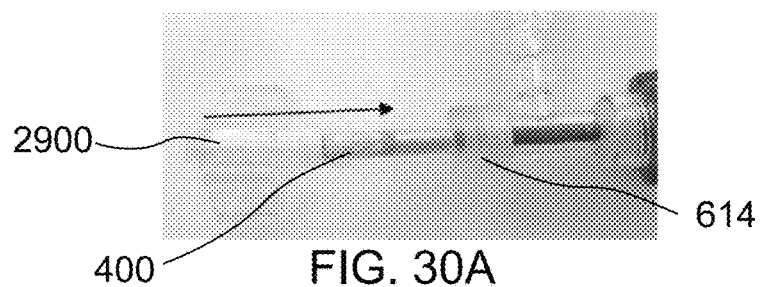
FIGS. 30A-30E illustrates a method of using the guidewire loading tool of FIGS. 29A-29D.
Figure 30B:
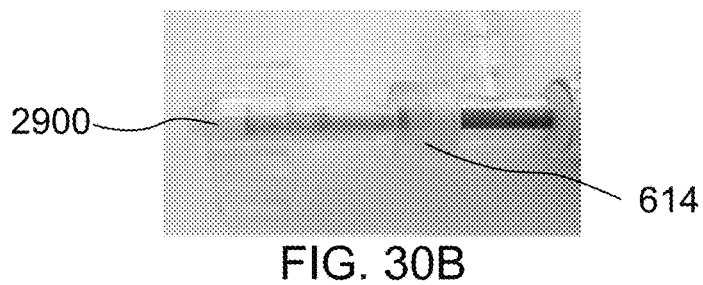

Referring now to FIGS. 30A-30E, an exemplary method of using guidewire loading tool 2900 to load a guidewire is provided. As shown in FIG. 30A, guidewire loading tool 2900 is inserted over loading cartridge 614 having device 400 collapsed therein. Specifically, first and second flexible wings 2902 and 2904 are pressed toward each other to increase the diameter of central lumen 2905, and loading cartridge 614 is positioned within central lumen 2905. First and second flexible wings may then be released such that loading cartridge 614 is securely disposed within central lumen 2905 of guidewire loading tool 2900 as illustrated in FIG. 30B.

Figure 30C:
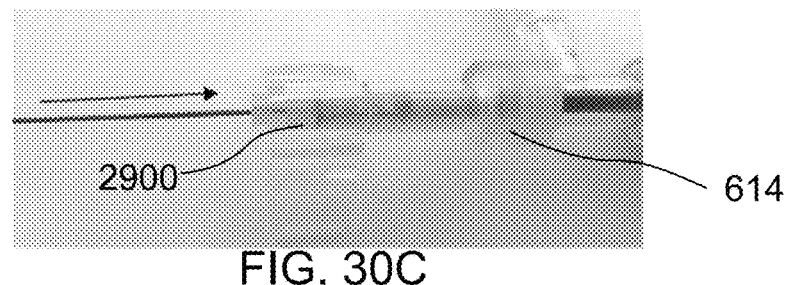
Figure 30D:
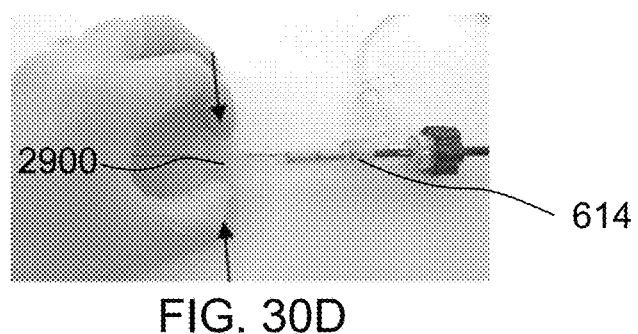
Figure 30E:
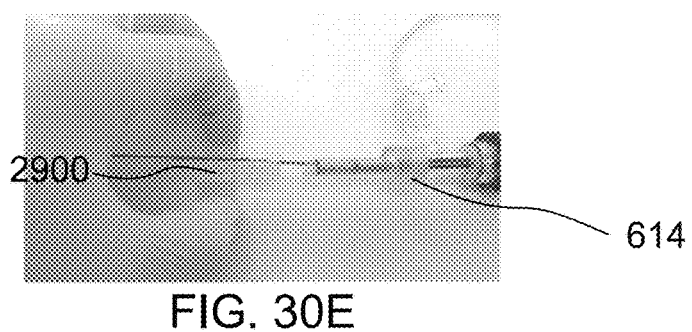

Next, as illustrated in FIG. 30C, a guidewire is inserted through a lumen of device 400 collapsed within loading cartridge 614 disposed within central lumen 2905 of guidewire loading tool 2900. The guidewire may be fed therethrough and extend beyond a proximal end of loading cartridge 614. As shown in FIG. 30D, when the guidewire is sufficiently inserted within loading cartridge 614 and guidewire loading tool 2900, first and second flexible wings 2902 and 2904 may be pressed toward each other to enlarge central lumen 2905. Accordingly, guidewire loading tool 2900 may be removed from loading cartridge 614 as shown in FIG. 30E.

While various illustrative embodiments of the invention are described above, it will be apparent to one skilled in the art that various changes and modifications may be made herein without departing from the invention. It will further be appreciated that the devices described herein may be implanted in other positions in the heart. For example, device 400 may be implanted in an orientation so as to shunt blood from the right atrium to the left atrium, thus decreasing right atrial pressure; such a feature may be useful for treating a high right atrial pressure that occurs in pulmonary hypertension. Similarly, device 400 may be implanted across the ventricular septum, in an orientation suitable to shunt blood from the left ventricle to the right ventricle, or in an orientation suitable to shunt blood from the right ventricle to the left ventricle. The appended claims are intended to cover all such changes and modifications that fall within the true spirit and scope of the invention.

What is claimed:

1. An apparatus for delivering a shunt to an atrial septum of a patient, the apparatus comprising:
   a sheath comprising a distal region, a proximal region, and a sheath lumen extending therethrough, the sheath lumen sized and shaped to receive the shunt in a contracted delivery state, the distal region of the sheath sized and shaped for percutaneous advancement to the atrial septum;

a first catheter moveably disposed within the sheath lumen, the first catheter comprising a first catheter lumen extending therethrough;

a hub moveably disposed within the sheath lumen distal to the first catheter, the hub comprising an engagement portion, a ring portion, a hub lumen extending therethrough, and one or more engagers disposed on an outer surface of the engagement portion, the engagement portion having a diameter smaller than a diameter of the ring portion, the one or more engagers configured to releasably engage the shunt in the contracted delivery state within the sheath lumen;

a second catheter moveably disposed within the first catheter lumen and the hub lumen, wherein the first catheter and the hub are movable while the second catheter remains in place; and a handle disposed at the proximal region of the sheath, wherein the first catheter, the hub, and the second catheter are independently movable relative to the sheath responsive to actuation at the handle to facilitate transition of the shunt from the contracted delivery state to an expanded deployed state at the atrial septum, wherein the handle further comprises a knob that when actuated facilitates deployment of and/or halfway retrieval of the shunt at the atrial septum by adjusting a length of the sheath relative to the first catheter.

2. The apparatus of claim 1, wherein the engagement portion of the hub is distal to the ring portion of the hub.

3. The apparatus of claim 1, wherein a proximal expandable end of the shunt, in the contracted delivery state within the sheath lumen, is positioned between the one or more engagers and the ring portion and between an outer surface of the engagement portion and an inner wall of the sheath.

4. The apparatus of claim 1, wherein the hub further comprises a proximal portion, and wherein the first catheter comprises a cavity sized and shaped to receive at least a portion of the proximal portion to limit movement of the hub relative to the first catheter.

5. The apparatus of claim 1, wherein the second catheter comprises a stop disposed at a distal end of the second catheter, and wherein the hub comprises a cavity sized and shaped to receive at least a portion of the stop to limit movement of the hub relative to the second catheter.

6. The apparatus of claim 1, wherein the second catheter comprises a guidewire lumen extending therethrough configured to receive a guidewire.

7. The apparatus of claim 1, wherein the knob is configured to gradually adjust the length of the sheath relative to the first catheter via a threaded connection.

8. The apparatus of claim 1, wherein the handle comprises a first actuator, the first actuator coupled to the sheath such that actuation of the first actuator causes the sheath to move relative to the hub, the first catheter, and the second catheter.

9. The apparatus of claim 8, wherein the handle further comprises a second actuator, the second actuator coupled to the second catheter such that actuation of the second actuator causes the second catheter to move relative to the sheath, the hub, and the first catheter.

10. The apparatus of claim 9, wherein the second actuator is coupled to the second catheter via one or more guiderails and a pusher plate.

11. The apparatus of claim 10, wherein the first actuator is configured to move along the one or more guiderails.

12. The apparatus of claim 9, wherein the handle comprises a third actuator configured to be actuated to couple or decouple the hub and the first catheter.

13. An apparatus for delivering a shunt to an atrial septum of a patient, the apparatus comprising:
a sheath comprising a distal region, a proximal region, and a sheath lumen extending therethrough, the sheath lumen sized and shaped to receive the shunt in a contracted delivery state, the distal region of the sheath sized and shaped for percutaneous advancement to the atrial septum;

a first catheter moveably disposed within the sheath lumen, the first catheter comprising a first catheter lumen extending therethrough;

a hub moveably disposed within the sheath lumen distal to the first catheter, the hub comprising a hub lumen extending therethrough and one or more engagers configured to releasably engage the shunt in the contracted delivery state within the sheath lumen;

a second catheter moveably disposed within the first catheter lumen and the hub lumen, wherein the first catheter and the hub are movable while the second catheter remains in place; and a handle disposed at the proximal region of the sheath, wherein the first catheter, the hub, and the second catheter are independently movable relative to the sheath responsive to actuation at the handle to facilitate transition of the shunt from the contracted delivery state to an expanded deployed state at the atrial septum, the handle comprising:

a first actuator coupled to the sheath such that actuation of the first actuator causes the sheath to move relative to the hub, the first catheter, and the second catheter;

a second actuator coupled to the second catheter such that actuation of the second actuator causes the second catheter to move relative to the sheath, the hub, and the first catheter;

a third actuator configured to be actuated to couple or decouple the hub and the first catheter; and an actuation ring positioned between the second actuator and the third actuator, the actuation ring comprising an indented distal edge configured to engage with a toothed proximal edge of the third actuator, and a grooved proximal edge configured to engage with an indented distal edge of the second actuator.

14. The apparatus of claim 13, wherein actuation of the third actuator orients the actuation ring such that actuation of the second actuator is inhibited.

15. A method for delivering a shunt at an atrial septum of a patient, the method comprising:
selecting a sheath and a delivery apparatus comprising a first catheter, a hub distal to and releasably coupled to the first catheter, the hub having one or more engagers disposed thereon, the one or more engagers configured to releasably engage with the shunt in a contracted delivery state within a lumen of the sheath, and a second catheter extending through a center lumen of the first catheter and the hub, wherein the first catheter, the hub, and the second catheter are independently moveable relative to the sheath upon actuation of a handle operatively coupled to the sheath and the delivery apparatus, the handle comprising a first actuator coupled to the sheath, a second actuator coupled to the second catheter, a third actuator, and an actuation ring positioned between the second actuator and the third actuator, the actuation ring comprising an indented distal edge configured to engage with a toothed proximal edge of the third actuator, and a grooved proximal edge configured to engage with an indented distal edge of the second actuator;

advancing a distal end of the sheath through the atrial septum into a first atrium;

advancing the delivery apparatus within the lumen of the sheath, the delivery apparatus releasably coupled to the shunt in the contracted delivery state within the lumen of the sheath;

actuating the first actuator of the handle to move the delivery apparatus distally relative to the sheath such that a first expandable end of the shunt extends distally out the distal end of the sheath and transitions from the contracted state within the lumen of the sheath to an expanded state in the first atrium;

actuating the second actuator of the handle to move the second catheter distally relative to the sheath, the first catheter, and the hub;

moving the delivery apparatus proximally until the first expandable end of the shunt rests against the atrial septum from within the first atrium;

actuating the third actuator of the handle to decouple the hub and the first catheter;

moving the first catheter and the sheath proximally relative to the hub to disengage a second expandable end of the shunt with the one or more engagers of the hub and expose the second expandable end of the shunt from the sheath to transition from the contracted state within the lumen of the sheath to an expanded state in a second atrium; and removing the sheath and the delivery apparatus from the patient such that the shunt is positioned within the atrial septum to permit blood to flow through an opening of the shunt and thereby through the atrial septum.

16. The method of claim 15, further comprising actuating the handle to adjust a length of the delivery apparatus relative to a length of the sheath prior to disengaging the second expandable end of the shunt with the one or more engagers of the hub to assist in halfway retrieval of the shunt.

17. The method of claim 16, wherein actuating the handle gradually adjusts the length of the delivery apparatus relative to the length of the sheath via a threaded connection to facilitate retrieving the shunt in a partially deployed state.

18. The method of claim 15, wherein the hub comprises an engagement portion and a ring portion, the engagement portion of the hub having a diameter smaller than a diameter of the ring portion, and wherein the one or more engagers are disposed circumferentially around the engagement portion of the hub.

19. The apparatus of claim 18, wherein the second expandable end of the shunt is positioned between the one or more engagers and the ring portion and between an outer surface of the engagement portion and an inner wall of the sheath in the contracted delivery state within the lumen of the sheath.

20. The method of claim 15, wherein the second catheter comprises a guidewire lumen extending therethrough configured to receive a guidewire, the method further comprising inserting a guidewire percutaneously through the atrial septum into the first atrium, and wherein advancing the delivery apparatus within the lumen of the sheath comprises advancing the delivery apparatus over the guidewire.

* * * * *